United States Patent
Arai et al.

(10) Patent No.: US 10,173,999 B2
(45) Date of Patent: Jan. 8, 2019

(54) CYCLIC AMINE DERIVATIVE AND PHARMACEUTICAL USE THEREOF

(71) Applicant: Toray Industries, Inc., Tokyo (JP)

(72) Inventors: Tadamasa Arai, Kamakura (JP);
Yasuhiro Morita, Kamakura (JP);
Shuji Udagawa, Kamakura (JP);
Katsuhiko Iseki, Kamakura (JP);
Naoki Izumimoto, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 15/553,211

(22) PCT Filed: Feb. 26, 2016

(86) PCT No.: PCT/JP2016/055814
§ 371 (c)(1),
(2) Date: Aug. 24, 2017

(87) PCT Pub. No.: WO2016/136944
PCT Pub. Date: Sep. 1, 2016

(65) Prior Publication Data
US 2018/0065950 A1 Mar. 8, 2018

(30) Foreign Application Priority Data
Feb. 27, 2015 (JP) .................. 2015-038809

(51) Int. Cl.
*C07D 401/06* (2006.01)
*A61K 31/4178* (2006.01)
*A61K 31/454* (2006.01)
*A61K 31/496* (2006.01)
*C07D 403/06* (2006.01)

(52) U.S. Cl.
CPC ........ *C07D 401/06* (2013.01); *A61K 31/4178* (2013.01); *A61K 31/454* (2013.01); *A61K 31/496* (2013.01); *C07D 403/06* (2013.01)

(58) Field of Classification Search
CPC ................................................. C07D 401/06
See application file for complete search history.

(56) References Cited

FOREIGN PATENT DOCUMENTS

| FR | 2 567 885 A1 | 1/1986 |
| GB | 2 163 150 A | 2/1986 |
| JP | 2005-527519 A | 9/2005 |
| JP | 2006-8664 A | 1/2006 |
| WO | 03/031432 A1 | 4/2003 |
| WO | 2010/119875 A1 | 10/2010 |
| WO | 2013/147160 A1 | 10/2013 |
| WO | 2015/046403 A1 | 4/2015 |

OTHER PUBLICATIONS

Akiko Okifuji et al., "Management of Fibromyalgia Syndrome: Review of Evidence," Pain and Therapy, vol. 2, 2013, pp. 87-104.

*Primary Examiner* — Paul V Ward
(74) *Attorney, Agent, or Firm* — DLA Piper LLP (US)

(57) ABSTRACT

A compound exerts an analgesic effect against pain, in particular, neuropathic pain and/or fibromyalgia syndrome. A cyclic amine derivative represented by the following general formula, or a pharmacologically acceptable salt thereof:

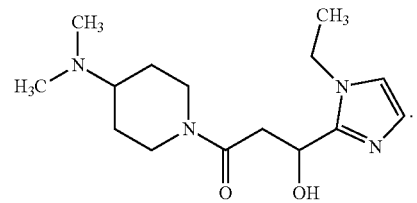

Methods using the compound including the cyclic amine derivative or a pharmacologically acceptable salt thereof to treat pain, neuropathic pain and fibromyalgia syndrome.

11 Claims, 18 Drawing Sheets

CYCLIC AMINE DERIVATIVE AND PHARMACEUTICAL USE THEREOF

TECHNICAL FIELD

This disclosure relates to a cyclic amine derivative and pharmaceutical use thereof.

BACKGROUND

Pain is an unpleasant sensory and emotional experience associated with actual or potential tissue damage. Pain is classified according to cause into nociceptive pain, neuropathic pain and psychogenic pain. As pain caused by an unknown cause, fibromyalgia syndrome is known.

Neuropathic pain is pathological pain caused by peripheral or central nervous system dysfunction, more specifically, pain caused by e.g., direct damage and oppression of the nerve tissue despite of no nociceptive stimulus to a nociceptor. As an therapeutic agent for neuropathic pain, an anticonvulsant, an antidepressant, an anxiolytic drug or an antiepileptic drug (gabapentin, pregabalin or the like) is used.

Fibromyalgia syndrome is a disorder in which systemic pain is the leading symptom and neuropsychiatric and neurovegetative symptoms are the secondary symptoms. As the therapeutic agents for fibromyalgia syndrome, pregabalin, which has been approved in the United States and Japan, duloxetine and milnacipran, which have been approved in the United States, are principally used. Also, drugs which are not approved as a therapeutic agent for fibromyalgia syndrome, i.e., a nonsteroidal anti-inflammatory agent, an opioid compound, an antidepressant, an anticonvulsant and an antiepileptic drug are used. However, nonsteroidal anti-inflammatory agents and opioid compounds are generally said to have a low therapeutic effect (FR 2 567 885).

FR '885 discloses that substituted piperidines have a cardiotonic activity. JP 2006-008664 discloses that imidazole derivatives have an FXa inhibitory effect. WO 2003/031432 suggests that substituted piperidines have a potential drug efficacy against overweight or obesity. WO 2013/147160 discloses that an imidazole derivative has an analgesic action.

However, therapy with a conventional therapeutic agent for neuropathic pain is highly frequently associated with central nervous system adverse effects (e.g., dizziness, nausea or vomiting). To enable long-term administration, development of a novel therapeutic agent for neuropathic pain has been desired.

Even pregabalin, duloxetine and milnacipran, which have been approved as therapeutic agents for fibromyalgia syndrome, fail to provide clinically satisfactory therapeutic effect against fibromyalgia syndrome and their drug efficacy significantly varies among patients. In that context, it has been strongly desired to develop a novel therapeutic agent for fibromyalgia syndrome having a strong pharmacological activity and exerting a therapeutic effect on a wide variety of patients.

FR '885 suggests that the substituted piperidines described therein have an efficacy for migraine and WO '160 discloses that the imidazole derivative described therein has an analgesic action. However, neither disclosure of the compound itself having an analgesic action nor suggestion on the relevancy of an analgesic action to a chemical structure is provided. JP '664 which describes imidazole derivatives and WO '432 which describes substituted piperidines neither disclose nor suggest potentiality of analgesic action that these compounds have.

Under the circumstances, it could be helpful to provide a compound having an analgesic action for pain, in particular, neuropathic pain and/or fibromyalgia syndrome.

SUMMARY

We found a cyclic amine derivative having a strong analgesic effect against pain, in particular, neuropathic pain and/or fibromyalgia syndrome.

We thus provide a cyclic amine derivative represented by general formula (I) or a pharmacologically acceptable salt thereof:

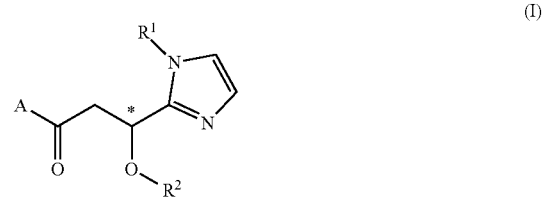

wherein carbon marked with * is an asymmetric carbon, and A represents a group represented by general formulae (IIa), (IIb) or (IIc),

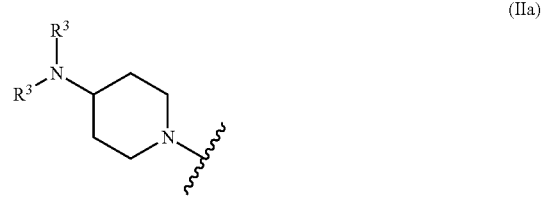

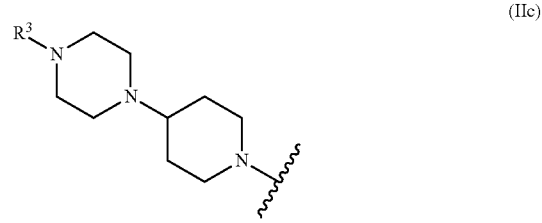

wherein $R^1$ represents a methyl group or an ethyl group optionally substituted with a halogen atom, $R^2$ represents a hydrogen atom or an alkylcarbonyl group having 2 to 5 carbon atoms, each $R^3$ independently represents a methyl group or an ethyl group, and n represents 1 or 2.

In the aforementioned cyclic amine derivative, it is preferable that A is a group represented by general formula (IIa), in which $R^1$ is more preferably a methyl group or an ethyl group optionally substituted with a fluorine atom; and further preferably a methyl group, an ethyl group, a difluoromethyl group or a 2,2,2-trifluoroethyl group. Analgesic action can be enhanced by defining as mentioned above.

In the above cyclic amine derivative, it is preferable that A is a group represented by general formulae (IIb) or (IIc), in which $R^1$ is more preferably a methyl group or an ethyl group optionally substituted with a fluorine atom, and further preferably a methyl group, an ethyl group, a difluoromethyl group or a 2,2,2-trifluoroethyl group. Analgesic action can be enhanced by defining as mentioned above.

In the above cyclic amine derivative, it is preferable that A is a group represented by general formula (IIa) and that the stereochemical configuration of the asymmetric carbon marked with * is S, in which $R^1$ is more preferably a methyl group or an ethyl group optionally substituted with a fluorine atom and further preferably a methyl group, an ethyl group, a difluoromethyl group or a 2,2,2-trifluoroethyl group. Analgesic action can be further enhanced by defining as mentioned above.

We also provide a medicine containing a cyclic amine derivative represented by general formula (I), or a pharmacologically acceptable salt thereof as an active ingredient.

The medicine is preferably an analgesic agent, and particularly preferably a therapeutic agent for neuropathic pain or a therapeutic agent for fibromyalgia syndrome.

We also provide a pharmaceutical composition containing a cyclic amine derivative represented by general formula (I) or a pharmacologically acceptable salt thereof and, e.g., a pharmacologically acceptable excipient.

We also provide a cyclic amine derivative represented by general formula (I) or a pharmacologically acceptable salt thereof for use as a medicine.

We also provide a cyclic amine derivative represented by general formula (I) or a pharmacologically acceptable salt thereof for use in pain treatment. The pain is preferably neuropathic pain or fibromyalgia syndrome.

We also provide use of a cyclic amine derivative represented by general formula (I) or a pharmacologically acceptable salt thereof for treating pain. The pain is preferably neuropathic pain or fibromyalgia syndrome.

We also provide use of a cyclic amine derivative represented by general formula (I) or a pharmacologically acceptable salt thereof in producing a medicine for treating pain. The pain is preferably neuropathic pain or fibromyalgia syndrome.

We also provide a method of treating pain including administering a therapeutically effective amount of the cyclic amine derivative represented by general formula (I) or a pharmacologically acceptable salt thereof to a patient in need thereof. The pain is preferably neuropathic pain or fibromyalgia syndrome.

The cyclic amine derivative or a pharmacologically acceptable salt thereof has a strong analgesic effect against pain, in particular, neuropathic pain and fibromyalgia syndrome.

DETAILED DESCRIPTION

Figure 1:
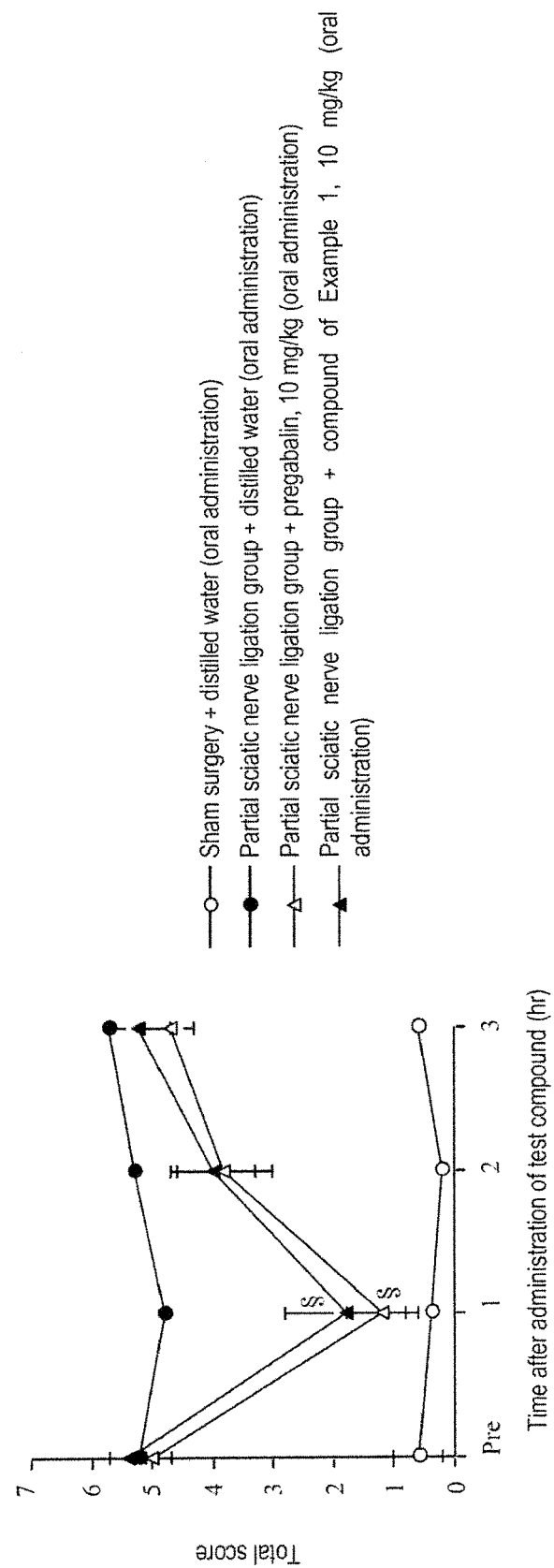
FIG. 1 is a graph showing the effect of the compound of Example 1 in a mouse partial sciatic nerve ligation model (oral administration).
Figure 2:
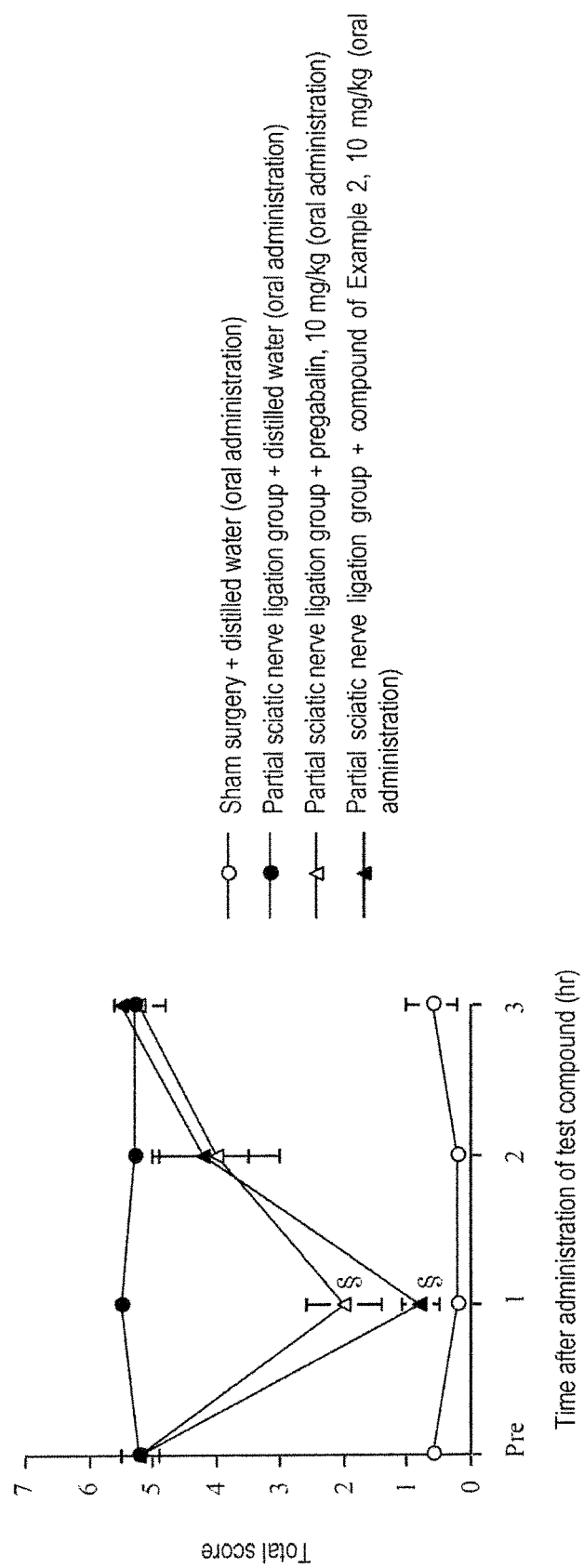
FIG. 2 is a graph showing the effect of the compound of Example 2 in a mouse partial sciatic nerve ligation model (oral administration).
Figure 3:
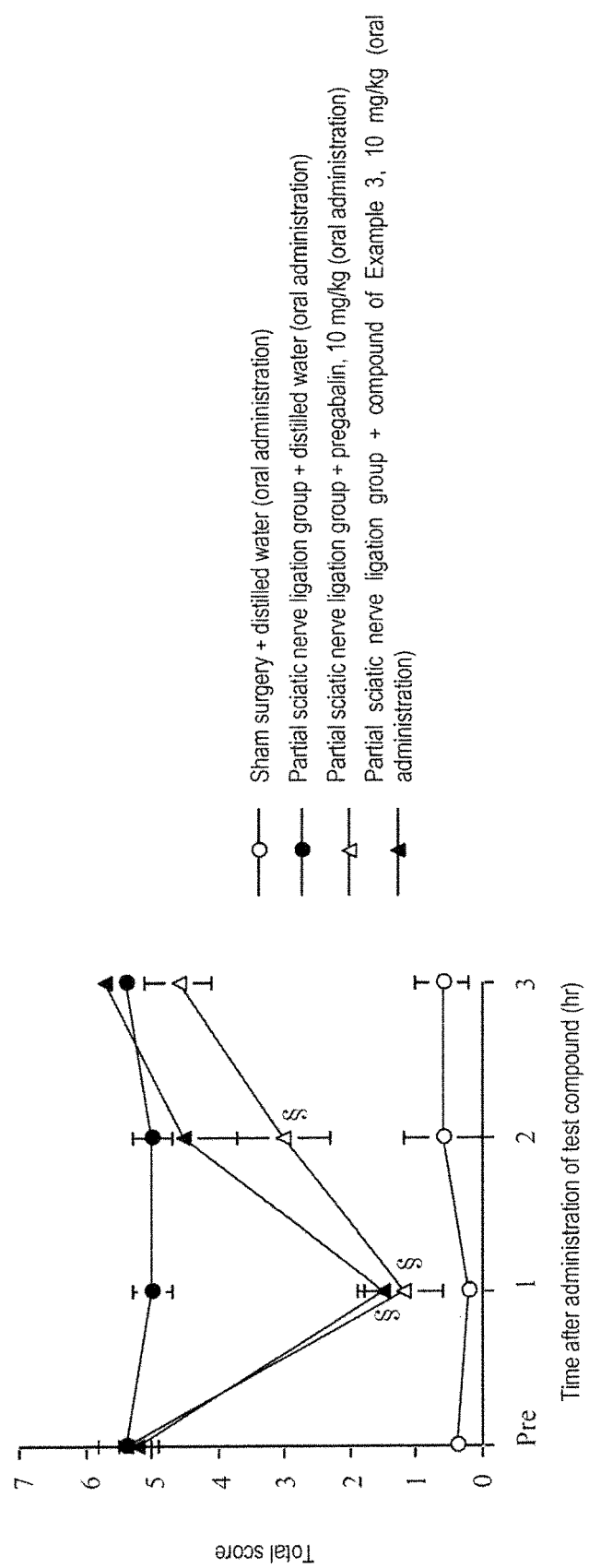
FIG. 3 is a graph showing the effect of the compound of Example 3 in a mouse partial sciatic nerve ligation model (oral administration).
Figure 4:
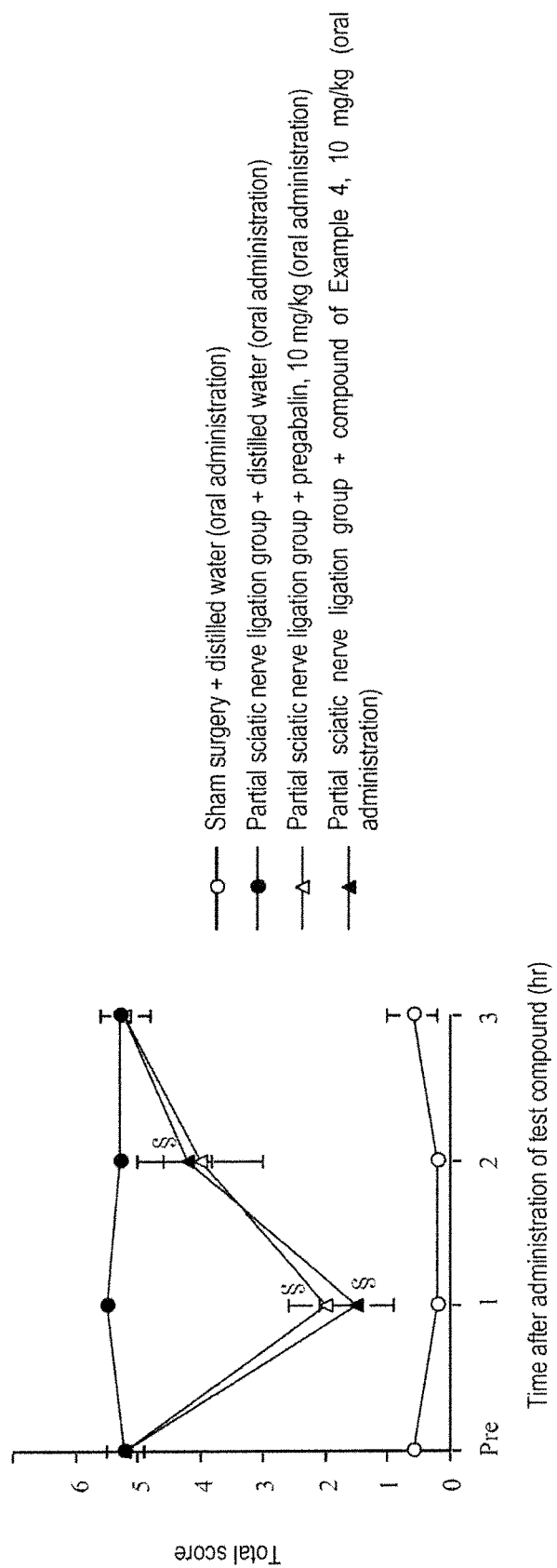
FIG. 4 is a graph showing the effect of the compound of Example 4 in a mouse partial sciatic nerve ligation model (oral administration).
Figure 5:
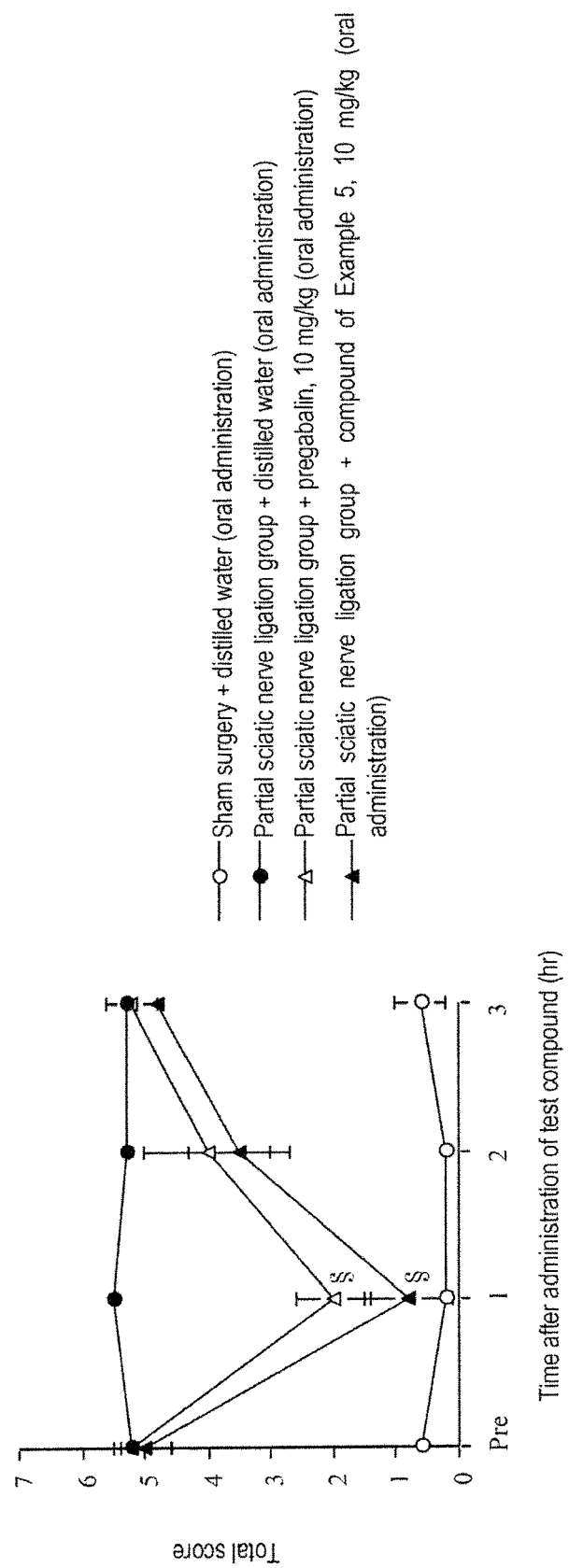
FIG. 5 is a graph showing the effect of the compound of Example 5 in a mouse partial sciatic nerve ligation model (oral administration).
Figure 6:
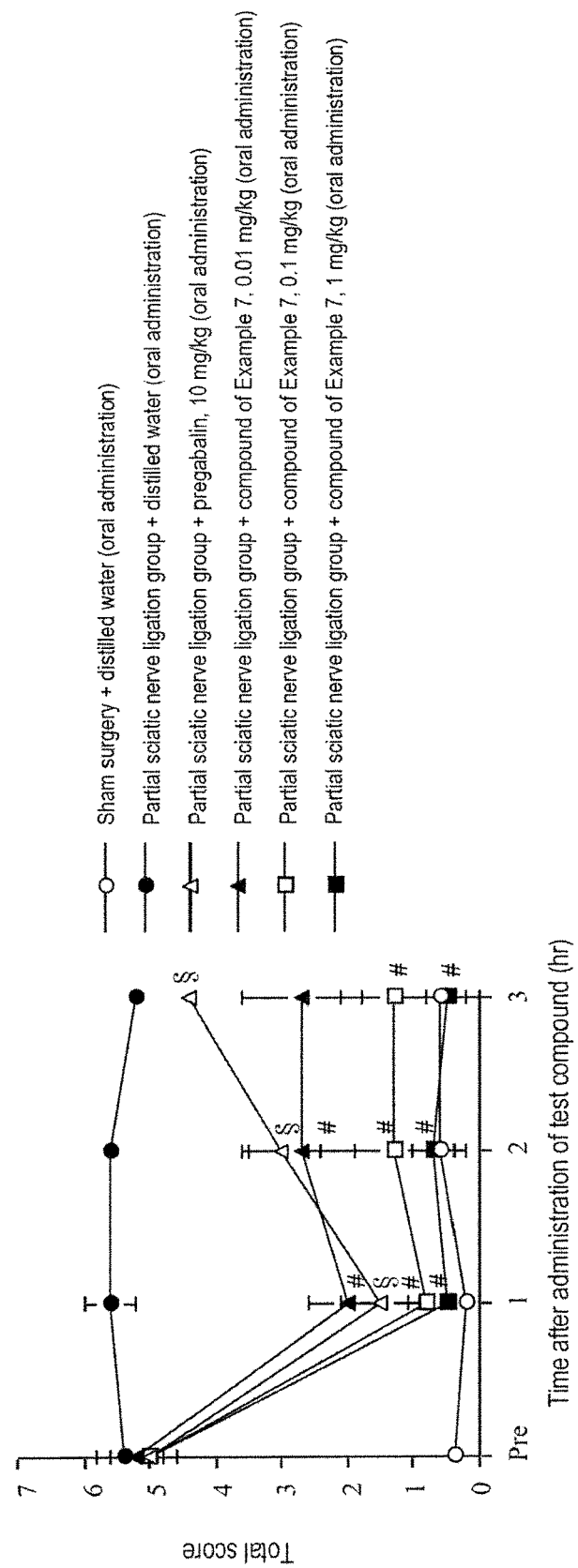
FIG. 6 is a graph showing the effect of the compound of Example 7 in a mouse partial sciatic nerve ligation model (oral administration).
Figure 7:
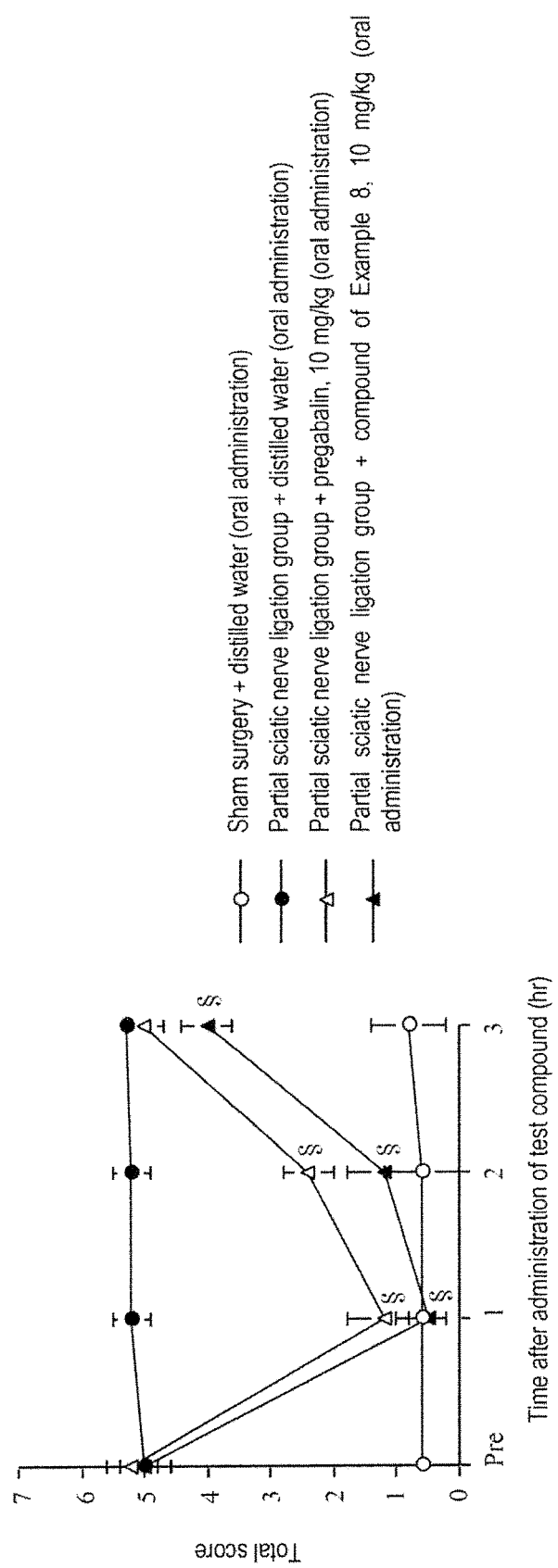
FIG. 7 is a graph showing the effect of the compound of Example 8 in a mouse partial sciatic nerve ligation model (oral administration).
Figure 8:
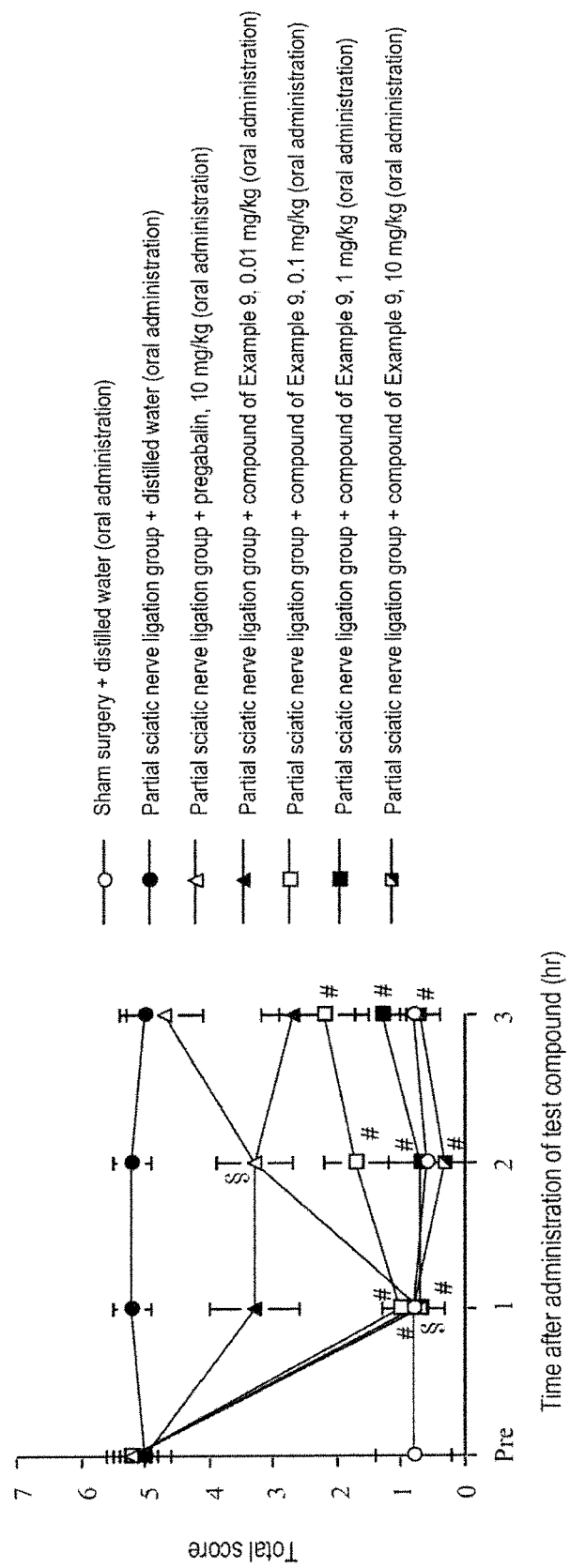
FIG. 8 is a graph showing the effect of the compound of Example 9 in a mouse partial sciatic nerve ligation model (oral administration).
Figure 9:
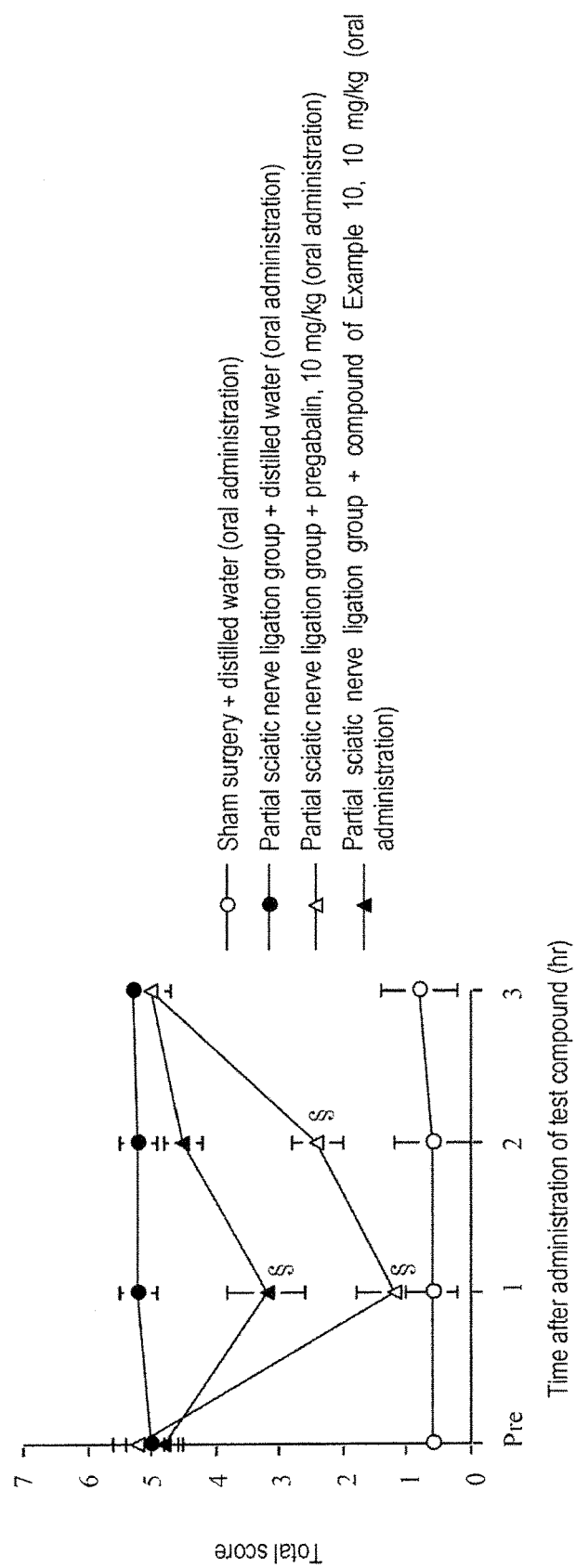
FIG. 9 is a graph showing the effect of the compound of Example 10 in a mouse partial sciatic nerve ligation model (oral administration).
Figure 10:
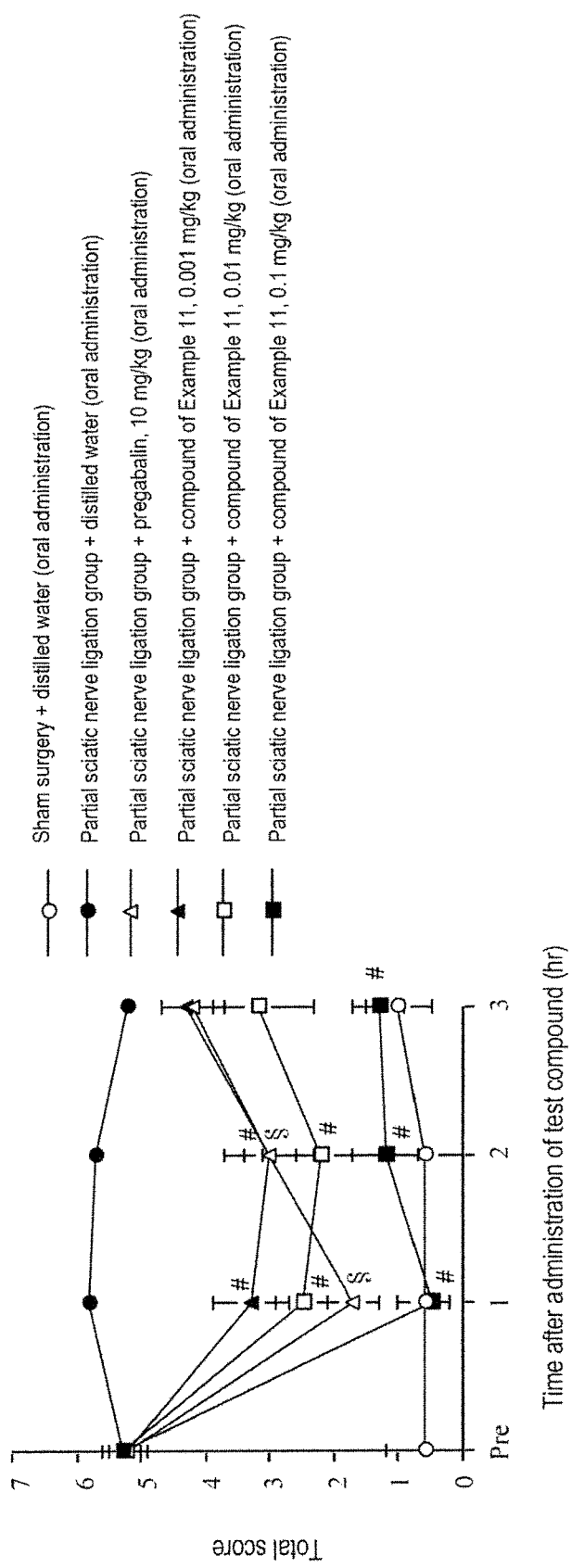
FIG. 10 is a graph showing the effect of the compound of Example 11 in a mouse partial sciatic nerve ligation model (oral administration).
Figure 11:
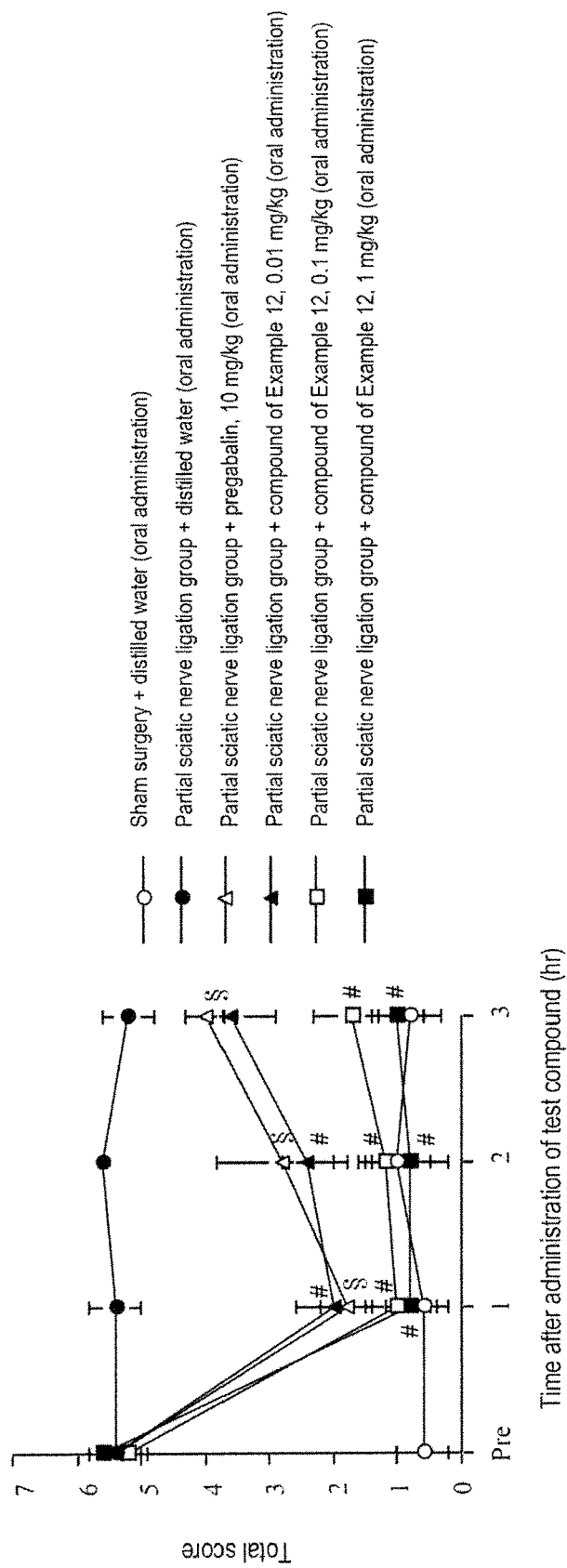
FIG. 11 is a graph showing the effect of the compound of Example 12 in a mouse partial sciatic nerve ligation model (oral administration).
Figure 12:
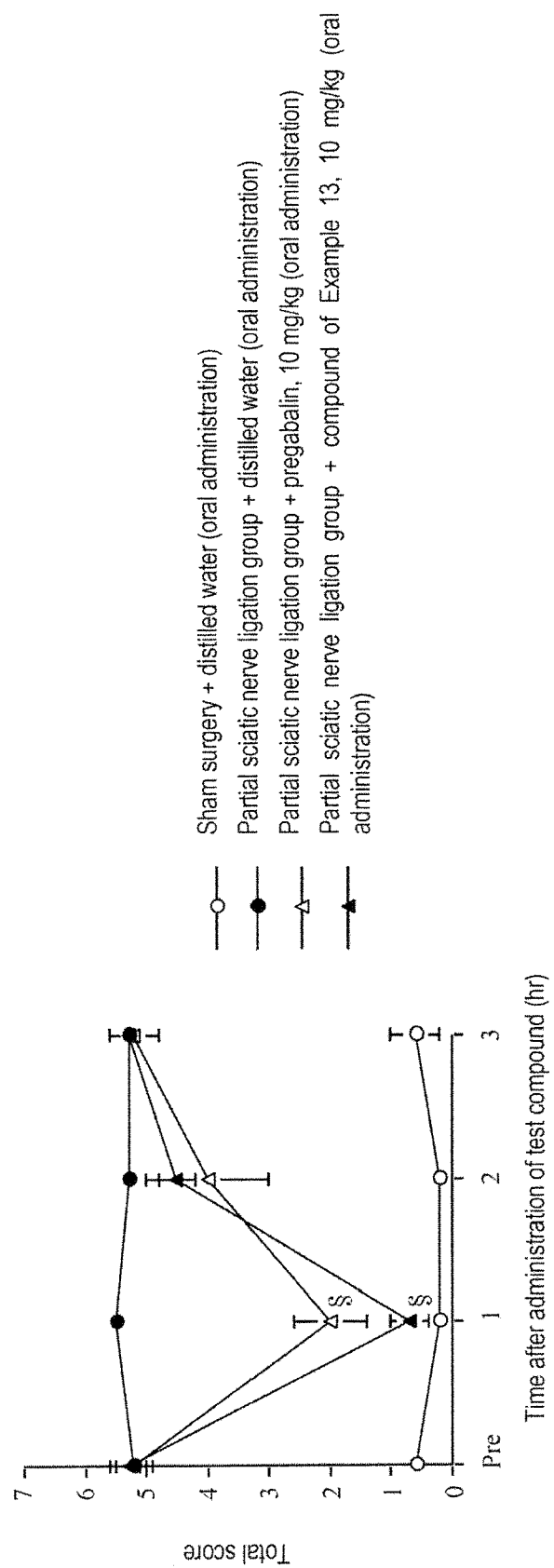
FIG. 12 is a graph showing the effect of the compound of Example 13 in a mouse partial sciatic nerve ligation model (oral administration).

The following terms used in the specification are, unless otherwise specified, defined as follows.

It is characterized in that the cyclic amine derivative is represented by general formula (I):

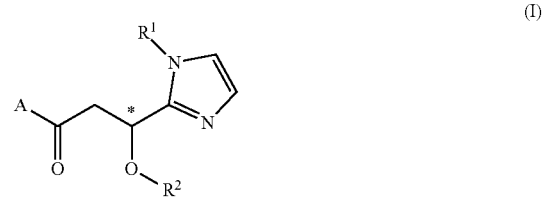

wherein carbon marked with * is an asymmetric carbon, and A represents a group represented by general formulae (IIa), (IIb) or (IIc),

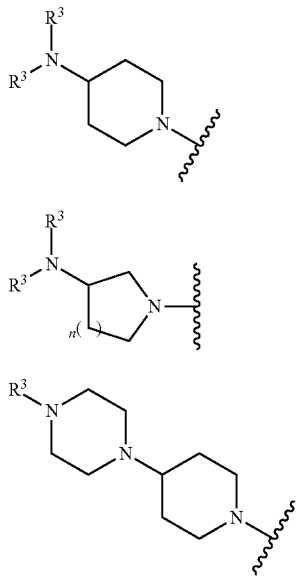

wherein $R^1$ represents a methyl group or an ethyl group optionally substituted with a halogen atom, $R^2$ represents a hydrogen atom or an alkylcarbonyl group having 2 to 5 carbon atoms, each $R^3$ independently represents a methyl group or an ethyl group, and n represents 1 or 2.

In the above cyclic amine derivative, it is preferable that A is a group represented by general formula (IIa); and $R^1$ is preferably a methyl group or an ethyl group optionally substituted with a fluorine atom and more preferably a methyl group, an ethyl group, a difluoromethyl group or a 2,2,2-trifluoroethyl group.

In the above cyclic amine derivative, it is preferable that A is a group represented by general formulae (IIb) or (IIc), in which $R^1$ is preferably a methyl group or an ethyl group optionally substituted with a fluorine atom; and more preferably a methyl group, an ethyl group, a difluoromethyl group or a 2,2,2-trifluoroethyl group.

In the above cyclic amine derivative, it is preferable that A is a group represented by general formula (IIa) and that the stereochemical configuration of the asymmetric carbon marked with * is S, in which $R^1$ is preferably a methyl group or an ethyl group optionally substituted with a fluorine atom; and more preferably a methyl group, an ethyl group, a difluoromethyl group or a 2,2,2-trifluoroethyl group.

In an example of the above cyclic amine derivative, A is a group represented by general formula (IIa), $R^1$ represents a methyl group or an ethyl group optionally substituted with a fluorine atom, $R^2$ represents a hydrogen atom or an alkylcarbonyl group having 2 to 5 carbon atoms and each $R^3$ independently represents a methyl group or an ethyl group. In this example, it is preferable that the stereochemical configuration of the asymmetric carbon marked with * is S.

In an example of the above cyclic amine derivative, A is a group represented by general formula (IIa), $R^1$ represents a methyl group, an ethyl group, a difluoromethyl group or a 2,2,2-trifluoroethyl group, $R^2$ represents a hydrogen atom or an alkylcarbonyl group having 2 to 5 carbon atoms and each $R^3$ independently represents a methyl group or an ethyl group. In this example, it is preferable that the stereochemical configuration of the asymmetric carbon marked with * is S.

In an example of the above cyclic amine derivative, A is a group represented by general formula (IIa), $R^1$ represents a methyl group or a 2,2,2-trifluoroethyl group, $R^2$ represents a hydrogen atom or an alkylcarbonyl group having 2 carbon atoms and $R^3$ represents a methyl group. In this example, it is preferable that the stereochemical configuration of the asymmetric carbon marked with * is S.

In an example of the above cyclic amine derivative, A is a group represented by general formula (IIb), $R^1$ represents a methyl group or an ethyl group optionally substituted with a fluorine atom, $R^2$ represents a hydrogen atom or an alkylcarbonyl group having 2 to 5 carbon atoms, each $R^3$ independently represents a methyl group or an ethyl group, and n represents 1 or 2. In this example, it is preferable that the stereochemical configuration of the asymmetric carbon marked with * is S.

In an example of the above cyclic amine derivative, A is a group represented by general formula (IIb), $R^1$ represents a methyl group, an ethyl group, a difluoromethyl group or a 2,2,2-trifluoroethyl group, $R^2$ represents a hydrogen atom or an alkylcarbonyl group having 2 to 5 carbon atoms, each $R^3$ independently represents a methyl group or an ethyl group, and n represents 1 or 2. In this example, it is preferable that the stereochemical configuration of the asymmetric carbon marked with * is S.

In an example of the above cyclic amine derivative, A is a group represented by general formula (IIb), $R^1$ represents a methyl group or a 2,2,2-trifluoroethyl group, $R^2$ represents a hydrogen atom or an alkylcarbonyl group having 2 carbon atoms, $R^3$ represents a methyl group, and n represents 1 or 2. In this example, it is preferable that the stereochemical configuration of the asymmetric carbon marked with * is S.

In an example of the above cyclic amine derivative, A is a group represented by general formula (IIc), $R^1$ represents a methyl group or an ethyl group optionally substituted with a fluorine atom, $R^2$ represents a hydrogen atom or an alkylcarbonyl group having 2 to 5 carbon atoms and $R^3$ represents a methyl group or an ethyl group. In this example, it is preferable that the stereochemical configuration of the asymmetric carbon marked with * is S.

In an example of the above cyclic amine derivative, A is a group represented by general formula (IIc), $R^1$ represents a methyl group, an ethyl group, a difluoromethyl group or a 2,2,2-trifluoroethyl group, $R^2$ represents a hydrogen atom or an alkylcarbonyl group having 2 to 5 carbon atoms and $R^3$ represents a methyl group or an ethyl group. In this example, it is preferable that the stereochemical configuration of the asymmetric carbon marked with * is S.

In an example of the above cyclic amine derivative, A is a group represented by general formula (IIc), $R^1$ represents a methyl group or a 2,2,2-trifluoroethyl group, $R^2$ represents a hydrogen atom or an alkylcarbonyl group having 2 carbon atoms and $R^3$ represents a methyl group. In this example, it is preferable that the stereochemical configuration of the asymmetric carbon marked with * is S.

The "halogen atom" refers to a fluorine atom, a chlorine atom, a bromine atom or an iodine atom.

The "methyl group or an ethyl group optionally substituted with a halogen atom" refers to a methyl group or an ethyl group in which hydrogen atoms are each independently and optionally substituted with a halogen atom as mentioned above. For example, a methyl group or an ethyl group, or a difluoromethyl group, a 2-fluoroethyl group, a 2-chloroethyl group, a 2,2-difluoroethyl group or a 2,2,2-trifluoroethyl group can be mentioned.

The "alkylcarbonyl group having 2 to 5 carbon atoms" refers to a group obtained by binding a linear, branched or cyclic saturated hydrocarbon group having 1 to 4 carbon atoms to a carbonyl group. For example, an acetyl group, a n-propionyl group, a n-butyryl group, an isobutyryl group or a valeryl group can be mentioned.

Specific examples of a preferable compound as a cyclic amine derivative represented by general formula (I) (hereinafter referred to as a cyclic amine derivative (I)) will be shown in Tables 1-1 and 1-2. However, the derivatives are not limited to these.

TABLE 1-1-continued
Structural formula
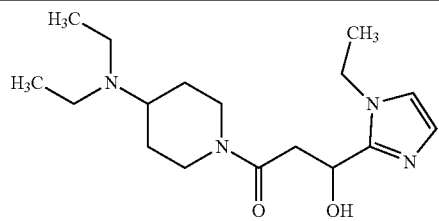
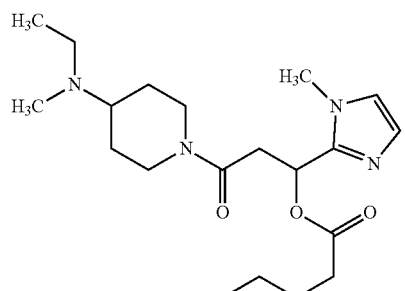
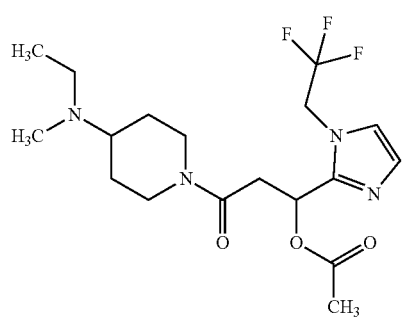
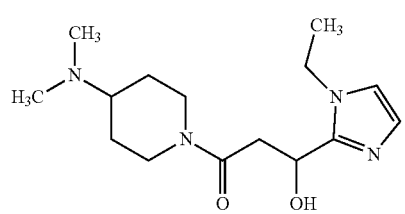 [SMILES: CCn1ccnc1C(O)CC(=O)N1CCC(N(C)C)CC1]
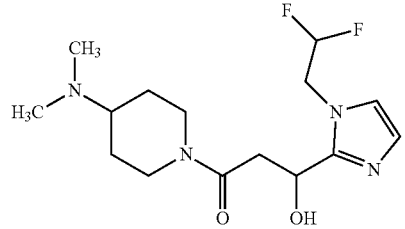 [SMILES: CN(C)C1CCN(C(=O)CC(O)c2nccn2CC(F)F)CC1]
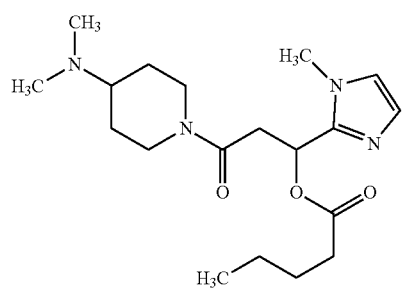 [SMILES: CCCCC(=O)OC(CC(=O)N1CCC(N(C)C)CC1)c1nccn1C]
TABLE 1-1-continued
Structural formula
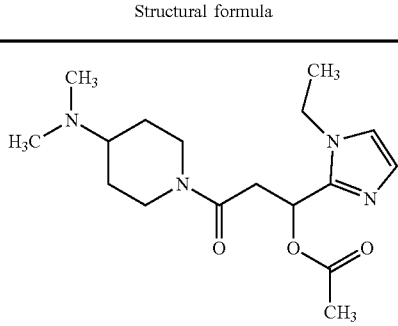
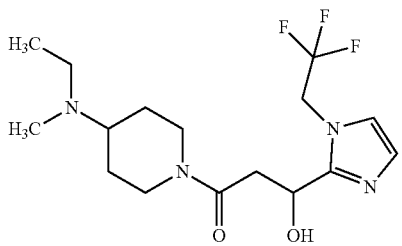 [SMILES: CCN(C)C1CCN(C(=O)CC(O)c2nccn2CC(F)(F)F)CC1]
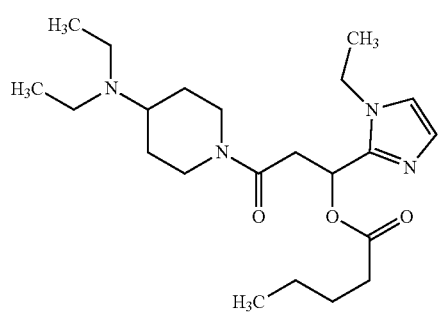
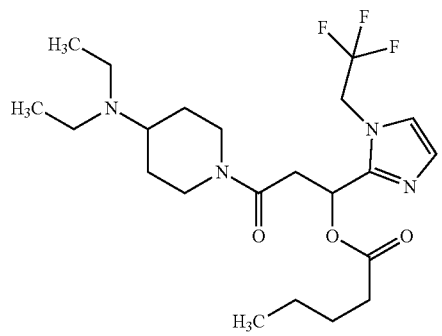 [SMILES: CCCCC(=O)OC(CC(=O)N1CCC(N(CC)CC)CC1)c1nccn1CC(F)(F)F]
TABLE 1-2
Structural formula
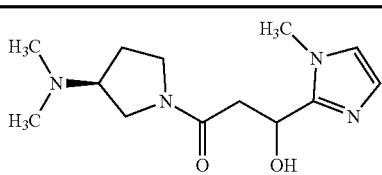

TABLE 1-2-continued

Structural formula

TABLE 1-2-continued

Structural formula

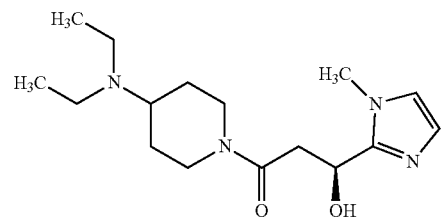 [SMILES: CCN(CC)C1CCN(C(=O)C[C@H](O)c2nccn2C)CC1]

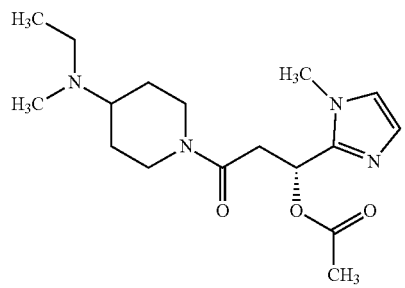 [SMILES: CCN(C)C1CCN(C(=O)C[C@@H](OC(C)=O)c2nccn2C)CC1]

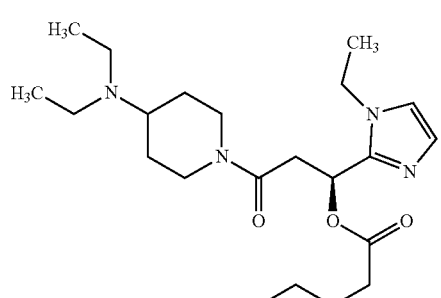

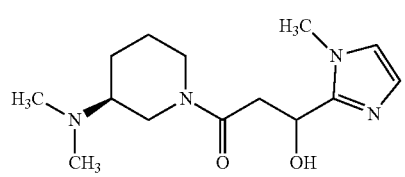 [SMILES: CN(C)[C@H]1CCCN(C(=O)CC(O)c2nccn2C)C1]

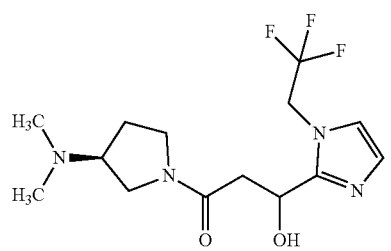 [SMILES: CN(C)[C@H]1CCN(C(=O)CC(O)c2nccn2CC(F)(F)F)C1]

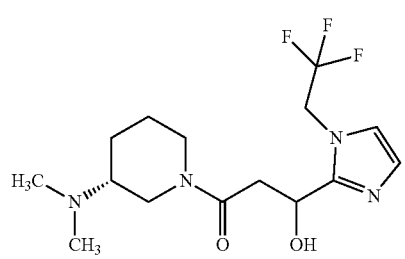 [SMILES: CN(C)[C@@H]1CCCN(C(=O)CC(O)c2nccn2CC(F)(F)F)C1]

TABLE 1-2-continued

Structural formula

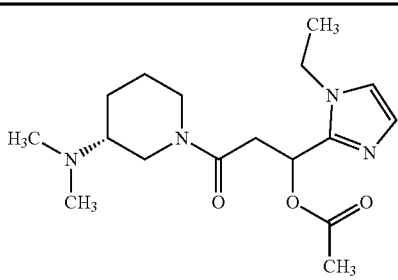

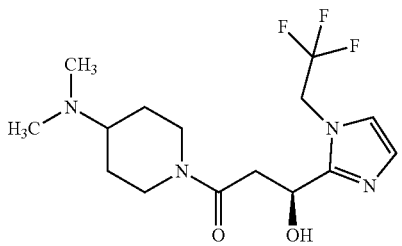 [SMILES: CN(C)C1CCN(C(=O)C[C@H](O)c2nccn2CC(F)(F)F)CC1]

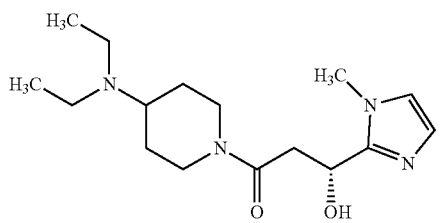

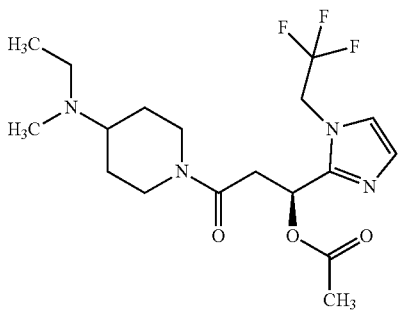 [SMILES: CCN(C)C1CCN(C(=O)C[C@H](OC(C)=O)c2nccn2CC(F)(F)F)CC1]

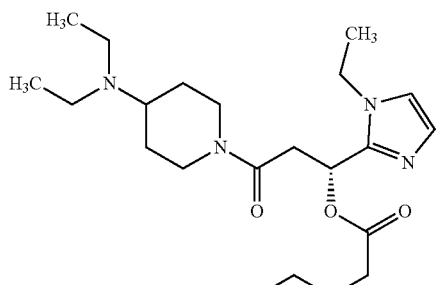

When the cyclic amine derivative (I) has isomers such as enantiomers and stereoisomers, any one of isomers and mixtures of them are included in the cyclic amine derivative (I). In addition, when conformational isomers are sometimes formed, such isomers and mixtures of these are included in the cyclic amine derivative (I). A desired isomer can be obtained by a known method or a similar method thereto. For example, when an enantiomer of a cyclic amine derivative (I) is present, the enantiomer separated from the cyclic amine derivative (I) is included in the cyclic amine derivative (I).

A desired enantiomer can be obtained by a known means (for example, an optically active synthetic intermediate is used or a final-product racemic mixture is subjected to a known method or a similar method thereto (for example, optical resolution)).

A prodrug or a pharmacologically acceptable salt of a cyclic amine derivative (I) is also included. The prodrug of a cyclic amine derivative (I) refers to a compound, which is enzymatically or chemically converted to the cyclic amine derivative (I) in vivo. The active form of a prodrug of a cyclic amine derivative (I) is the cyclic amine derivative (I). However, a prodrug of the cyclic amine derivative (I) itself may have activity.

As the prodrug of a cyclic amine derivative (I), for example, a compound obtained by alkylation, phosphorylation or boration of a hydroxyl group of the cyclic amine derivative (I) can be mentioned. These compounds can be each synthesized from a cyclic amine derivative (I) in accordance with a known method.

A prodrug of a cyclic amine derivative (I) may be converted into the cyclic amine derivative (I) in physiological conditions described in known literatures ("Development of pharmaceutical products," Hirokawa-Shoten Ltd., vol. 7, p. 163 to 198, 1990, and Progress in Medicine, vol. 5, p. 2157 to 2161, 1985).

A cyclic amine derivative (I) may be labeled with an isotope. Examples of the radioisotope for use in labeling include $^2$H, $^3$H, $^{13}$C, $^{14}$C, $^{15}$N, $^{15}$O, $^{18}$O and/or $^{125}$I.

As the pharmacologically acceptable salt of a cyclic amine derivative (I), for example, an inorganic salt such as a hydrochloride, a sulfate, a phosphate or a hydrobromide; or an organic salt such as an oxalate, a malonate, a citrate, a fumarate, a lactate, a malate, a succinate, a tartrate, an acetate, a trifluoroacetate, a maleate, a gluconate, a benzoate, a salicylate, a xinafoate, a pamoate, an ascorbate, an adipate, a methanesulfonate, a p-toluenesulfonate or a cinnamate. These salts may be present in the form of a hydrate, a solvate or a crystalline polymorph.

A cyclic amine derivative (I) can be synthesized by the production methods that will be described below. The cyclic amine derivatives (I) obtained by the following production methods each can be isolated/purified by a known means (for example, solvent extraction, recrystallization and/or chromatography) and converted into desired salts by known methods or a similar method thereto. When a cyclic amine derivative (I) is obtained in the form of a salt, it can be converted into a cyclic amine derivative (I) or another desired salt by a known method or a similar method thereto.

In individual reactions of the production methods that will be described below, when a starting compound has a hydroxyl group, an amino group or a carboxyl group, a protective group may be introduced in these groups. A desired compound can be obtained by removing the protective group if necessary after the reaction.

As the protective group of a hydroxyl group, for example, a trityl group, an aralkyl group having 7 to 10 carbon atoms (e.g., benzyl group) or a substituted silyl group (e.g., trimethylsilyl group, triethylsilyl group or tert-butyldimethylsilyl group) can be mentioned.

As the protective group of an amino group, for example, an alkylcarbonyl group having 2 to 6 carbon atoms (for example, acetyl group), a benzoyl group, an alkyloxycarbonyl group having 2 to 8 carbon atoms (for example, tert-butoxycarbonyl group or benzyloxycarbonyl group), an aralkyl group having 7 to 10 carbon atoms (for example, benzyl group) or a phthaloyl group can be mentioned.

As the protective group of a carboxyl group, for example, an alkyl group having 1 to 6 carbon atoms (e.g., methyl group, ethyl group or tert-butyl group) or an aralkyl group having 7 to 10 carbon atoms (for example, benzyl group) can be mentioned.

Removal of a protective group, which varies depending upon the type of protective group, can be performed in accordance with a known method (for example, Greene, T. W., "Greene's Protective Groups in Organic Synthesis," Wiley-Interscience) or a similar method thereto.

1. Production of Compound (Ia)

1-1. Production Method for Compound (Ia-a)

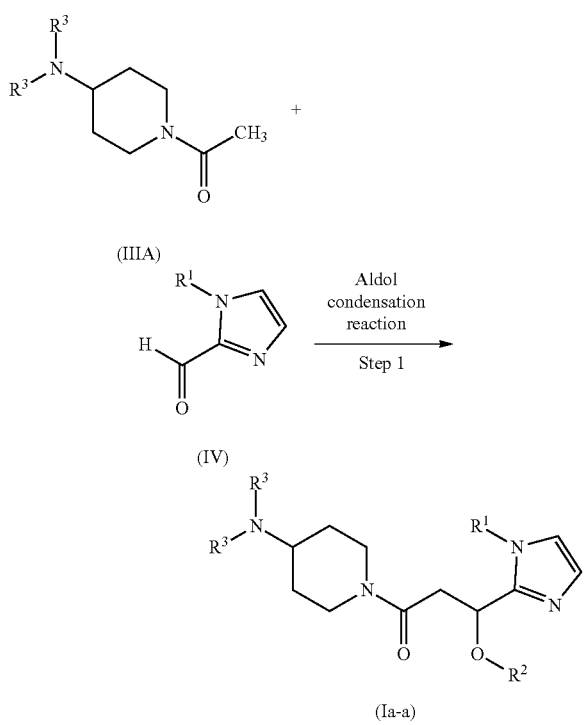

wherein individual reference symbols are the same as defined above.

Step 1

A compound (Ia-a), which is a cyclic amine derivative (I) wherein A is a group represented by general formula (IIa) can be obtained, for example, by the aldol condensation reaction of a compound (IIIA) and a compound (IV) in the presence of a base.

As the compound (IIIA) and compound (IV) to be used in the aldol condensation reaction, commercially available compounds can be directly used. However, they can be synthesized, for example, in accordance with the production methods that will be described below.

As the base to be used in the aldol condensation reaction, for example, lithium diisopropylamide, potassium tert-butoxide, sodium hydride, phenyl lithium or tert-butyl lithium can be mentioned.

The amount of the base to be used in the aldol condensation reaction is preferably 0.5 to 10 moles relative to 1 mol of a compound (IIIA) and more preferably 0.8 to 5 moles.

The amount of the compound (IV) to be used in the aldol condensation reaction is preferably 0.5 to 3 moles relative to 1 mole of a compound (IIIA) and more preferably 0.8 to 1.5 moles.

The aldol condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixed solvent of these may be used.

In the aldol condensation reaction, the reaction temperature is preferably −78° C. to 100° C. and more preferably −78° C. to 50° C.

In the aldol condensation reaction, the reaction time, which varies depending upon the reaction conditions, is preferably 5 minutes to 48 hours, and more preferably 30 minutes to 24 hours.

wherein $R^{2a}$ represents a hydrogen atom, $R^{2b}$ represents an alkylcarbonyl group having 2 to 5 carbon atoms, and other reference symbols are the same as defined above.

Step 2

A compound (Ia-b), which is a cyclic amine derivative (I) wherein A is a group represented by general formula (IIa) and $R^2$ is a hydrogen atom, can be obtained, for example, by the aldol condensation reaction between the compound (IIIA) and the compound (IV) in the presence of a base.

As the compound (IIIA) and compound (IV) to be used in the aldol condensation reaction, commercially available compounds can be directly used. However, they can be synthesized, for example, in accordance with the production methods that will be described below.

As the base to be used in the aldol condensation reaction, for example, lithium diisopropylamide, potassium tert-butoxide, sodium hydride, phenyl lithium or tert-butyl lithium can be mentioned.

The amount of the base to be used in the aldol condensation reaction is preferably 0.5 to 10 moles relative to 1 mole of a compound (IIIA) and more preferably 0.8 to 5 moles.

The amount of the compound (IV) to be used in the aldol condensation reaction is preferably 0.5 to 3 moles relative to 1 mole of a compound (IIIA) and more preferably 0.8 to 1.5 moles.

1-2. Production Method for Compounds (Ia-b) and (Ia-c)

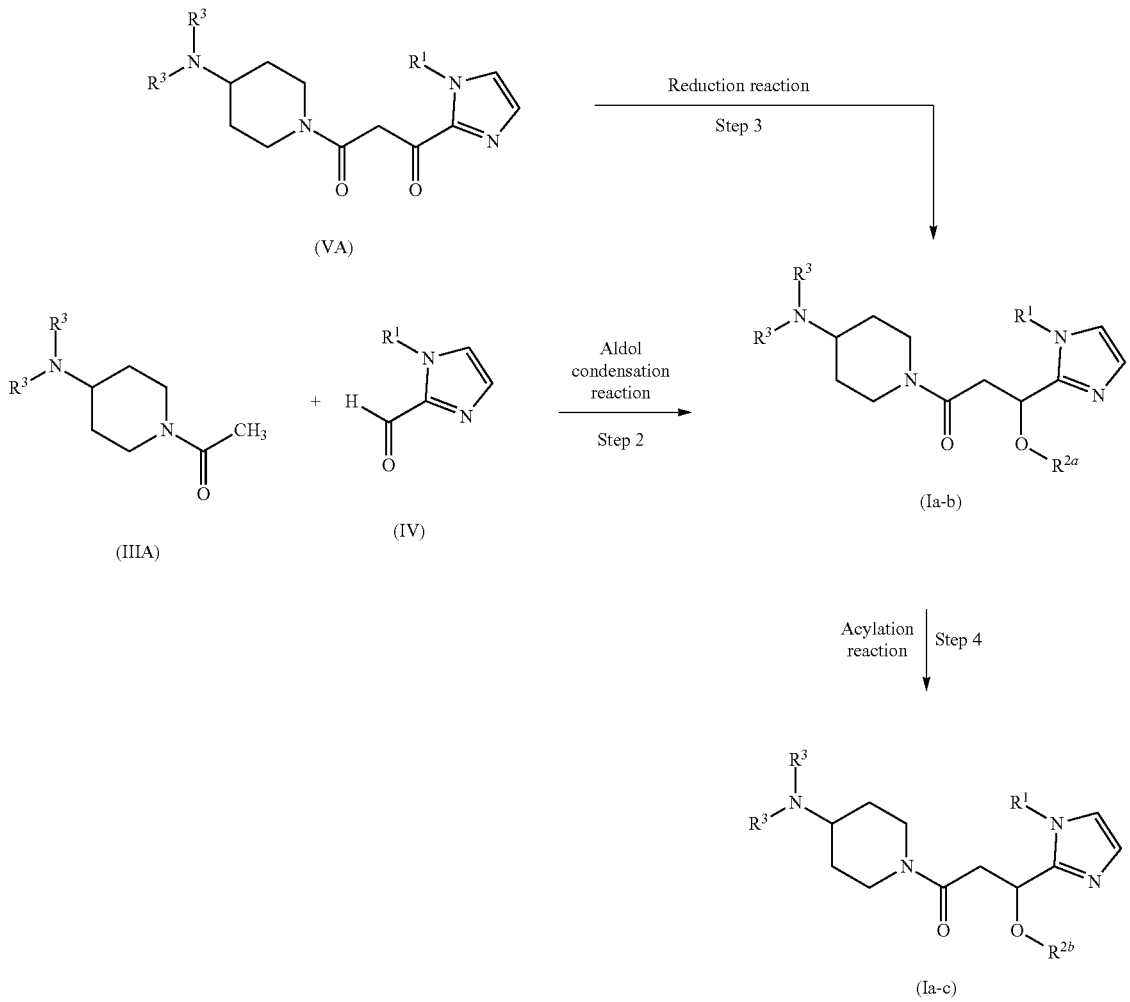

The aldol condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixed solvent of these may be used.

The reaction temperature of the aldol condensation reaction is preferably −78° C. to 100° C. and more preferably −78° C. to 50° C.

The reaction time of the aldol condensation reaction, which varies depending upon the reaction conditions, is preferably 5 minutes to 48 hours and more preferably 30 minutes to 24 hours.

Step 3

A compound (Ia-b), which is a cyclic amine derivative (I) wherein A is a group represented by general formula (IIa) and $R^2$ is a hydrogen atom, can be obtained by reduction reaction of a compound (VA).

The compound (VA) to be used in the reduction reaction can be synthesized, for example, in accordance with the production method that will be described below.

As the reducing agent to be used in the reduction reaction, for example, lithium borohydride, sodium borohydride, diisobutylaluminum hydride, lithium aluminum hydride, lithium triethyl hydride, sodium bis(2-methoxyethoxy)aluminum hydride or a borane complex can be mentioned.

The amount of the reducing agent to be used in the reduction reaction is preferably 0.5 to 10 moles relative to 1 mole of the compound (VA) and more preferably 0.8 to 5 moles.

The reduction reaction is generally carried out in a solvent. A solvent that does not inhibit the reaction is appropriately selected. As the solvent, for example, a hydrocarbon such as octane, hexane, benzene or toluene; an ether such as tetrahydrofuran, 1,4-dioxane, ethylene glycol dimethyl ether or diethyl ether; or an alcohol such as methanol, ethanol or 2-propanol, can be mentioned. A mixed solvent of these may be used.

In the reduction reaction, the reaction temperature is preferably −78° C. to 150° C. and more preferably −78° C. to 100° C.

In the reduction reaction, the reaction time, which varies depending upon the reaction conditions, is preferably 5 minutes to 72 hours, and more preferably 30 minutes to 24 hours.

Step 4

A compound (Ia-c), which is a cyclic amine derivative (I) wherein A is a group represented by general formula (IIa) and R2 is an alkylcarbonyl group having 2 to 5 carbon atoms, can be obtained, for example, by the acylation reaction of a compound (Ia-b) using an acylating agent such as a halide of a carboxylic acid having 2 to 5 carbon atoms or an acid anhydride of a carboxylic acid having 2 to 5 carbon atoms in the presence of a base.

In the acylation reaction, a compound (Ia-b) and a salt thereof can be used. As the salt herein, for example, the same salt as a pharmacologically acceptable salt as mentioned above can be mentioned.

As the base to be used in the acylation reaction, for example, pyridine, triethylamine, diisopropylethylamine or N,N-dimethylaminopyridine can be mentioned.

The amount of the base to be used in the acylation reaction is preferably 0.5 to 10 moles relative to 1 mole of a compound (Ia-b) and more preferably 0.8 to 5 moles.

As the acylating agent to be used in the acylation reaction, a commercially available compound can be directly used.

The amount of the acylating agent to be used in the acylation reaction is preferably 0.5 to 10 moles relative to 1 mole of the compound (Ia-b) and more preferably 0.8 to 5 moles.

The acylation reaction is generally performed in a solvent. A solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixed solvent of these may be used. When an aromatic amine such as pyridine is selected as the solvent, an acylation reaction can be performed in the absence of a base.

The reaction temperature of the acylation reaction is preferably −40° C. to 100° C. and more preferably −20° C. to 80° C.

The reaction time of the acylation reaction, which varies depending upon the reaction conditions, is preferably 5 minutes to 72 hours and more preferably 30 minutes to 24 hours.

1-3. Salt Formation Steps of Compounds (Ia-a), (Ia-b) and (Ia-c)

Pharmacologically acceptable salts of compounds (Ia-a), (Ia-b) and (Ia-c) can be obtained, for example, by salt formation reactions of the compound (Ia-a), (Ia-b) or (Ia-c) with an acid.

As the acid to be used for a salt formation reaction, for example, an inorganic acid such as hydrochloric acid, sulfuric acid, phosphoric acid or hydrobromic acid; or an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoic acid, pamoic acid, ascorbic acid, adipic acid, methanesulfonic acid, p-toluenesulfonic acid or cinnamic acid can be mentioned.

A salt formation reaction is generally performed in a solvent. A solvent that does not inhibit the reaction is appropriately selected. As the solvent, for example, an aliphatic alcohol such as methanol, ethanol or 2-propanol; an ether such as diethyl ether, tetrahydrofuran, 1,4-dioxane or ethylene glycol dimethyl ether; an amide such as N,N-dimethylformamide or N-methylpyrrolidone; a sulfoxide such as dimethyl sulfoxide; an aliphatic nitrile such as acetonitrile or propionitrile; a ketone such as acetone or 2-butanone; an ester such as ethyl acetate, methyl acetate or n-butyl acetate; or water can be mentioned. A mixture of these solvents may be used.

2. Production of Compound (IIIA)

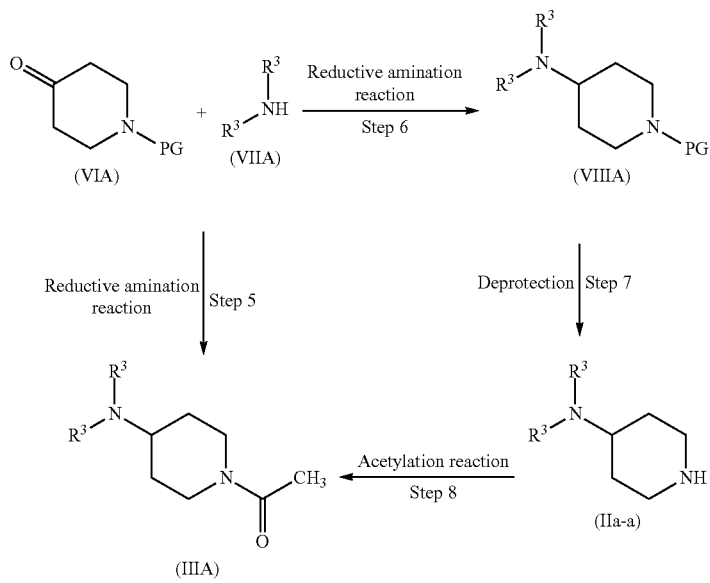

wherein PG represents a protective group and other reference symbols are the same as defined above.

Step 5

A compound (IIIA) can be obtained by the reductive amination reaction between a compound (VIA) in which PG is an acetyl group and a compound (VIIA).

As the compound (VIA) and compound (VIIA) to be used in the reductive amination reaction, commercially available compounds can be directly used.

The reductive amination reaction can be performed by a known method (for example, Journal of Organic Chemistry, vol. 68, p. 770-779, 2003) or a similar method thereto.

Step 6

A compound (VIIIA) can be obtained by the reductive amination reaction between a compound (VIA) and a compound (VIIA).

As the compound (VIA) and the compound (VIIA) to be used as the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 7

A compound (IIa-a) can be obtained by deprotection of a compound (VIIIA).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

Step 8

A compound (IIIA) can be obtained by the acetylation reaction of a compound (IIa-a).

The acetylation reaction can be performed in accordance with a known method (for example, Greene, T. W., "Greene's Protective Groups in Organic Synthesis," Wiley-Interscience) or a similar method thereto.

3. Production of a Compound (IV)

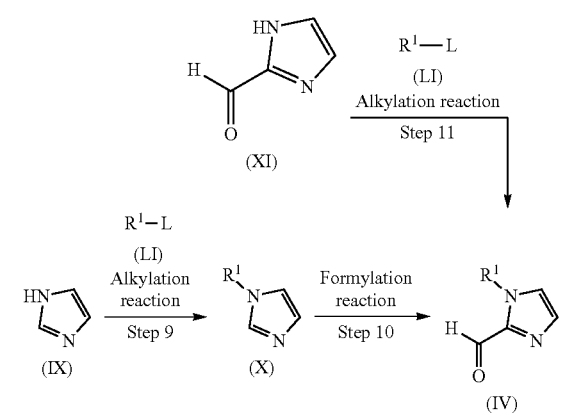

wherein L represents a leaving group and other individual reference symbols are the same as defined above.

Step 9

A compound (X) can be obtained by deprotonation of a compound (IX) with a base, followed by an alkylation reaction with an alkylating reagent (LI).

As the compound (IX) to be used in the alkylation reaction, a commercially available compound can be directly used.

As the base to be used in the alkylation reaction, for example, an alkali metal hydride such as sodium hydride or potassium hydride; or a butyllithium such as n-butyllithium, sec-butyllithium or tert-butyllithium can be mentioned.

The amount of the base to be used in the alkylation reaction is preferably 0.5 to 3 moles relative to 1 mole of a compound (IX) and more preferably 0.8 to 2 moles.

As the alkylating reagent (LI) to be used in the alkylation reaction, a commercially available compound can be directly used.

The amount of the alkylating reagent (LI) to be used in the alkylation reaction is preferably 0.5 to 10 moles relative to 1 mole of a compound (IX) and more preferably 0.8 to 5 moles.

The alkylation reaction is generally performed in a solvent. A solvent that does not inhibit the reaction is appropriately selected. As the solvent, for example, an ether such as tetrahydrofuran or 1,4-dioxane; an amide such as N,N-dimethylformamide or N-methylpyrrolidone; or an aliphatic nitrile such as acetonitrile or propionitrile, can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 10

A compound (IV) can be obtained by deprotonation of a compound (X) with a base, followed by a formylation reaction with a formyl group introducing reagent.

As the compound (X) to be used in the formylation reaction, a commercially available compound can be directly used. However, the compound (X) can be synthesized, for example, in accordance with the above production method.

As the base to be used in the formylation reaction, for example, n-butyllithium, sec-butyllithium or tert-butyllithium can be mentioned.

The amount of base to be used in the formylation reaction is preferably 0.5 to 3 moles relative to 1 mole of a compound (X) and more preferably 0.8 to 2 moles.

As the formyl group introducing reagent to be used in the formylation reaction, for example, N,N-dimethylformamide can be mentioned. As the N,N-dimethylformamide, a commercially available compound can be directly used.

The amount of the formyl group introducing reagent to be used in the formylation reaction is preferably 0.5 to 3 moles relative to 1 mole of a compound (X) and more preferably 0.8 to 2 moles.

The formylation reaction is generally performed in a solvent. A solvent that does not inhibit the reaction is appropriately selected. As the solvent, for example, an aliphatic hydrocarbon such as heptane or hexane; or an ether such as tetrahydrofuran, diethyl ether or 1,4-dioxane can be mentioned. A mixture of these solvents may be used.

In the deprotonation of the formylation reaction, the reaction temperature is preferably −100 to 0° C. and more preferably −80 to −20° C. In the formylation of the formylation reaction, the reaction temperature is preferably −20° C. to 150° C. and more preferably 0 to 100° C.

In the formylation reaction, the reaction time, which varies depending upon the reaction conditions, is preferably 5 minutes to 72 hours, and more preferably 30 minutes to 48 hours.

Step 11

A compound (IV) can be obtained by deprotonation of a compound (XI) with a base, followed by an alkylation reaction with an alkylating reagent (LI).

As the compound (XI) to be used in the alkylation reaction, a commercially available compound can be directly used.

As the base to be used in the alkylation reaction, for example, a metal carbonate such as sodium carbonate, potassium carbonate or cesium carbonate; or an alkali metal hydroxide such as sodium hydroxide or potassium hydroxide can be mentioned.

The amount of the base to be used in the alkylation reaction is preferably 0.5 to 3 moles relative to 1 mole of a compound (XI) and more preferably 0.8 to 2 moles.

As the alkylating reagent (LI) to be used in the alkylation reaction, a commercially available compound can be directly used.

The amount of the alkylating reagent (LI) to be used in the alkylation reaction is preferably 0.5 to 3 moles relative to 1 mole of a compound (XI) and more preferably 0.8 to 2 moles.

The alkylation reaction is generally performed in a solvent. A solvent that does not inhibit the reaction is appropriately selected. As the solvent, for example, an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

4. Production of Compound (VA)

4-1. Production Method for Compound (VA)

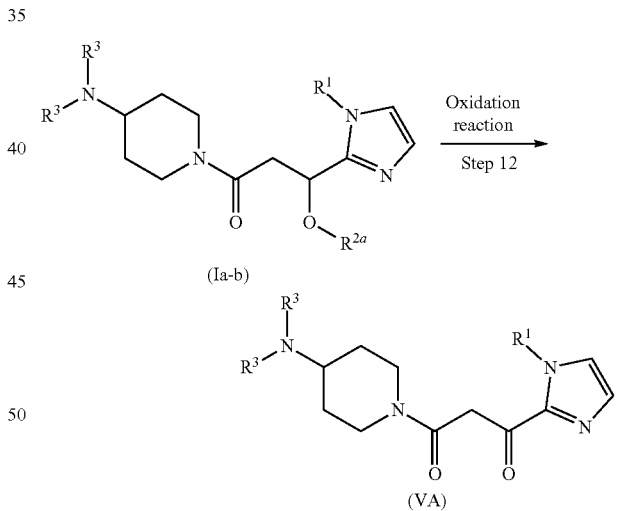

wherein individual reference symbols are the same as defined above.

Step 12

A compound (VA) can be obtained by the oxidation reaction of a compound (Ia-b).

The compound (Ia-b) to be used in the oxidation reaction can be synthesized in accordance with the above production method.

As the oxidant to be used in the oxidation reaction, for example, manganese dioxide, sulfur trioxide-pyridine, activated dimethyl sulfoxide or Dess-Martin reagent can be mentioned.

The amount of the oxidant to be used in the oxidation reaction is preferably 0.5 to 50 moles relative to 1 mole of a compound (Ia-b) and more preferably 0.8 to 35 moles.

The oxidation reaction is generally performed in a solvent. A solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixture of these solvents may be used.

In the oxidation reaction, the reaction temperature is preferably −78° C. to 100° C. and more preferably −78° C. to 40° C.

In the oxidation reaction, the reaction time, which varies depending upon the reaction conditions, is preferably 5 minutes to 72 hours, and more preferably 30 minutes to 48 hours.

4-2. Production Method for Compound (VA)

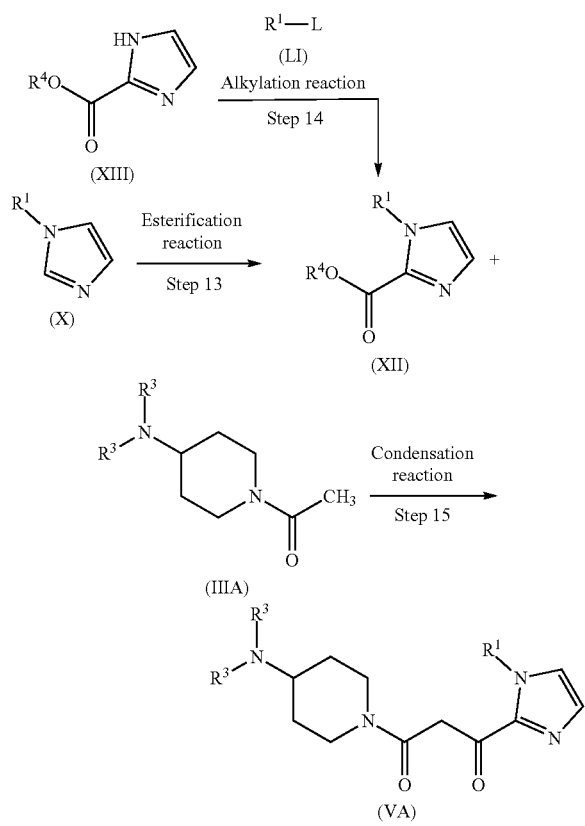

wherein $R^4$ represents an alkyl group having 1 to 6 carbon atoms or an aralkyl group having 7 to 10 carbon atoms; for example, a methyl group, an ethyl group, a n-propyl group, a n-butyl group or a benzyl group can be mentioned; and the other reference symbols are the same as defined above.

Step 13

A compound (XII) can be obtained by an esterification reaction of a compound (X) with an ester group introducing reagent in the presence of a base.

As the compound (X) to be used in the esterification reaction, a commercially available compound can be directly used. However, the compound (X) can be synthesized, for example, in accordance with the above production method.

As the base to be used in the esterification reaction, for example, an aromatic amine such as pyridine or lutidine; or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base used in the esterification reaction is preferably 0.5 to 10 moles relative to 1 mole of the compound (X) and more preferably 0.8 to 5 moles.

As the ester group introducing reagent to be used in the esterification reaction, for example, a halogenated formic acid ester such as ethyl chloroformate can be mentioned. As the ethyl chloroformate, a commercially available compound can be directly used.

The amount of the ester group introducing reagent to be used in the esterification reaction is preferably 0.5 to 3 moles relative to 1 mole of the compound (X) and more preferably 0.8 to 2 moles.

The esterification reaction is generally performed in a solvent. A solvent that does not inhibit the reaction is appropriately selected. As the solvent, for example, an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the esterification reaction, the reaction temperature is preferably −20° C. to 150° C. and more preferably 0 to 100° C.

In the esterification reaction, the reaction time, which varies depending upon the reaction conditions, is preferably 5 minutes to 72 hours, and more preferably 30 minutes to 48 hours.

Step 14

A compound (XII) can be obtained by deprotonation of a compound (XIII) with a base, followed by an alkylation reaction with an alkylating reagent (LI).

As the compound (XIII) to be used in the alkylation reaction, a commercially available compound can be directly used.

As the base to be used in the alkylation reaction, for example, a metal carbonate such as sodium carbonate, potassium carbonate or cesium carbonate; or an alkali metal hydroxide such as sodium hydroxide or potassium hydroxide can be mentioned.

The amount of the base to be used in the alkylation reaction is preferably 0.5 to 3 moles relative to 1 mole of a compound (XIII) and more preferably 0.8 to 2 moles.

As the alkylating reagent (LI) to be used in the alkylation reaction, a commercially available compound can be directly used.

The amount of the alkylating reagent (LI) to be used in the alkylation reaction is preferably 0.5 to 3 moles relative to 1 mole of a compound (XIII) and more preferably 0.8 to 2 moles.

The alkylation reaction is generally performed in a solvent. A solvent that does not inhibit the reaction is appropriately selected. As the solvent, for example, an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 15

A compound (VA) can be obtained by the condensation reaction between a compound (XII) and a compound (IIIA) in the presence of a base.

As the compound (XII) and the compound (IIIA) to be used in the condensation reaction, commercially available compounds can be directly used. However, the compound (XII) and the compound (IIIA) can be synthesized, for example, in accordance with the above production method.

As the base to be used in the condensation reaction, for example, lithium diisopropylamide, potassium tert-butoxide, sodium hydride, phenyl lithium or tert-butyl lithium can be mentioned.

The amount of the base to be used in the condensation reaction is preferably 0.5 to 10 moles relative to 1 mole of a compound (IIIA) and more preferably 0.8 to 5 moles.

The amount of the compound (XII) to be used in the condensation reaction is preferably 0.5 to 3 moles relative to 1 mole of a compound (IIIA) and more preferably 0.8 to 1.5 moles.

The condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixture of these solvents may be used.

In the condensation reaction, the reaction temperature is preferably −78° C. to 100° C. and more preferably −78° C. to 50° C.

In the condensation reaction, the reaction time, which varies depending upon the reaction conditions, is preferably 5 minutes to 48 hours, and more preferably 30 minutes to 24 hours.

4-3. Production Methods for Compound (VA)

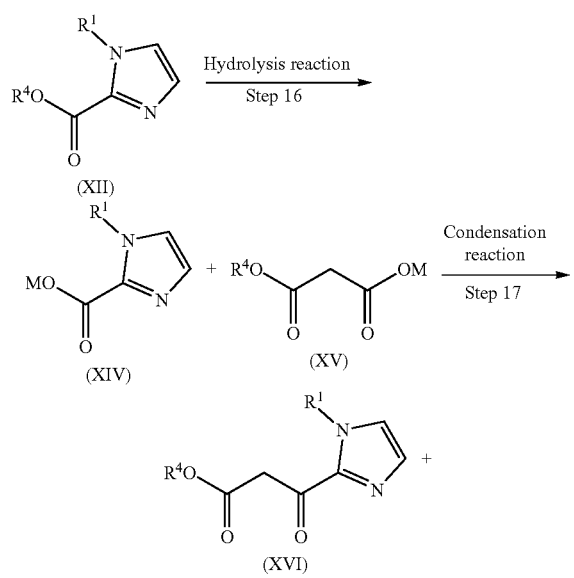

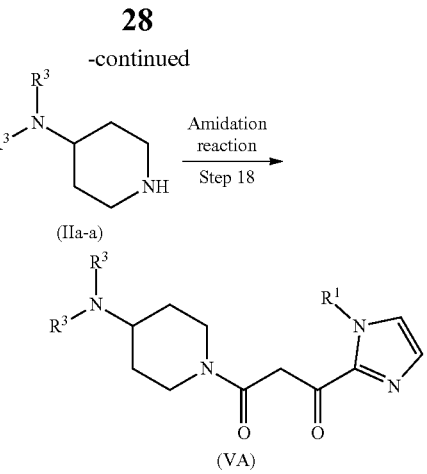

wherein M represents a hydrogen atom or an alkali metal; as the alkali metal, for example, lithium or sodium can be mentioned; and the other reference symbols are the same as defined above.

Step 16

A compound (XIV) can be obtained by the hydrolysis reaction of a compound (XII).

As the compound (XII) to be used in the hydrolysis reaction, a commercially available compound can be directly used. However, the compound (XII) can be synthesized, for example, in accordance with the above production method.

As the base to be used in the hydrolysis reaction, for example, lithium hydroxide, potassium hydroxide or sodium hydroxide can be mentioned.

The amount of the base to be used in the hydrolysis reaction is preferably 0.5 to 3 moles relative to 1 mole of a compound (XII) and more preferably 0.8 to 2 moles.

The hydrolysis reaction is generally performed in a solvent. A solvent that does not inhibit the reaction is appropriately selected. As the solvent, for example, an aliphatic alcohol such as methanol, ethanol or propanol; or water can be mentioned. A mixture of these solvents may be used.

In the hydrolysis reaction, the reaction temperature is preferably, −20° C. to 150° C. and more preferably 0 to 100° C.

In the hydrolysis reaction, the reaction time, which varies depending upon the reaction conditions, is preferably 5 minutes to 72 hours, and more preferably 30 minutes to 48 hours.

Step 17

A compound (XVI) can be obtained by the condensation reaction between a compound (XIV) and a compound (XV) in the presence of a base, carbonyldiimidazole and a magnesium salt.

The above condensation reaction can be performed by a known method (for example, ACS Medicinal Chemistry Letters, vol. 2, p. 171-176, 2011) or a similar method thereto.

Step 18

The compound (VA) can be obtained by the amidation reaction between a compound (XVI) and a compound (IIa-a).

As the compound (XVI) and compound (IIa-a) to be used in the amidation reaction, commercially available compounds can be directly used. However, the compounds can be synthesized, for example, in accordance with the above production method.

The amount of the compound (IIa-a) used in the amidation reaction is preferably 0.5 to 3 moles relative to 1 mole of the compound (XVI) and more preferably 0.8 to 1.5 moles.

The amidation reaction is generally performed in a solvent. A solvent that does not inhibit the reaction is appropriately selected. As the solvent, for example, an aromatic hydrocarbon such as toluene, chlorobenzene or xylene; an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the amidation reaction, the reaction temperature is preferably −20° C. to 200° C. and more preferably 0 to 150° C.

In the amidation reaction, the reaction time, which varies depending upon the reaction conditions, is preferably 5 minutes to 72 hours, and more preferably 30 minutes to 48 hours.

5. Production of Compound (Ib)

5-1. Production Method for Compound (Ib-a)

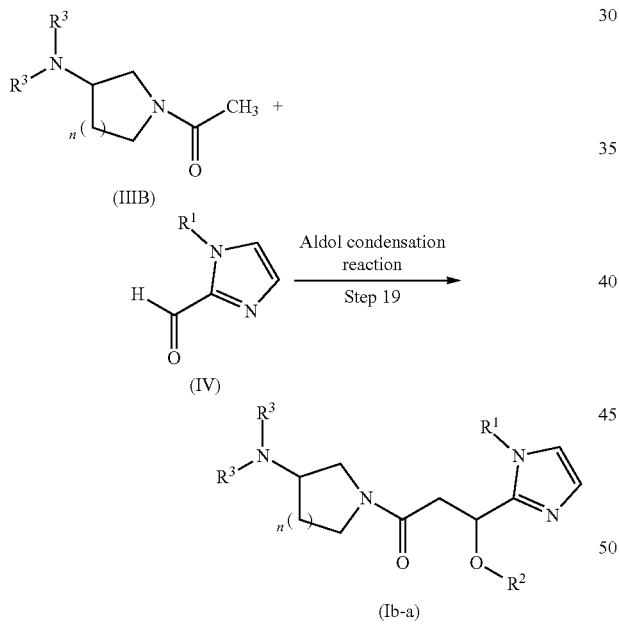

wherein individual reference symbols are the same as defined above.

Step 19

A compound (Ib-a), which is a cyclic amine derivative (I) wherein A is a group represented by general formula (IIb), can be obtained, for example, by the aldol condensation reaction between a compound (IIIB) and a compound (IV) in the presence of a base.

As the compound (IIIB) and compound (IV) to be used in the aldol condensation reaction, commercially available compounds can be directly used. However, the compound (IIIB) can be synthesized, for example, in accordance with the production method that will be described below and the compound (IV) can be synthesized in accordance with the above production method.

As the base to be used in the aldol condensation reaction, for example, lithium diisopropylamide, potassium tert-butoxide, sodium hydride, phenyl lithium or tert-butyl lithium can be mentioned.

The amount of the base used in the aldol condensation reaction is preferably 0.5 to 10 moles relative to 1 mole of the compound (IIIB) and more preferably 0.8 to 5 moles.

The amount of the compound (IV) used in the aldol condensation reaction is preferably 0.5 to 3 moles relative to 1 mole of the compound (IIIB) and more preferably 0.8 to 1.5 moles.

The aldol condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixture of these solvents may be used.

The reaction temperature of the aldol condensation reaction is preferably −78° C. to 100° C. and more preferably −78° C. to 50° C.

The reaction time of the aldol condensation reaction, which varies depending upon the reaction conditions, is preferably 5 minutes to 48 hours and more preferably 30 minutes to 24 hours.

5-2. Production Method for Compounds (Ib-b) and (Ib-c)

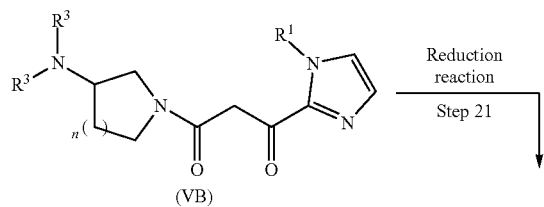

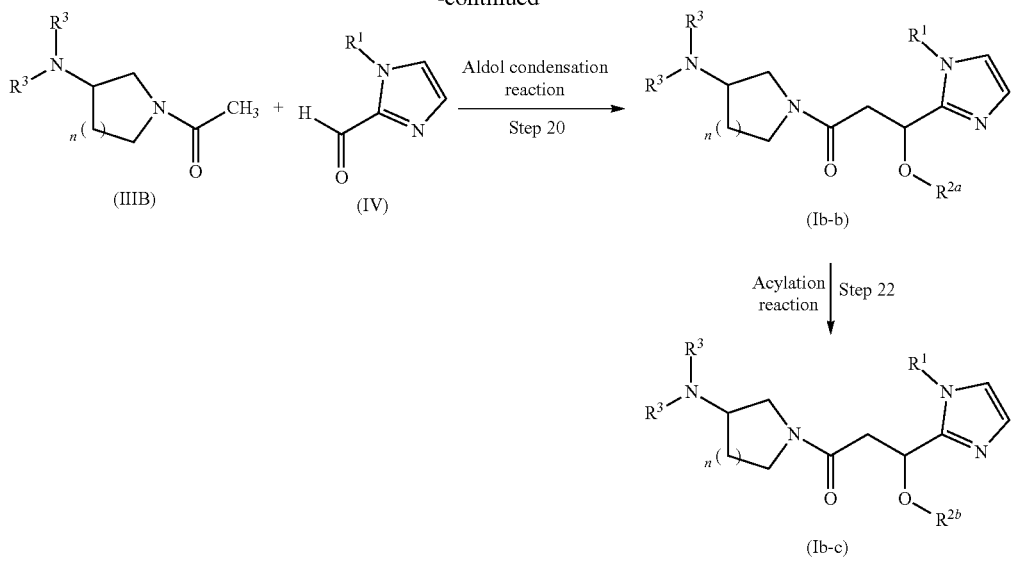

wherein individual reference symbols are the same as defined above.

Step 20

A compound (Ib-b), which is a cyclic amine derivative (I) wherein A is a group represented by general formula (IIb) and $R^2$ is a hydrogen atom, can be obtained, for example, by the aldol condensation reaction between a compound (IIIB) and a compound (IV) in the presence of a base.

As the compound (IIIB) and compound (IV) to be used in the aldol condensation reaction, commercially available compounds can be directly used. However, the compound (IIIB) can be synthesized, for example, in accordance with the production method that will be described below and the compound (IV) can be synthesized, for example, in accordance with the above production method.

As the base to be used in the aldol condensation reaction, for example, lithium diisopropylamide, potassium tert-butoxide, sodium hydride, phenyl lithium or tert-butyl lithium can be mentioned.

The amount of the base used in the aldol condensation reaction is preferably 0.5 to 10 moles relative to 1 mole of the compound (IIIB) and more preferably 0.8 to 5 moles.

The amount of the compound (IV) used in the aldol condensation reaction is preferably 0.5 to 3 moles relative to 1 mole of the compound (IIIB) and more preferably 0.8 to 1.5 moles.

The aldol condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixture of these solvents may be used.

The reaction temperature of the aldol condensation reaction is preferably −78° C. to 100° C. and more preferably −78° C. to 50° C.

The reaction time of the aldol condensation reaction, which varies depending upon the reaction conditions, is preferably 5 minutes to 48 hours and more preferably 30 minutes to 24 hours.

Step 21

A compound (Ib-b), which is a cyclic amine derivative (I) wherein A is a group represented by general formula (IIb) and $R^2$ is a hydrogen atom, can be obtained by the reduction reaction of a compound (VB).

The compound (VB) to be used in the reduction reaction can be synthesized, for example, in accordance with the method that will be described below.

As the reducing agent to be used in the reduction reaction, for example, lithium borohydride, sodium borohydride, diisobutylaluminum hydride, lithium aluminum hydride, lithium triethyl hydride, sodium bis(2-methoxyethoxy)aluminum hydride or a borane complex can be mentioned.

The amount of the reducing agent to be used in the reduction reaction is preferably 0.5 to 10 moles relative to 1 mole of the compound (VB) and more preferably 0.8 to 5 moles.

The reduction reaction is generally performed in a solvent. A solvent that does not inhibit the reaction is appropriately selected. As the solvent, for example, a hydrocarbon such as octane, hexane, benzene or toluene; an ether such as tetrahydrofuran, 1,4-dioxane, ethylene glycol dimethyl ether or diethyl ether; or an alcohol such as methanol, ethanol or 2-propanol can be mentioned. A mixture of these solvents may be used.

The reaction temperature of the reduction reaction is preferably −78° C. to 150° C. and more preferably −78° C. to 100° C.

The reaction time of the reduction reaction, which varies depending upon the reaction conditions, is preferably 5 minutes to 72 hours and more preferably 30 minutes to 24 hours.

Step 22

A compound (Ib-c), which is a cyclic amine derivative (I) wherein A is a group represented by general formula (IIb) and $R^2$ is an alkylcarbonyl group having 2 to 5 carbon atoms can be obtained, for example, by the acylation reaction of a compound (Ib-b) with an acylating agent such as a halide of a carboxylic acid having 2 to 5 carbon atoms or an acid anhydride in the presence of a base.

In the acylation reaction, a compound (Ib-b) and a salt thereof can be used. As the salt herein, for example, the same salt as a pharmacologically acceptable salt as mentioned above can be mentioned.

As the base to be used in the acylation reaction, for example, pyridine, triethylamine, diisopropylethylamine or N,N-dimethylaminopyridine can be mentioned.

The amount of the base to be used in the acylation reaction is preferably 0.5 to 10 moles relative to 1 mole of a compound (Ib-b) and more preferably 0.8 to 5 moles.

As the acylating agent to be used in the acylation reaction, a commercially available compound can be directly used.

The amount of the acylating agent to be used in the acylation reaction is preferably 0.5 to 10 moles relative to 1 mole of the compound (Ib-b) and more preferably 0.8 to 5 moles.

The acylation reaction is generally performed in a solvent. A solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixture of these solvents may be used. When an aromatic amine such as pyridine is selected as a solvent, the acylation reaction can be performed in the absence of a base.

The reaction temperature of the acylation reaction is preferably −40° C. to 100° C. and more preferably −20° C. to 80° C.

The reaction time of the acylation reaction, which varies depending upon the reaction conditions, is preferably 5 minutes to 72 hours and more preferably 30 minutes to 24 hours.

5-3. Salt Formation Steps of Compounds (Ib-a), (Ib-b) and (Ib-c)

The pharmacologically acceptable salts of the compounds (Ib-a), (Ib-b) and (Ib-c) can be obtained, for example, by salt formation reactions of the compound (Ib-a), (Ib-b) or (Ib-c) with an acid.

As the acid to be used in the salt formation reaction, for example, an inorganic acid such as hydrochloric acid, sulfuric acid, phosphoric acid or hydrobromic acid; or an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoic acid, pamoic acid, ascorbic acid, adipic acid, methanesulfonic acid, p-toluenesulfonic acid or cinnamic acid can be mentioned.

The salt formation reaction is generally performed in a solvent. A solvent that does not inhibit the reaction is appropriately selected. As the solvent, for example, an aliphatic alcohol such as methanol, ethanol or 2-propanol; an ether such as diethyl ether, tetrahydrofuran, 1,4-dioxane or ethylene glycol dimethyl ether; an amide such as N,N-dimethylformamide or N-methylpyrrolidone; a sulfoxide such as dimethyl sulfoxide; an aliphatic nitrile such as acetonitrile or propionitrile; a ketone such as acetone or 2-butanone; an ester such as ethyl acetate, methyl acetate or n-butyl acetate; or water can be mentioned. A mixture of these solvents may be used.

6. Production of Compound (IIIB)

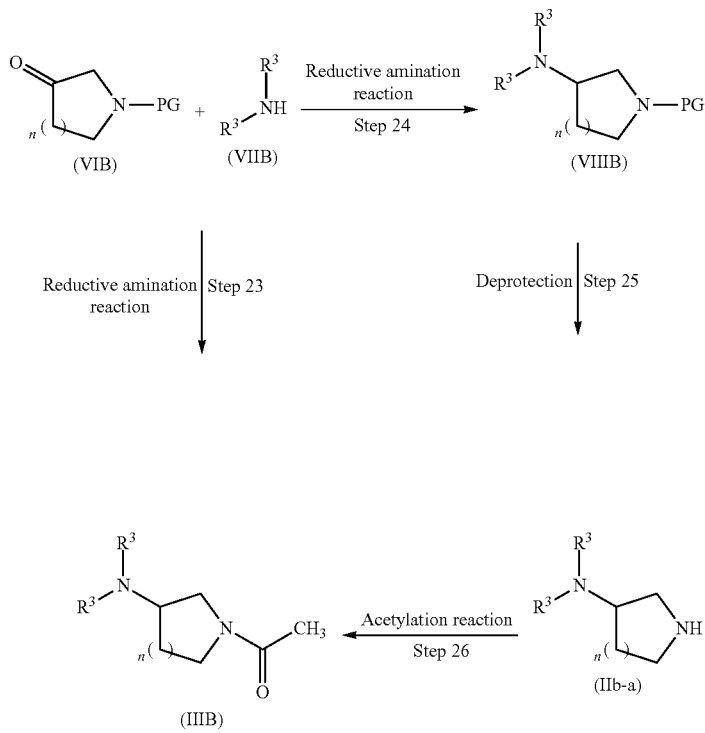

wherein individual reference symbols are the same as defined above.

Step 23

A compound (IIIB) can be obtained by the reductive amination reaction between a compound (VIB) in which PG is an acetyl group and compound (VIIB).

As the compound (VIB) and compound (VIIB) to be used in the reductive amination reaction, commercially available compounds can be directly used.

The reductive amination reaction can be performed in accordance with a known method (for example, Journal of Organic Chemistry, vol. 68, p. 770-779, 2003) or a similar method thereto.

Step 24

A compound (VIIIB) can be obtained by the reductive amination reaction between a compound (VIB) and a compound (VIIB).

As the compound (VIB) and the compound (VIIB) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 25

A compound (IIb-a) can be obtained by the deprotection of a compound (VIIIB).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

Step 26

A compound (IIIB) can be obtained by the acetylation reaction of a compound (IIb-a).

The acetylation reaction can be performed in accordance with a known method (for example, Greene, T. W., "Greene's Protective Groups in Organic Synthesis," Wiley-Interscience) or a similar method thereto.

wherein individual reference symbols are the same as defined above.

Step 27

A compound (VB) can be obtained by the oxidation reaction of a compound (Ib-b).

The compound (Ib-b) to be used in the oxidation reaction can be synthesized in accordance with the above production method.

As the oxidant to be used in the oxidation reaction, for example, manganese dioxide, sulfur trioxide-pyridine, activated dimethyl sulfoxide or Dess-Martin reagent can be mentioned.

The amount of the oxidant to be used in the oxidation reaction is preferably 0.5 to 50 moles relative to 1 mole of the compound (Ib-b) and more preferably 0.8 to 35 moles.

The oxidation reaction is generally performed in a solvent. A solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixture of these solvents may be used.

The reaction temperature of the oxidation reaction is preferably −78° C. to 100° C. and more preferably −78° C. to 40° C.

The reaction time of the oxidation reaction, which varies depending upon the reaction conditions, is preferably 5 minutes to 72 hours and more preferably 30 minutes to 48 hours.

Step 28

A compound (VB) can be obtained by the condensation reaction between a compound (XII) and a compound (IIIB) in the presence of a base.

As the compound (XII) and compound (IIIB) to be used in the condensation reaction, commercially available compounds can be directly used. However, the compounds can be synthesized, for example, in accordance with the above production methods.

As the base to be used in the condensation reaction, for example, lithium diisopropylamide, potassium tert-butoxide, sodium hydride, phenyl lithium or tert-butyl lithium can be mentioned.

7. Production of Compound (VB)

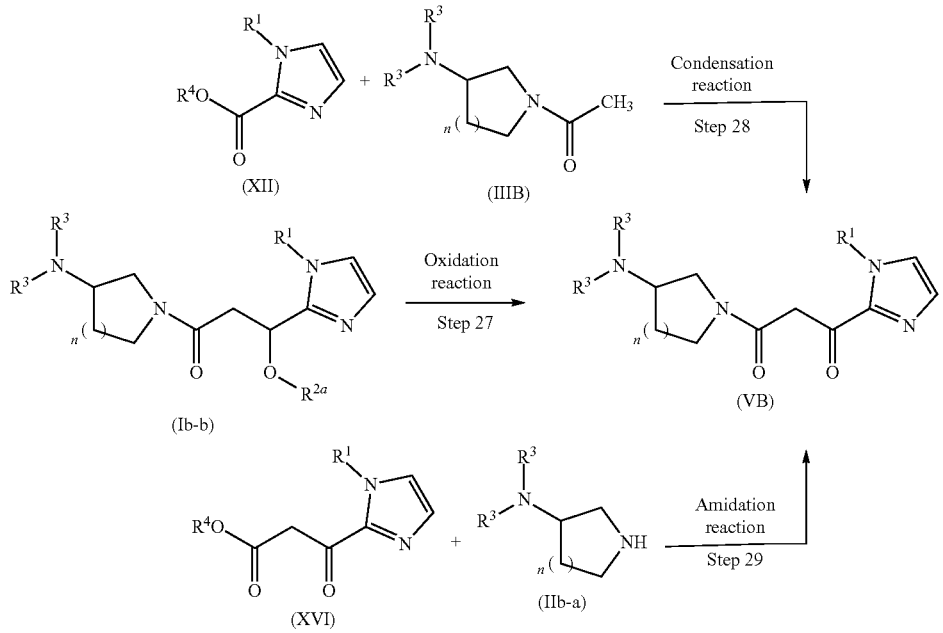

The amount of the base to be used in the condensation reaction is preferably 0.5 to 10 moles relative to 1 mole of the compound (IIIB) and more preferably 0.8 to 5 moles.

The amount of the compound (XII) to be used in the condensation reaction is preferably 0.5 to 3 moles relative to 1 mole of the compound (IIIB) and more preferably 0.8 to 1.5 moles.

The condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixture of these solvents may be used.

The reaction temperature of the condensation reaction is preferably −78° C. to 100° C. and more preferably −78° C. to 50° C.

The reaction time of the condensation reaction, which varies depending upon the reaction conditions, is preferably 5 minutes to 48 hours and more preferably 30 minutes to 24 hours.

Step 29

A compound (VB) can be obtained by the amidation reaction between a compound (XVI) and a compound (IIb-a).

As the compound (XVI) and compound (IIb-a) to be used in the amidation reaction, a commercially available compound can be directly used. However, the compounds can be synthesized, for example, in accordance with the above production methods.

The amount of the compound (IIb-a) to be used in the amidation reaction is preferably 0.5 to 3 moles relative to 1 mole of the compound (XVI) and more preferably 0.8 to 1.5 moles.

The amidation reaction is generally performed in a solvent. A solvent that does not inhibit the reaction is appropriately selected. As the solvent, for example, an aromatic hydrocarbon such as toluene, chlorobenzene or xylene; an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

The reaction temperature of the amidation reaction is preferably −20° C. to 200° C. and more preferably 0 to 150° C.

The reaction time of the amidation reaction, which varies depending upon the reaction conditions, is preferably 5 minutes to 72 hours and more preferably 30 minutes to 48 hours.

8. Production of Compound (Ic)

8-1. Production Method for Compound (Ic-a)

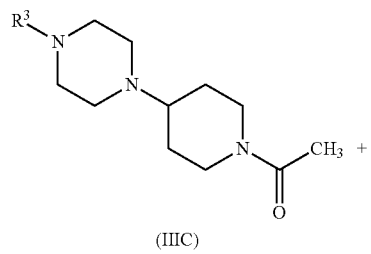

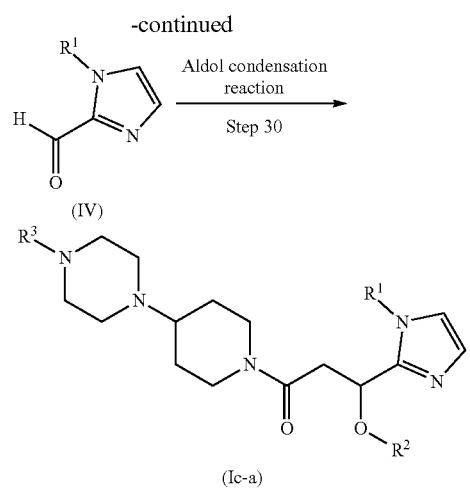

wherein individual reference symbols are the same as defined above.

Step 30

A compound (Ic-a), which is a cyclic amine derivative (I) wherein A is a group represented by general formula (IIc), can be obtained, for example, by the aldol condensation reaction between a compound (IIIC) and a compound (IV) in the presence of a base.

As the compound (IIIC) and compound (IV) to be used in the aldol condensation reaction, commercially available compounds can be directly used. However, the compound (IIIC) can be synthesized for example, in accordance with the production method that will be described below and the compound (IV) can be synthesized in accordance with the above production method.

As the base to be used in the aldol condensation reaction, for example, lithium diisopropylamide, potassium tert-butoxide, sodium hydride, phenyl lithium or tert-butyl lithium can be mentioned.

The amount of the base to be used in the aldol condensation reaction is preferably 0.5 to 10 moles relative to 1 mole of the compound (IIIC) and more preferably 0.8 to 5 moles.

The amount of the compound (IV) to be used in the aldol condensation reaction is preferably 0.5 to 3 moles relative to 1 mole of the compound (IIIC) and more preferably 0.8 to 1.5 moles.

The aldol condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixture of these solvents may be used.

The reaction temperature of the aldol condensation reaction is preferably −78° C. to 100° C. and more preferably −78° C. to 50° C.

The reaction time of the aldol condensation reaction, which varies depending upon the reaction conditions, is preferably 5 minutes to 48 hours and more preferably 30 minutes to 24 hours.

8-2. Production Methods for Compounds (Ic-b) and (Ic-c)

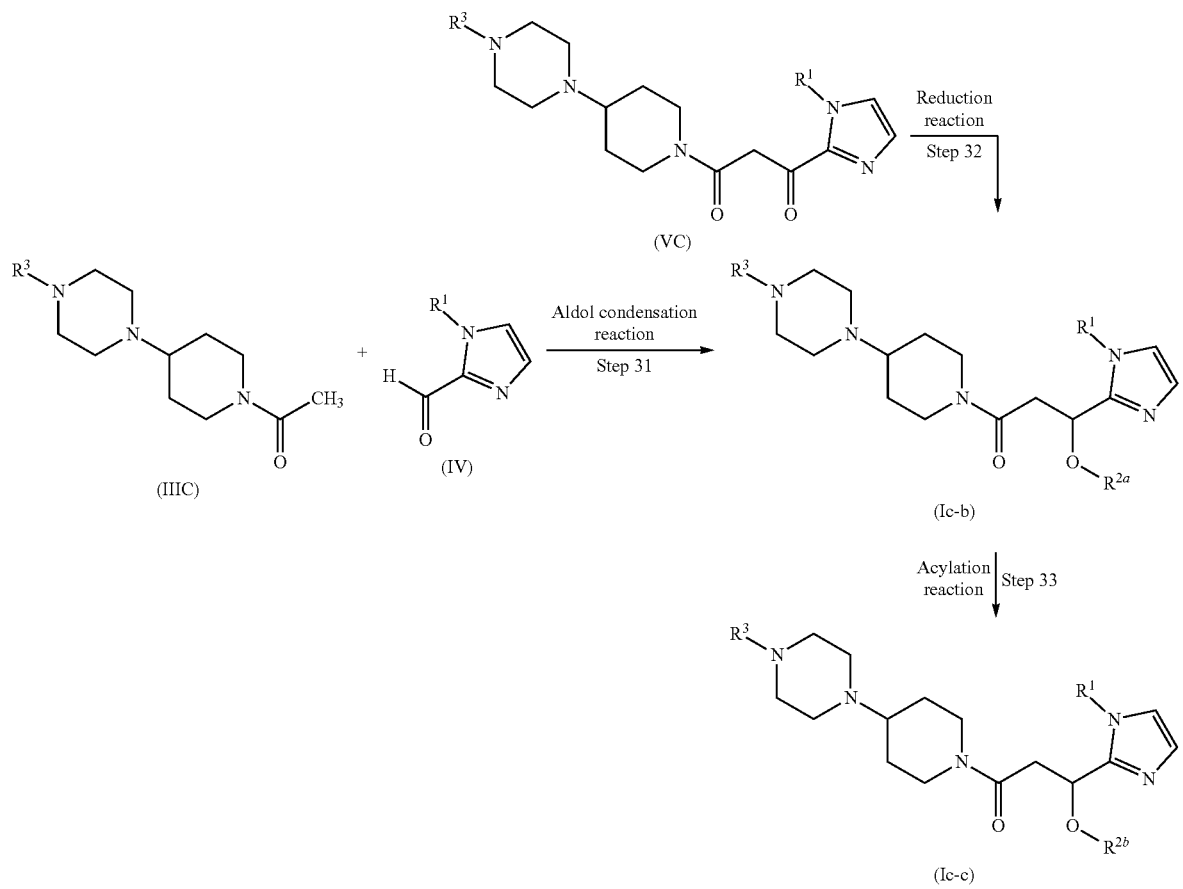

wherein individual reference symbols are the same as defined above.

Step 31

A compound (Ic-b), which is a cyclic amine derivative (I) wherein A is a group represented by general formula (IIc) and $R^2$ is a hydrogen atom, can be obtained, for example, by the aldol condensation reaction between a compound (IIIC) and a compound (IV) in the presence of a base.

As the compound (IIIC) and compound (IV) to be used in the aldol condensation reaction, commercially available compounds can be directly used. However, the compound (IIIC) can be synthesized, for example, in accordance with the production method that will be described below and the compound (IV) can be synthesized in accordance with the above production method.

As the base to be used in the aldol condensation reaction, for example, lithium diisopropylamide, potassium tert-butoxide, sodium hydride, phenyl lithium or tert-butyl lithium can be mentioned.

The amount of the base to be used in the aldol condensation reaction is preferably 0.5 to 10 moles relative to 1 mole of the compound (IIIC) and more preferably 0.8 to 5 moles.

The amount of the compound (IV) to be used in the aldol condensation reaction is preferably 0.5 to 3 moles relative to 1 mole of the compound (IIIC) and more preferably 0.8 to 1.5 moles.

The aldol condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixture of these solvents may be used.

The reaction temperature of the aldol condensation reaction is $-78°$ C. to $100°$ C. and more preferably $-78°$ C. to $50°$ C.

The reaction time of the aldol condensation reaction, which varies depending upon the reaction conditions, is preferably 5 minutes to 48 hours and more preferably 30 minutes to 24 hours.

Step 32

A compound (Ic-b), which is a cyclic amine derivative (I) wherein A is a group represented by general formula (IIc) and $R^2$ is a hydrogen atom, can be obtained by the reduction reaction of a compound (VC).

The compound (VC) to be used in the reduction reaction can be synthesized, for example, in accordance with the production method that will be described below.

As the reducing agent to be used in the reduction reaction, for example, lithium borohydride, sodium borohydride, diisobutylaluminum hydride, lithium aluminum hydride, lithium triethyl hydride, sodium bis(2-methoxyethoxy)aluminum hydride or a borane complex can be mentioned.

The amount of the reducing agent to be used in the reduction reaction is preferably 0.5 to 10 moles relative to 1 mole of the compound (VC) and more preferably 0.8 to 5 moles.

The reduction reaction is generally performed in a solvent. A solvent that does not inhibit the reaction is appropriately selected. As the solvent, for example, a hydrocarbon such as octane, hexane, benzene or toluene; an ether such as tetrahydrofuran, 1,4-dioxane, ethylene glycol dimethyl ether or diethyl ether; or an alcohol such as methanol, ethanol or 2-propanol can be mentioned. A mixture of these solvents may be used.

The reaction temperature of the reduction reaction is preferably −78° C. to 150° C. and more preferably −78° C. to 100° C.

The reaction time of the reduction reaction, which varies depending upon the reaction conditions, is preferably 5 minutes to 72 hours and more preferably 30 minutes to 24 hours.

Step 33

A compound (Ic-c), which is a cyclic amine derivative (I) wherein A is a group represented by general formula (IIc) and $R^2$ is an alkylcarbonyl group having 2 to 5 carbon atoms, can be obtained, for example, by the acylation reaction of a compound (Ic-b) with an acylating agent such as a halide of a carboxylic acid having 2 to 5 carbon atoms or an acid anhydride of a carboxylic acid having 2 to 5 carbon atoms in the presence of a base.

In the acylation reaction, a compound (Ic-b) and a salt thereof can be used. As the salt herein, for example, the same salt as a pharmacologically acceptable salt as mentioned above can be mentioned.

As the base to be used in the acylation reaction, for example, pyridine, triethylamine, diisopropylethylamine or N,N-dimethylamino pyridine can be mentioned.

The amount of the base to be used in the acylation reaction is preferably 0.5 to 10 moles relative to 1 mole of the compound (Ic-b) and more preferably 0.8 to 5 moles.

As the acylating agent to be used in the acylation reaction, a commercially available compound can be directly used.

The amount of the acylating agent to be used in the acylation reaction is preferably 0.5 to 10 moles relative to 1 mole of the compound (Ic-b) and more preferably 0.8 to 5 moles.

The acylation reaction is generally performed in a solvent. A solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile, can be mentioned. A mixture of these solvents may be used. When an aromatic amine such as pyridine is selected as the solvent, the acylation reaction can be performed in the absence of a base.

The reaction temperature of the acylation reaction is preferably −40° C. to 100° C. and more preferably −20° C. to 80° C.

The reaction time of the acylation reaction, which varies depending upon the reaction conditions, is preferably 5 minutes to 72 hours and more preferably 30 minutes to 24 hours.

8-3. Salt Formation Steps of Compounds (Ic-a), (Ic-b) and (Ic-c)

A pharmacologically acceptable salt of compounds (Ic-a), (Ic-b) and (Ic-c) can be obtained, for example, by a salt formation reactions of the compound (Ic-a), (Ic-b) or (Ic-c) with an acid.

As the acid to be used in the salt formation reaction, for example, an inorganic acid such as hydrochloric acid, sulfuric acid, phosphoric acid or hydrobromic acid; or an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoate, pamoic acid, ascorbic acid, adipic acid, methanesulfonic acid, p-toluenesulfonic acid or cinnamic acid.

The salt formation reaction is generally performed in a solvent. A solvent that does not inhibit the reaction is appropriately selected. As the solvent, for example, an aliphatic alcohol such as methanol, ethanol or 2-propanol; an ether such as diethyl ether, tetrahydrofuran, 1,4-dioxane or ethylene glycol dimethyl ether; an amide such as N,N-dimethylformamide or N-methylpyrrolidone; a sulfoxide such as dimethyl sulfoxide; an aliphatic nitrile such as acetonitrile or propionitrile; a ketone such as acetone or 2-butanone; an ester such as ethyl acetate, methyl acetate or n-butyl acetate; or water can be mentioned. A mixture of these solvents may be used.

9. Production of a Compound (IIIC)

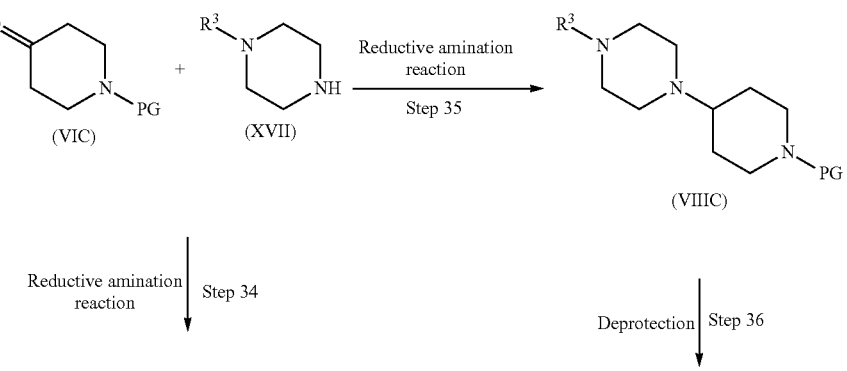

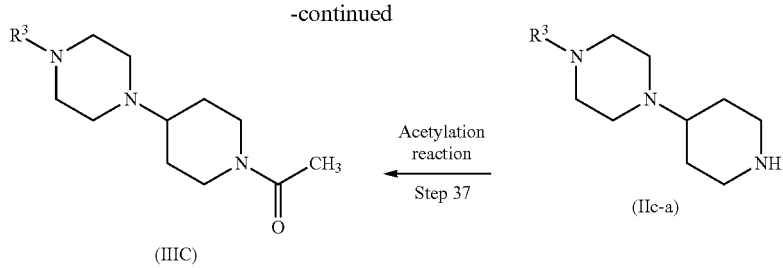

wherein individual reference symbols are the same as defined above.

Step 34

A compound (IIIC) can be obtained by the reductive amination reaction between a compound (VIC) in which PG is an acetyl group and a compound (XVII).

As the compound (VIC) and the compound (XVII) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 35

A compound (VIIIC) can be obtained by the reductive amination reaction between a compound (VIC) and a compound (XVII).

As the compound (VIC) and compound (XVII) to be used in the reductive amination reaction, commercially available compounds can be directly used.

The reductive amination reaction can be performed in accordance with a known method (for example, Journal of Organic Chemistry, vol. 68, p. 770-779, 2003) or a similar method thereto.

Step 36

A compound (IIc-a) can be obtained by the deprotection of a compound (VIIIC).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

Step 37

A compound (IIIC) can be obtained by the acetylation reaction of a compound (IIc-a).

The acetylation reaction can be performed in accordance with a known method (for example, Greene, T. W., "Greene's Protective Groups in Organic Synthesis," Wiley-Interscience) or a similar method thereto.

10. Production of a Compound (VC)

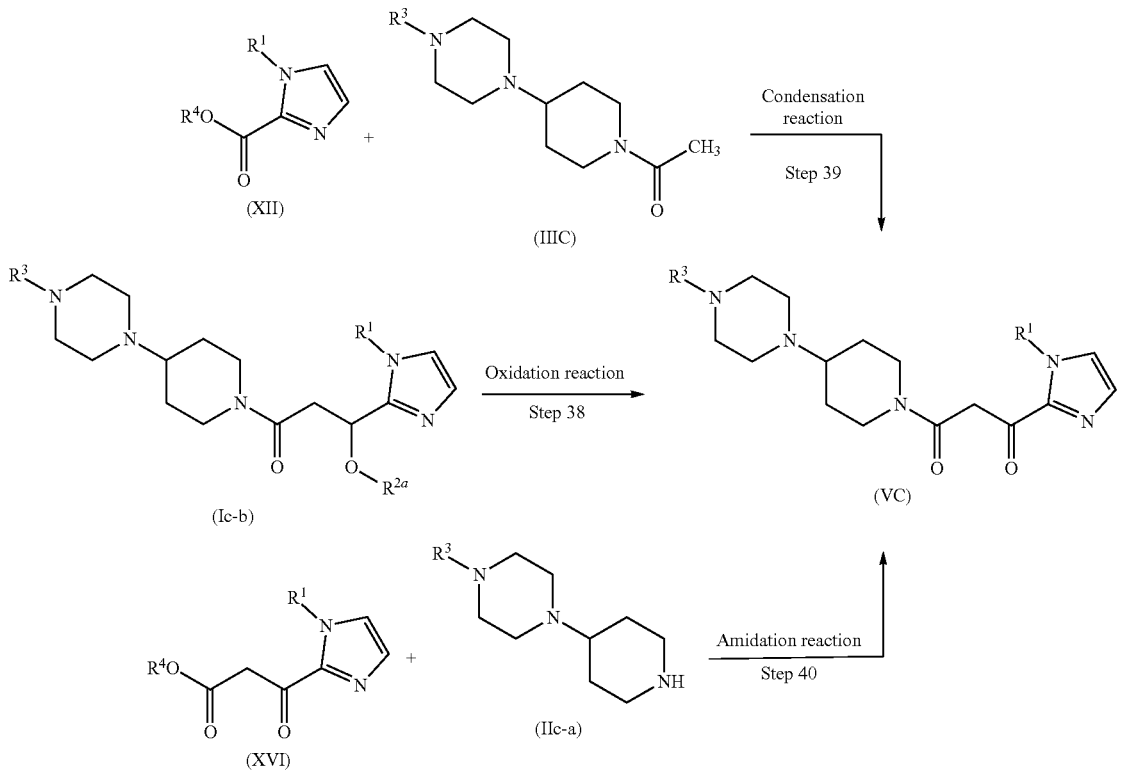

wherein individual reference symbols are the same as defined above.

Step 38

A compound (VC) can be obtained by the oxidation reaction of a compound (Ic-b).

The compound (Ic-b) to be used in the oxidation reaction can be synthesized in accordance with the above production method.

As the oxidant to be used in the oxidation reaction, for example, manganese dioxide, sulfur trioxide-pyridine, activated dimethyl sulfoxide or a Dess-Martin reagent can be mentioned.

The amount of the oxidant to be used in the oxidation reaction is preferably 0.5 to 50 moles relative to 1 mole of a compound (Ic-b) and more preferably 0.8 to 35 moles.

The oxidation reaction is generally performed in a solvent. A solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixture of these solvents may be used.

In the oxidation reaction, the reaction temperature is preferably −78° C. to 100° C. and more preferably −78° C. to 40° C.

In the oxidation reaction, the reaction time, which varies depending upon the reaction conditions, is preferably 5 minutes to 72 hours, and more preferably 30 minutes to 48 hours.

Step 39

A compound (VC) can be obtained by a condensation reaction between a compound (XII) and a compound (IIIC) in the presence of a base.

As the compound (XII) and compound (IIIC) to be used in the condensation reaction, commercially available compounds can be directly used. However, the compound (XII) and compound (IIIC) can be synthesized, for example, in accordance with the above production method.

As the base to be used in the condensation reaction, for example, lithium diisopropylamide, potassium tert-butoxide, sodium hydride, phenyl lithium or tert-butyl lithium can be mentioned.

The amount of the base to be used in the condensation reaction is preferably 0.5 to 10 moles relative to 1 mole of a compound (IIIC) and more preferably 0.8 to 5 moles.

The amount of the compound (XII) to be used in the condensation reaction is preferably 0.5 to 3 moles relative to 1 mole of a compound (IIIC) and more preferably 0.8 to 1.5 moles.

The condensation reaction is generally performed in a solvent. A solvent that does not inhibit the reaction is appropriately selected. As the solvent, for example, a halogenated hydrocarbon such as dichloromethane, chloroform or 1,2-dichloroethane; or an ether such as tetrahydrofuran or 1,4-dioxane can be mentioned. A mixture of these solvents may be used.

In the condensation reaction, the reaction temperature is preferably −78° C. to 100° C. and more preferably −78° C. to 50° C.

In the condensation reaction, the reaction time, which varies depending upon the reaction conditions, is preferably 5 minutes to 48 hours, and more preferably 30 minutes to 24 hours.

Step 40

A compound (VC) can be obtained by the amidation reaction between a compound (XVI) and a compound (IIc-a).

The amount of the compound (IIc-a) to be used in the amidation reaction is preferably 0.5 to 3 moles relative to 1 mole of the compound (XVI) and more preferably 0.8 to 1.5 moles.

The amidation reaction is generally performed in a solvent. A solvent that does not inhibit the reaction is appropriately selected. As the solvent, for example, an aromatic hydrocarbon such as toluene, chlorobenzene or xylene; an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

The reaction temperature of the amidation reaction is preferably −20° C. to 200° C. and more preferably 0 to 150° C.

The reaction time of the amidation reaction, which varies depending upon the reaction conditions, is preferably 5 minutes to 72 hours and more preferably 30 minutes to 48 hours.

11. Production of Compounds (XVIII-a), (XVIII-b) and (XVIII-c)

11-1. Production Method for Compound (XVIII-a)

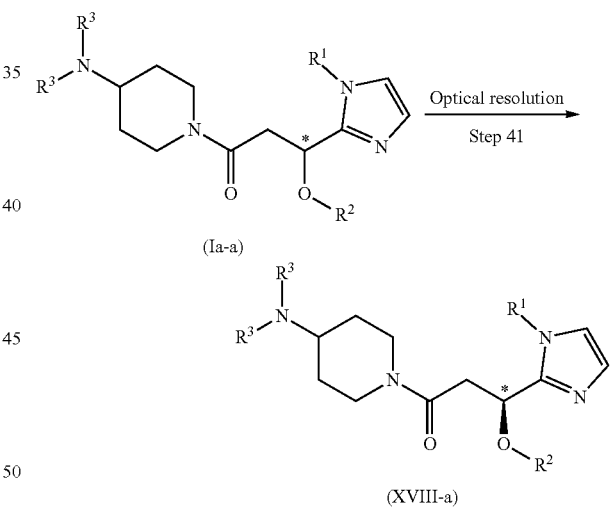

wherein individual reference symbols are the same as defined above.

Step 41

A compound (XVIII-a), which is a cyclic amine derivative (I) wherein A is a group represented by general formula (IIa) and the stereochemical configuration of the asymmetric carbon marked with * is S, can be obtained by a known mean (for example, an optically active synthetic intermediate of a compound (Ia-a) is used or a racemic mixture of the compound (Ia-a) is subjected to a known method or a similar method thereto (for example, optical resolution)).

As the optical resolution, a known means, for example, a chiral column method or a diastereomer method can be mentioned.

1) Chiral Column Method

This is a method of obtaining a desired enantiomer by separating a racemic mixture by an enantiomer separation column (chiral column). For example, in liquid chromatography, an enantiomer can be separated by adding a racemic mixture to a chiral column such as HPLC chiral column (for example, manufactured by Daicel Corporation.) and developing it by using water, various buffers (for example, phosphate buffer), an organic solvent (for example, n-hexane, ethanol, methanol, 1-propanol, 2-propanol, acetonitrile, trifluoroacetic acid, diethylamine or ethylenediamine) singly or in combination.

2) Diastereomer Method

This is a method of obtaining a desired enantiomer by converting a racemic mixture by use of an optically active reagent into a diastereomer mixture, separating a single diastereomer by use of difference in physicochemical property between diastereomers and cutting out an optical active reagent part. The racemic mixture can be converted into a diastereomer mixture by a known method or a similar method thereto using an optically active reagent (for example, MTPA (α-methoxy-α-(trifluoromethyl)phenylacetic acid), N-(p-toluenesulfonyl)-L-phenylalanyl chloride or N-(4-nitrophenylsulfonyl)-L-phenylalanyl chloride). The diastereomer mixture is separated by a known means (for example, fractional recrystallization or chromatography) to obtain a single diastereomer. The optically active reagent part of the single diastereomer is cut out by a known method or a similar method thereto to obtain a desired enantiomer. For example, a condensation reaction between an intramolecular hydroxyl of a compound (Ia-a) and an optical active organic acid or an acid halide thereof (for example, N-(p-toluenesulfonyl)-L-phenylalanyl chloride) is performed to convert a racemic mixture into a diastereomer (ester) mixture. After the mixture is separated, acid hydrolysis reaction or basic hydrolysis reaction is performed to obtain a desired enantiomer.

11-2. Production Methods for Compound (XVIII-b) and (XVIII-c)

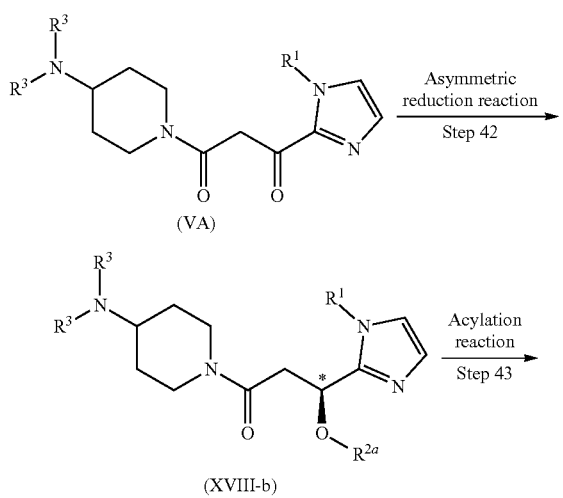

(VA)

(XVIII-b)

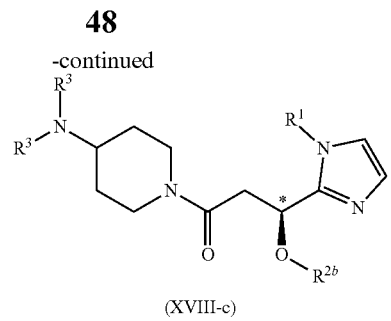

(XVIII-c)

wherein individual reference symbols are the same as defined above.

Step 42

A compound (XVIII-b), which is a cyclic amine derivative (I) wherein A is a group represented by general formula (IIa), the stereochemical configuration of the asymmetric carbon marked with * is S and $R^2$ is a hydrogen atom, can be obtained by a known means, for example, the asymmetric reduction reaction of a compound (VA) or a similar method thereto.

The asymmetric reduction reaction can be performed in accordance with a known method (for example, Journal of American Chemical Society, vol. 133, p. 14960-14963, 2011) or a similar method thereto.

Step 43

A compound (XVIII-c), which is a cyclic amine derivative (I) wherein A is a group represented by general formula (IIa), the stereochemical configuration of the asymmetric carbon marked with * is S and $R^2$ is an alkylcarbonyl group having 2 to 5 carbon atoms, can be obtained, for example, by the acylation reaction of a compound (XVIII-b) with an acylating agent such as a halide of a carboxylic acid having 2 to 5 carbon atoms or an acid anhydride of a carboxylic acid having 2 to 5 carbon atoms in the presence of a base.

In the acylation reaction, a compound (XVIII-b) and a salt thereof can be used. As the salt herein, for example, the same salt as a pharmacologically acceptable salt as mentioned above can be mentioned.

As the base to be used in the acylation reaction, for example, pyridine, triethylamine, diisopropylethylamine or N,N-dimethylamino pyridine can be mentioned.

The amount of the base to be used in the acylation reaction is preferably 0.5 to 10 moles relative to 1 mole of the compound (XVIII-b) and more preferably 0.8 to 5 moles.

As the acylating agent to be used in the acylation reaction, a commercially available compound can be directly used.

The amount of the acylating agent to be used in the acylation reaction is preferably 0.5 to 10 moles relative to 1 mole of the compound (XVIII-b) and more preferably 0.8 to 5 moles.

The acylation reaction is generally performed in a solvent. A solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixture of these solvents may be used. When an aromatic amine such as pyridine is selected as the solvent, the acylation reaction can be performed in the absence of a base.

The reaction temperature of the acylation reaction is preferably −40° C. to 100° C. and more preferably −20° C. to 80° C.

The reaction time of the acylation reaction, which varies depending upon the reaction conditions, is preferably 5 minutes to 72 hours and more preferably 30 minutes to 24 hours.

11-3. Salt Formation Steps of Compounds (XVIII-a), (XVIII-b) and (XVIII-c)

Pharmacologically acceptable salts of compounds (XVIII-a), (XVIII-b) and (XVIII-c) can be obtained through salt formation reactions of the compounds (XVIII-a), (XVIII-b) or (XVIII-c) with an acid.

As the acid to be used in the salt formation reaction, for example, an inorganic acid such as hydrochloric acid, sulfuric acid, phosphoric acid or hydrobromic acid; or an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoic acid, pamoic acid, ascorbic acid, adipic acid, methanesulfonic acid, p-toluenesulfonic acid or cinnamic acid can be mentioned.

The salt formation reaction is generally performed in a solvent. A solvent that does not inhibit the reaction is appropriately selected. As the solvent, for example, an aliphatic alcohol such as methanol, ethanol or 2-propanol; an ether such as diethyl ether, tetrahydrofuran, 1,4-dioxane or ethylene glycol dimethyl ether; an amide such as N,N-dimethylformamide or N-methylpyrrolidone; a sulfoxide such as dimethyl sulfoxide; an aliphatic nitrile such as acetonitrile or propionitrile; a ketone such as acetone or 2-butanone; an ester such as ethyl acetate, methyl acetate or n-butyl acetate; or water can be mentioned. A mixture of these solvents may be used.

The analgesic action of a cyclic amine derivative (I) or a pharmacologically acceptable salt thereof, particularly the therapeutic effect on neuropathic pain and fibromyalgia syndrome can be evaluated by use of an appropriate animal model. As the appropriate animal model for neuropathic pain, for example, a mouse or rat partial sciatic nerve ligation model (Malmberg et al., Pain, vol. 76, p. 215-222, 1998) or a mouse or rat spinal nerve ligation model (Kim et al., Pain, vol. 50, p. 355-363, 1992) can be mentioned. As the appropriate animal model for fibromyalgia syndrome, for example, rat fibromyalgia syndrome models (Sluka et al., Journal of Pharmacology and Experimental Therapeutics, vol. 302, p. 1146-1150, 2002; Nagakura et al., Pain, vol. 146, p. 26-33, 2009; Sluka et al., Pain, vol. 146, p. 3-4, 2009) can be mentioned.

The cyclic amine derivative (I) or a pharmacologically acceptable salt thereof, since it has an excellent analgesic action, particularly a therapeutic effect on neuropathic pain and/or fibromyalgia syndrome, can be used as a medicine, preferably used as an analgesic agent, and particularly preferably as a therapeutic agent for neuropathic pain and/or fibromyalgia syndrome.

In the meantime, pharmaceutical products are required to satisfy strict criteria in view of all aspects including drug efficacy, safety, pharmacokinetics (e.g., metabolic stability, oral absorbability and plasma concentration). However, it is very difficult to find a compound satisfying such all requirements in developing pharmaceutical products. For the reason, pharmaceutical developments of a great many compounds have been stopped because of not only insufficient drug efficacy but also safety concern and inappropriate pharmacokinetics. Accordingly, the success probability of new-drug development is extremely low at present. However, the cyclic amine derivative or a pharmacologically acceptable salt thereof has a strong analgesic effect on pain, particularly neuropathic pain and fibromyalgia syndrome, less central nervous system side effect, high safety, excellent pharmacokinetics in view of metabolic stability, oral absorbability and plasma concentration, and persistence of drug efficacy. Due to these, the cyclic amine derivative can be used as an analgesic agent (a therapeutic agent for neuropathic pain and fibromyalgia syndrome) that can be administered for prolonged periods.

As the neuropathic pain herein, for example, cancer pain, shingles pain, postherpetic neuralgia, AIDS-related neuralgia, painful diabetic neuropathy or trigeminal neuralgia can be mentioned.

The "fibromyalgia syndrome" is a symptom diagnosed by a specialist physician as fibromyalgia syndrome. The diagnosis by a specialist physician is generally made with reference to the classification standard of the American College of Rheumatology.

The cyclic amine derivative (I) or a pharmacologically acceptable salt thereof is useful for treating acute and chronic pain. The acute pain usually lasts for a short period, and, for example, postoperative pain, pain after tooth extraction or trigeminal neuralgia can be mentioned. The chronic pain is defined as pain usually lasting for 3 to 6 months and includes somatogenic pain and psychogenic pain, and, for example, chronic rheumatoid arthritis, osteoarthritis or postherpetic neuralgia can be mentioned.

A medicine containing a cyclic amine derivative (I) or a pharmacologically acceptable salt as an active ingredient, exerts an excellent analgesic action, particularly a therapeutic effect on neuropathic pain and/or fibromyalgia syndrome when it is administered to a mammal (for example, mouse, rat, hamster, rabbit, cat, dog, cow, sheep, monkey or human), especially to a human.

When a cyclic amine derivative (I) or a pharmacologically acceptable salt thereof is used as a medicine, the cyclic amine derivative (I) or a pharmacologically acceptable salt thereof directly or in combination with a pharmaceutically acceptable carrier can be orally or parenterally administered.

As the dosage form when a medicine containing a cyclic amine derivative (I) or a pharmacologically acceptable salt thereof as an active ingredient is orally administered, for example, tablets (including sugar-coated and film-coated tablets), pills, granules, powders, capsules (including soft capsules and micro capsules), syrups, emulsions or suspensions can be mentioned. As the dosage form when a medicine containing a cyclic amine derivative (I) or a pharmacologically acceptable salt thereof as an active ingredient is parenterally administered, for example, injections, infusions, drops, suppositories, endermic liniments or adhesive patches can be mentioned. It is further effective to prepare a sustained-release formulation by using an appropriate base (for example, a butyric acid polymer, a glycolic acid polymer, a butyric acid-glycolic acid copolymer, mixtures of a butyric acid polymer and a glycolic acid polymer, or a polyglycerol fatty acid ester) in combination.

Formulations having the aforementioned dosage forms can be prepared in accordance with production methods known in the field of drug formulation. In this case, if necessary, production can be made by adding an excipient, a binder, a lubricant, a disintegrating agent, a sweetening agent, a surfactant, a suspending agent or an emulsifying agent, which is generally used in the field of drug formulation.

Tablets can be prepared, for example, by adding an excipient, a binder, a disintegrating agent or a lubricant. Pills and granules can be prepared by adding, for example, an excipient, a binder or a disintegrating agent. Powders and capsules can be prepared by adding, for example, an excipient. Syrups can be prepared by adding, for example, a sweetening agent. Emulsions or suspensions can be prepared by adding, for example, a surfactant, a suspending agent or an emulsifier.

As the excipient, for example, lactose, glucose, starch, sucrose, microcrystalline cellulose, powdered *glycyrrhiza*, mannitol, sodium hydrogen carbonate, calcium phosphate or calcium sulfate can be mentioned.

As the binder, for example, a starch paste solution, a gum arabic solution, a gelatin solution, a tragacanth solution, a carboxymethylcellulose solution, a sodium alginate solution or glycerin can be mentioned.

As the disintegrating agent, for example, starch or calcium carbonate can be mentioned.

As the lubricant, for example, magnesium stearate, stearic acid, calcium stearate or purified talc can be mentioned.

As the sweetening agent, for example, glucose, fructose, invert sugar, sorbitol, xylitol, glycerin or simple syrup can be mentioned.

As the surfactant, for example, sodium lauryl sulfate, polysorbate 80, sorbitan monofatty acid ester or stearic acid polyoxyl 40 can be mentioned.

As the suspending agent, for example, Gum arabic, sodium alginate, sodium carboxymethylcellulose, methyl cellulose or bentonite can be mentioned.

As the emulsifier, for example, Gum arabic, tragacanth, gelatin or polysorbate 80 can be mentioned.

When a medicine containing a cyclic amine derivative (I) or a pharmacologically acceptable salt thereof as an active ingredient is prepared in the aforementioned dosage forms, a coloring agent, a preserving agent, a fragrance, a flavoring agent, a stabilizer or a thickener generally used in the field of drug formulation can be added.

The dose per day of a medicine containing a cyclic amine derivative (I) or a pharmacologically acceptable salt thereof as an active ingredient varies depending upon e.g., the state or body weight of the patient or the type or administration route of a compound. For example, in oral administration to an adult (weight: about 60 kg), the amount of the cyclic amine derivative (I) or a pharmacologically acceptable salt thereof serving as an active ingredient falls within the range of 1 to 1000 mg and administration is preferably made in 1 to 3 divided doses. For example, in parenteral administration to an adult (weight: about 60 kg) by an injectable solution, the amount of the cyclic amine derivative (I) or a pharmacologically acceptable salt thereof serving as an active ingredient in e.g., an injection, falls within the range of 0.01 to 100 mg per body weight (1 kg). The injectable solution is preferably intravenously administered.

A cyclic amine derivative (I) or a pharmacologically acceptable salt thereof may be used in combination with other medicinal agents in an appropriate blending ratio to supplement or enhance a therapeutic or prophylactic effect or reduce the dose. In this case, as the other medicinal agents, for example, an antidepressant such as amitriptyline, milnacipran or duloxetine; an anxiolytic such as alprazolam; an anticonvulsant such as carbamazepine; a local anesthetic such as lidocaine; a sympathetic agonist such as adrenaline; an NMDA receptor antagonist such as ketamine; a GABA transaminase inhibitor such as sodium valproate; a calcium channel blocker such as pregabalin; a serotonin receptor antagonist such as risperidone; a GABA receptor function enhancer such as diazepam; or an anti-inflammatory drug such as diclofenac can be mentioned.

EXAMPLES

Our derivatives and methods will be described in detail below with reference to Examples, Comparative Examples and Reference Examples. However, this disclosure is not limited to them.

In the following description, the names of the solvents shown in the NMR data represent the solvents used in the measurement. The 400 MHz NMR spectra were measured by using JNM-AL 400 series Nuclear Magnetic Resonance (NMR) spectrometer (JEOL, Ltd.). Chemical shifts are expressed by δ (unit: ppm) using tetramethylsilane as the reference, and the respective signals, respectively have the following meanings: s (singlet), d (doublet), t (triplet), q (quartet), quint (quintet), sept (septet), m (multiplet), br (broad), dd (double doublet), dt (double triplet), ddd (double double doublet), dq (double quartet), td (triple doublet), and tt (triple triplet). The ESI-MS spectra were measured by using Agilent Technologies 1200 Series, G6130A (from Agilent Technology). Commercially available products were used for all the solvents. For flash column chromatography, YFLC W-prep2XY (from YAMAZEN) was used.

Purification by HPLC was performed in the following conditions:

Apparatus: K-Prep system manufactured by Kabushiki Kaisha Kyoto Chromato

Column: CHIRALPAK IC, 50×250 mm (manufactured by Daicel Corporation)

Solvent: 0.01% ethylenediamine-containing n-hexane/ethanol=60:40 (v/v)

Flow rate: 35 mL/min

Detection method: UV 220 nm

Column temperature: 40° C.

Raw materials and intermediates of cyclic amine derivatives (I) were synthesized by the methods described in the following Reference Examples. Note that commercially-available products were used for the compounds used in synthesizing the compounds of Reference Examples for which synthesis methods are not described below.

Reference Example 1—Synthesis of crude 4-ethylmethylaminopiperidine

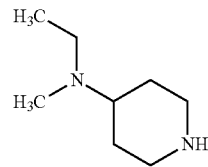

Ethylmethylamine (0.230 mL, 2.68 mmol), acetic acid (0.0120 mL, 0.214 mmol), and sodium triacetoxyborohydride (0.681 g, 3.22 mmol) were added to a solution of benzyl 4-oxopiperidine-1-carboxylate (0.500 g, 2.14 mmol) in dichloromethane (12.0 mL) at 0° C., and the reaction liquid was stirred at room temperature for 16 hours. The reaction liquid was cooled to 0° C. A saturated aqueous solution of sodium hydrogencarbonate was added to the reaction liquid, and the resulting mixture was extracted with chloroform. The organic layer was dried over anhydrous sodium sulfate and filtered, and the filtrate was concentrated under reduced pressure. The residue was purified by flash column chromatography (NH silica gel, chloroform/methanol). The obtained crudely purified product was dissolved in methanol (8.0 mL), and palladium/carbon (10% wet, 0.185 g, 0.174 mmol) was added thereto at room temperature, and the resulting mixture was stirred under hydrogen atmosphere for 16 hours. The reaction liquid was filtered through Celite, and the filtrate was concentrated under reduced pressure to obtain a crude product of 4-ethylmethylaminopiperidine.

Reference Example 2—Synthesis of crude 4-diethylaminopiperidine

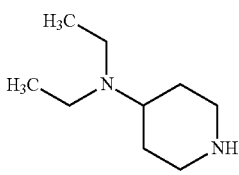

Diethylamine (0.276 mL, 2.68 mmol), acetic acid (0.0120 mL, 0.214 mmol), and sodium triacetoxyborohydride (0.681 g, 3.22 mmol) were added to a solution of benzyl 4-oxopiperidine-1-carboxylate (0.500 g, 2.14 mmol) in dichloromethane (12.0 mL) at 0° C., and the reaction liquid was stirred at room temperature for 16 hours. The reaction liquid was cooled to 0° C. A saturated aqueous solution of sodium hydrogencarbonate was added to the reaction liquid, and the resulting mixture was extracted with chloroform. The organic layer was dried over anhydrous sodium sulfate and filtered, and the filtrate was concentrated under reduced pressure. The residue was purified by flash column chromatography (NH silica gel, chloroform/methanol). The obtained crudely purified product was dissolved in methanol (8.0 mL), and palladium/carbon (10% wet, 0.180 g, 0.169 mmol) was added thereto at room temperature, and the resulting mixture was stirred under hydrogen atmosphere for 16 hours. The reaction liquid was filtered through Celite, and the filtrate was concentrated under reduced pressure to obtain a crude product of 4-diethylaminopiperidine.

Reference Example 3—Synthesis of 4-(1-methylpiperazin-4-yl)piperidine

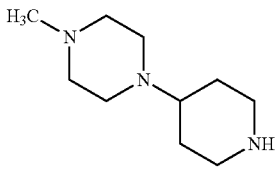

1-Methylpiperazine (0.905 g, 9.03 mmol), acetic acid (0.497 g, 8.28 mmol) and sodium triacetoxyborohydride (1.92 g, 9.03 mmol) were added to a solution of 1-tert-butoxycarbonyl-4-piperidinone (1.50 g, 7.53 mmol) in dichloromethane (25.0 mL) at 0° C. and the reaction liquid was stirred at room temperature for 16 hours. The reaction liquid was cooled to 0° C. A saturated aqueous solution of sodium hydrogencarbonate was added to the reaction liquid, and the resulting mixture was extracted with dichloromethane. The organic layer was dried over anhydrous sodium sulfate and filtered, and the filtrate was concentrated under reduced pressure. The residue was dissolved in hydrochloric acid (1.0 N), and the resulting mixture was extracted with ethyl acetate. A 48% aqueous solution of sodium hydroxide was added to the aqueous layer for basification, and then the resulting mixture was extracted with dichloromethane. The organic layer was dried over anhydrous sodium sulfate and filtered, and the filtrate was concentrated under reduced pressure. The residue was dissolved in methanol (25.0 mL), and concentrated hydrochloric acid (5.0 mL) was added, and then the resulting mixture was stirred at 40° C. for 12 hours. The reaction liquid was concentrated under reduced pressure, and then the residue was dissolved in distilled water. A 48% aqueous solution of sodium hydroxide was added for basification, and then the resulting mixture was extracted with dichloromethane. The organic layer was dried over anhydrous sodium sulfate and filtered, the filtrate was concentrated under reduced pressure, and 4-(1-methylpiperazin-4-yl)piperidine (0.826 g, 4.51 mmol, 60%) was obtained as a white solid.

$^1$H-NMR (400 MHz, CDCl$_3$) δ: 1.35 (2H, dd, J=12.0, 3.6 Hz), 1.41 (2H, dd, J=12.0, 3.6 Hz), 1.85 (2H, d, J=12.8 Hz), 1.96-2.06 (2H, br), 2.28 (3H, s), 2.32 (1H, tt, J=11.6, 3.6 Hz), 3.37-3.70 (8H, m), 3.14 (2H, d, J=12.8 Hz).

ESI-MS: m/z=169 (M+H)$^+$.

Reference Example 4—Synthesis of crude (R)-3-dimethylaminopiperidine hydrochloride

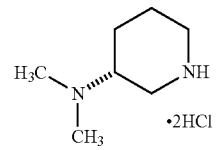

An aqueous solution of formalin (35 wt %, 0.884 mL, 11.2 mmol), acetic acid (0.0290 mL, 0.499 mmol) and sodium triacetoxyborohydride (1.11 g, 5.24 mmol) were added to a solution of (R)-tert-butyl 3-aminopiperidine-1-carboxylate (0.500 g, 2.50 mmol) in dichloromethane (12.0 mL) at 0° C. and the reaction liquid was stirred at room temperature for 16 hours. The reaction liquid was cooled to 0° C. A saturated aqueous solution of sodium hydrogencarbonate was added to the reaction liquid, and the reaction liquid was extracted with chloroform. The organic layer was dried over anhydrous sodium sulfate and filtered, and the filtrate was concentrated under reduced pressure. The residue was purified by flash column chromatography (NH silica gel, chloroform/methanol). 1,4-Dioxane (10.0 mL) was added to the resulting residue at room temperature and dissolved the residue. A solution of hydrogen chloride in 1,4-dioxane (4.0 N, 3.74 mL, 14.9 mmol) was added to the reaction liquid at room temperature and the reaction liquid was stirred at the same temperature for 3 hours. A white solid was precipitated, filtered and collected, washed with hexane, and dried at room temperature to obtain (R)-3-dimethylaminopiperidine hydrochloride as a crude product.

Reference Example 5—Synthesis of 1-(4-(dimethylamino)piperidin-1-yl)ethanone

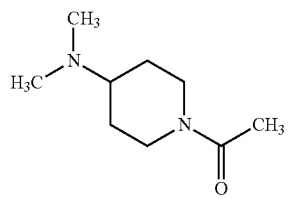

Pyridine (0.922 mL, 9.75 mmol) and acetic anhydride (0.946 mL, 11.7 mmol) were added to a solution of 4-dimethylaminopiperidine (1.00 g, 7.79 mmol) in dichloromethane (7.8 mL) at 0° C. and the reaction liquid was stirred at room temperature for 16 hours. A saturated aqueous solution of sodium hydrogencarbonate was added to the reaction liquid, and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)ethanone (0.869 g, 6.78 mmol, 87%) as a colorless oil.

$^1$H-NMR (400 MHz, CDCl$_3$) δ: 1.30-1.47 (2H, m), 1.79-1.92 (2H, m), 2.10 (3H, s), 2.25-2.40 (7H, m), 2.53-2.63 (1H, m), 3.01-3.11 (1H, m), 3.81-3.90 (1H, m), 4.58-4.66 (1H, m).

ESI-MS: m/z=171 (M+H)$^+$.

Reference Example 6—Synthesis of 1-ethyl-1H-imidazole-2-carbaldehyde

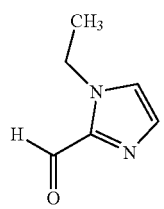

A solution of n-butyllithium in n-hexane (1.6 M, 7.15 mL, 11.4 mmol) was added dropwise to a solution of 1-ethyl-1H-imidazole (1.00 g, 10.4 mmol) in tetrahydrofuran (26 mL) at −78° C. and the reaction liquid was stirred at the same temperature for 1 hour. N,N-dimethylformamide (2.42 mL, 31.2 mmol) was added to the reaction liquid at the same temperature, and the reaction liquid was stirred for 1 hour, and then, the temperature of the reaction liquid was raised to room temperature. A saturated aqueous solution of ammonium chloride was added to the reaction liquid and then the reaction liquid was extracted with ethyl acetate. The organic layer was washed with a 10% aqueous solution of sodium chloride, and then dried over anhydrous sodium sulfate and filtered. The filtrate was concentrated under reduced pressure. The residue was purified by flash column chromatography (silica gel, hexane/ethyl acetate) to obtain 1-ethyl-1H-imidazole-2-carbaldehyde (1.12 g, 9.02 mmol, 87%) as a yellow oil.

$^1$H-NMR (400 MHz, CDCl$_3$) δ: 1.44 (3H, t, J=7.6 Hz), 4.45 (2H, q, J=7.6 Hz), 7.18 (1H, s), 7.28 (1H, d, J=1.6 Hz), 9.82 (1H, s).

Reference Example 7—Synthesis of 1-(2,2,2-trifluoroethyl)-1H-imidazole-2-carbaldehyde

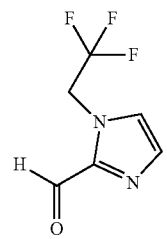

Dess-Martin reagent (1.02 g, 2.40 mmol) was added to a solution of (1-(2,2,2-trifluoroethyl)-1H-imidazol-2-yl)methanol (0.360 g, 2.00 mmol) in dichloromethane (20.0 mL) at 0° C. and the resultant mixture was stirred at room temperature for 1 hour. The reaction liquid was filtered through Celite, and the filtrate was concentrated under reduced pressure. The residue was purified by flash column chromatography (silica gel, hexane/ethyl acetate) to obtain 1-(2,2,2-trifluoroethyl)-1H-imidazole-2-carbaldehyde (0.335 g, 1.88 mmol, 94%) as a white solid.

$^1$H-NMR (400 MHz, CDCl$_3$) δ: 5.16 (2H, q, J=8.0 Hz), 7.25 (1H, brs), 7.38 (1H, brs), 9.83-9.85 (1H, m).

ESI-MS: m/z=179 (M+H)$^+$.

Reference Example 8—Synthesis of ethyl 1-(difluoromethyl)-1H-imidazole-2-carboxylate

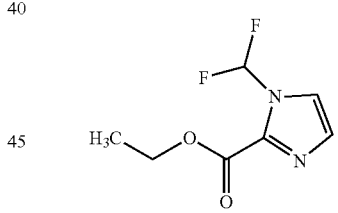

Potassium carbonate (1.28 g, 9.28 mmol) and sodium chlorodifluoroacetate (1.31 g, 8.56 mmol) were added to a solution of ethyl 1H-imidazole-2-carboxylate (1.00 g, 7.14 mmol) in acetonitrile (35 mL) at room temperature and the resultant mixture was stirred at 60° C. for 24 hours. Further, potassium carbonate (0.640 g, 4.63 mmol) and sodium chlorodifluoroacetate (0.660 g, 4.33 mmol) were added at room temperature and the reaction liquid was stirred at 80° C. for 8 hours. The reaction liquid was cooled to room temperature and distilled water was added to the reaction liquid and the reaction liquid was extracted with ethyl acetate. The organic layer was washed with a 10% aqueous solution of sodium chloride, dried over anhydrous sodium sulfate and filtered. The filtrate was concentrated under reduced pressure. The residue was purified by flash column chromatography (silica gel, hexane/ethyl acetate) to obtain ethyl 1-(difluoromethyl)-1H-imidazole-2-carboxylate (0.838 g, 4.41 mmol, 62%) as a colorless oil.

¹H-NMR (400 MHz, CDCl₃) δ: 1.46 (3H, t, J=7.2 Hz), 4.47 (2H, q, J=7.2 Hz), 7.28 (1H, s), 7.53 (1H, d, J=1.6 Hz), 8.16 (1H, t, J=60.8 Hz).

Reference Example 9—Synthesis of ethyl 1-methyl-1H-imidazole-2-carboxylate

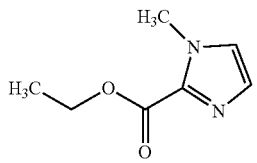

Triethylamine (3.40 mL, 24.4 mmol) and ethyl chloroformate (2.34 mL, 24.4 mmol) were added to a solution of 1-methyl-1H-imidazole (1.00 g, 12.2 mmol) in acetonitrile (4.0 mL) at 0° C. and the reaction liquid was stirred at room temperature for 16 hours. The reaction liquid was filtered through Celite and the filtrate was concentrated under reduced pressure. The residue was purified by flash column chromatography (silica gel, hexane/ethyl acetate) to obtain ethyl 1-methyl-1H-imidazole-2-carboxylate (1.50 g, 9.73 mmol, 80%) as a white solid.

¹H-NMR (400 MHz, CDCl₃) δ: 1.42 (3H, t, J=7.2 Hz), 4.01 (3H, s), 4.40 (2H, q, J=7.2 Hz), 7.01-7.03 (1H, m), 7.13-7.15 (1H, m).

ESI-MS: m/z=155 (M+H)⁺.

Reference Example 10—Synthesis of ethyl 3-(1-methyl-1H-imidazol-2-yl)-3-oxopropanoate

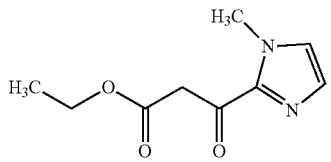

An aqueous solution of sodium hydroxide (1.0 N, 14.6 mL, 14.6 mmol) was added to a solution of ethyl 1-methyl-1H-imidazole-2-carboxylate (1.50 g, 9.73 mmol) in methanol (15.0 mL) at room temperature and the reaction liquid was stirred at the same temperature for 3 hours. The reaction liquid was cooled to 0° C. Hydrochloric acid (1.0 N) was added to the reaction liquid for neutralization, and then the reaction liquid was concentrated under reduced pressure. The residue was subjected to azeotropic distillation with toluene, and ethanol was added. The precipitate was filtered through Celite, and the filtrate was concentrated under reduced pressure. The resulting crude product was dissolved in acetonitrile (7.0 mL) and carbonyldiimidazole (1.54 g, 9.52 mmol) was added at room temperature. The reaction liquid was stirred at the same temperature for 2.5 hours (reaction liquid A). Separately, magnesium chloride (0.997 g, 10.5 mmol) was dissolved in acetonitrile (7.0 mL) and a potassium salt of ethyl malonate (1.70 g, 9.99 mmol) and triethylamine (2.98 mL, 21.4 mmol) were added at room temperature. The reaction liquid was stirred at the same temperature for 2.5 hours (reaction liquid B). Reaction liquid A was added to reaction liquid B at room temperature and the reaction liquid was stirred at 80° C. for 2 hours. The reaction liquid was cooled to room temperature. After hydrochloric acid (1.0 N) was added to the reaction liquid, the reaction liquid was extracted with ethyl acetate. The organic layer was washed with a 10% aqueous solution of sodium chloride, dried over anhydrous sodium sulfate and filtered. The filtrate was concentrated under reduced pressure. The residue was purified by flash column chromatography (silica gel, hexane/ethyl acetate) to obtain ethyl 3-(1-methyl-1H-imidazol-2-yl)-3-oxopropanoate (0.721 g, 3.67 mmol, 38%) as a white solid.

¹H-NMR (400 MHz, CDCl₃) δ: 1.27 (3H, t, J=7.2 Hz), 4.01 (3H, s), 4.13 (2H, s), 4.21 (2H, q, J=7.2 Hz), 7.05-7.07 (1H, m), 7.15-7.17 (1H, m).

ESI-MS: m/z=197 (M+H)⁺.

Reference Example 11—Synthesis of 1-(4-(ethylmethylamino)piperidin-1-yl)-3-(1-methyl-1H-imidazol-2-yl)propan-1,3-dione

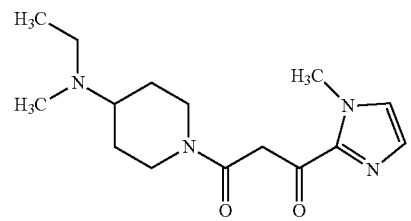 [SMILES: CCN(C)C1CCN(C(=O)CC(=O)c2nccn2C)CC1]

Crude 4-ethylmethylaminopiperidine (0.130 g, 0.917 mmol) was added to a solution of ethyl 3-(1-methyl-1H-imidazol-2-yl)-3-oxopropanoate (0.150 g, 0.765 mmol) in toluene (0.38 mL) at room temperature. The reaction liquid was stirred at 110° C. for 10 hours and concentrated under reduced pressure. The residue was purified by flash column chromatography (NH silica gel, chloroform/methanol) to obtain 1-(4-(ethylmethylamino)piperidin-1-yl)-3-(1-methyl-1H-imidazol-2-yl)propan-1,3-dione (0.191 g, 0.653 mmol, 85%) as a colorless oil.

¹H-NMR (400 MHz, CDCl₃) δ: 1.06 (3H, t, J=7.2 Hz), 1.40-1.70 (2H, m), 1.76-1.85 (2H, m), 2.25 (3H, s), 2.48-2.67 (4H, m), 3.03-3.13 (1H, m), 3.82-3.90 (1H, m), 4.01 (3H, s), 4.15-4.30 (2H, m), 4.62-4.70 (1H, m), 7.03-7.05 (1H, m), 7.13-7.15 (1H, m).

ESI-MS: m/z=293 (M+H)⁺.

Reference Example 12—Synthesis of 1-(4-(diethylamino)piperidin-1-yl)-3-(1-methyl-1H-imidazol-2-yl)propan-1,3-dione

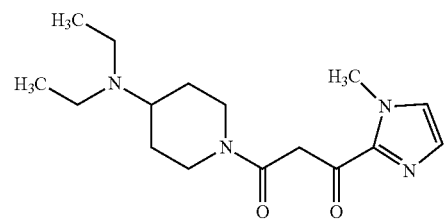 [SMILES: CCN(CC)C1CCN(C(=O)CC(=O)c2nccn2C)CC1]

Crude 4-diethylaminopiperidine (0.143 g, 0.917 mmol) was added to a solution of ethyl 3-(1-methyl-1H-imidazol-2-yl)-3-oxopropanoate (0.150 g, 0.765 mmol) in toluene (0.38 mL) at room temperature. The reaction liquid was stirred at 110° C. for 10 hours and concentrated under reduced pressure. The residue was purified by flash column chromatography (NH silica gel, chloroform/methanol) to obtain 1-(4-(diethylamino)piperidin-1-yl)-3-(1-methyl-1H-imidazol-2-yl)propan-1,3-dione (0.0750 g, 0.245 mmol, 32%) as a colorless oil.

$^1$H-NMR (400 MHz, CDCl$_3$) δ: 1.02 (6H, t, J=6.8 Hz), 1.37-1.58 (2H, m), 1.73-1.98 (2H, m), 2.48-2.78 (6H, m), 3.01-3.11 (1H, m), 3.80-3.88 (1H, m), 4.00 (3H, s), 4.14-4.28 (2H, m), 4.60-4.70 (1H, m), 7.03-7.05 (1H, m), 7.12-7.14 (1H, m).

ESI-MS: m/z=307 (M+H)$^+$.

Reference Example 13—Synthesis of 1-(1-methyl-1H-imidazol-2-yl)-3-(4-(4-methylpiperazin-1-yl)piperidin-1-yl)propan-1,3-dione

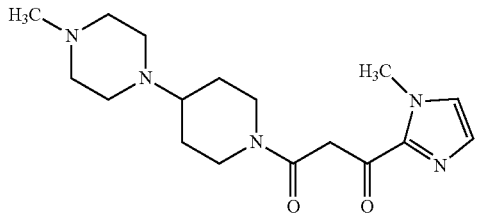 [SMILES: CN1CCN(C2CCN(C(=O)CC(=O)c3nccn3C)CC2)CC1]

4-(1-Methylpiperazin-4-yl)piperidine (0.170 g, 0.927 mmol) was added to a solution of ethyl 3-(1-methyl-1H-imidazol-2-yl)-3-oxopropanoate (0.200 g, 1.02 mmol) in toluene (0.46 mL) at room temperature. The reaction liquid was stirred at 110° C. for 16 hours and concentrated under reduced pressure. The residue was purified by flash column chromatography (NH silica gel, chloroform/methanol) to obtain 1-(1-methyl-1H-imidazol-2-yl)-3-(4-(4-methylpiperazin-1-yl)piperidin-1-yl)propan-1,3-dione (0.290 g, 0.870 mmol, 94%) as a colorless oil.

$^1$H-NMR (400 MHz, CDCl$_3$) δ: 1.38-1.60 (2H, m), 1.82-1.90 (2H, m), 1.95-2.10 (1H, m), 2.27 (3H, s), 2.36-2.68 (9H, m), 3.02-3.12 (1H, m), 3.79-3.88 (1H, m), 3.98 (3H, s), 4.13-4.28 (2H, m), 4.57-4.90 (1H, m), 7.02-7.04 (1H, m), 7.11-7.13 (1H, m).

ESI-MS: m/z=334 (M+H)$^+$.

Reference Example 14—Synthesis of (R)-1-(3-(dimethylamino)piperidin-1-yl)-3-(1-methyl-1H-imidazol-2-yl)propan-1,3-dione

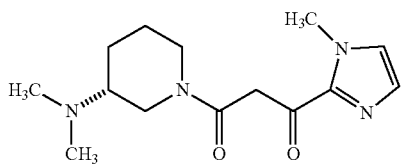 [SMILES: CN(C)[C@@H]1CCCN(C(=O)CC(=O)c2nccn2C)C1]

Crude (R)-3-dimethylaminopiperidine hydrochloride (0.186 g, 0.927 mmol) and diisopropylethylamine (0.809 mL, 4.63 mmol) were added to ethyl 3-(1-methyl-1H-imidazol-2-yl)-3-oxopropanoate (0.200 g, 1.02 mmol) at room temperature. The reaction liquid was stirred at 110° C. for 12 hours and concentrated under reduced pressure. The residue was purified by flash column chromatography (NH silica gel, chloroform/methanol) to obtain (R)-1-(3-(dimethylamino)piperidin-1-yl)-3-(1-methyl-1H-imidazol-2-yl)propan-1,3-dione (0.140 g, 0.503 mmol, 54%) as a colorless oil.

$^1$H-NMR (400 MHz, CDCl$_3$) δ: 1.35-1.85 (2H, m), 1.97-2.07 (1H, m), 2.16-2.38 (7H, m), 2.42-2.68 (1H, m), 2.87-3.05 (1H, m), 3.63-3.76 (1H, m), 3.84-4.02 (4H, m), 4.12-4.32 (2H, m), 4.53-4.70 (1H, m), 7.03-7.05 (1H, m), 7.13-7.15 (1H, m).

ESI-MS: m/z=279 (M+H)$^+$.

Reference Example 15—Synthesis of (R)-1-(3-(dimethylamino)pyrrolidin-1-yl)-3-(1-methyl-1H-imidazol-2-yl)propan-1,3-dione

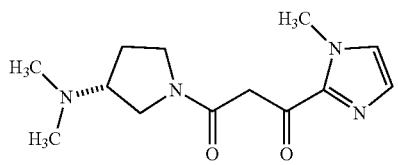 [SMILES: CN(C)[C@@H]1CCN(C(=O)CC(=O)c2nccn2C)C1]

(R)-3-dimethylaminopyrrolidine (0.106 g, 0.927 mmol) was added to ethyl 3-(1-methyl-1H-imidazol-2-yl)-3-oxopropanoate (0.200 g, 1.02 mmol) at room temperature. The reaction liquid was stirred at 110° C. for 6 hours and concentrated under reduced pressure. The residue was purified by flash column chromatography (NH silica gel, chloroform/methanol) to obtain (R)-1-(3-(dimethylamino)pyrrolidin-1-yl)-3-(1-methyl-1H-imidazol-2-yl)propan-1,3-dione (0.220 g, 0.832 mmol, 90%) as a colorless oil.

$^1$H-NMR (400 MHz, CDCl$_3$) δ: 1.62-2.22 (6H, m), 1.85-1.98 (1H, m), 2.07-2.22 (1H, m), 2.65-2.87 (1H, m), 3.18-3.90 (4H, m), 4.00 (3H, s), 4.12-4.16 (2H, m), 7.03-7.05 (1H, m), 7.12-7.14 (1H, m).

ESI-MS: m/z=265 (M+H)$^+$.

Reference Example 16—Synthesis of 1-(4-(dimethylamino)piperidin-1-yl)-3-(1-methyl-1H-imidazol-2-yl)propan-1,3-dione

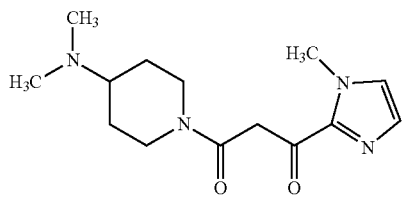 [SMILES: CN(C)C1CCN(C(=O)CC(=O)c2nccn2C)CC1]

A solution of lithium diisopropylamide in tetrahydrofuran (2.0 M, 7.05 mL, 14.1 mmol) was added dropwise to a solution of 1-(4-(dimethylamino)piperidin-1-yl)ethanone (1.00 g, 5.87 mmol) in tetrahydrofuran (20 mL) at −78° C. and the reaction liquid was stirred at the same temperature for 1 hour. A solution of ethyl 1-methyl-1H-imidazole-2-carboxylate (1.09 g, 7.05 mmol) in tetrahydrofuran (9.0 mL) was added to the reaction liquid at the same temperature. The reaction liquid was stirred for 1 hour and then stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, hexane/ethyl acetate) to obtain 1-(4-(dimethylamino)piperidin-1-yl)-3-(1-methyl-1H-imidazol-2-yl)propan-1,3-dione (0.990 g, 3.56 mmol, 61%) as a colorless oil.

$^1$H-NMR (400 MHz, CDCl$_3$) δ: 1.32-1.5 (2H, m), 1.80-1.94 (2H, m), 2.22-41 (7H, m), 2.60-2.70 (1H, m), 3.03-3.13 (1H, m), 3.80-3.89 (1H, m), 4.01 (3H, s), 4.23 (2H, dd, J=15.6, 36.8 Hz), 4.55-4.67 (1H, m), 7.05 (1H, s), 7.14 (1H, s).

ESI-MS: m/z=279 (M+H)$^+$.

Reference Example 17—Synthesis of 1-(1-(difluoromethyl)-1H-imidazol-2-yl)-3-(4-(dimethylamino)piperidin-1-yl)propan-1,3-dione

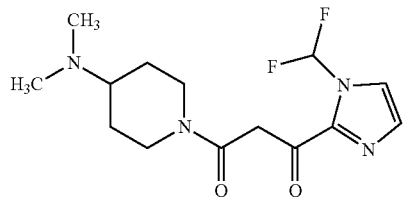 [SMILES: CN(C)C1CCN(C(=O)CC(=O)c2nccn2C(F)F)CC1]

A solution of lithium diisopropylamide in tetrahydrofuran (2.0 M, 2.19 mL, 4.37 mmol) was added dropwise to a solution of 1-(4-(dimethylamino)piperidin-1-yl)ethanone (0.310 g, 1.82 mmol) in tetrahydrofuran (6.0 mL) at −78° C. and the reaction liquid was stirred at the same temperature for 1 hour. A solution of ethyl 1-(difluoromethyl)-1H-imidazole-2-carboxylate (0.415 g, 2.19 mmol) in tetrahydrofuran (3.0 mL) was added to the reaction liquid at the same temperature. The reaction liquid was stirred for 1 hour and stirred at 0° C. for further 1 hour. A saturated aqueous solution of ammonium chloride, an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, hexane/ethyl acetate) to obtain 1-(1-(difluoromethyl)-1H-imidazol-2-yl)-3-(4-(dimethylamino)piperidin-1-yl)propan-1,3-dione (0.311 g, 0.989 mmol, 54%) as a yellow oil.

$^1$H-NMR (400 MHz, CDCl$_3$) δ: 1.38-1.58 (2H, m), 1.80-1.94 (2H, m), 2.05 (6H, s), 2.31-2.42 (1H, m), 2.63-2.72 (1H, m), 3.08-3.18 (1H, m), 3.79-3.86 (1H, m), 4.22 (2H, dd, J=15.6, 24.6 Hz), 4.55-4.62 (1H, m), 7.27 (1H, s), 7.55 (1H, s), 8.08 (1H, t, J=60.8 Hz).

ESI-MS: m/z=315 (M+H)$^+$.

Example 1—Synthesis of 1-(4-(ethylmethylamino)piperidin-1-yl)-3-hydroxy-3-(1-methyl-1H-imidazol-2-yl)propan-1-one

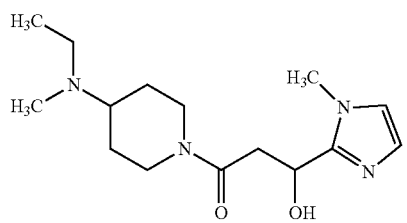 [SMILES: CCN(C)C1CCN(C(=O)CC(O)c2nccn2C)CC1]

Sodium borohydride (0.0220 g, 0.582 mmol) was added to a solution of 1-(4-(ethylmethylamino)piperidin-1-yl)-3-(1-methyl-1H-imidazol-2-yl)propan-1,3-dione (0.160 g, 0.547 mmol) in methanol (2.7 mL) at room temperature and the reaction liquid was stirred at the same temperature for 3 hours. A saturated aqueous solution of sodium hydrogencarbonate was added to the reaction liquid and the reaction liquid was concentrated under reduced pressure. Distilled water was added to the residue and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(ethylmethylamino)piperidin-1-yl)-3-hydroxy-3-(1-methyl-1H-imidazol-2-yl)propan-1-one (0.0699 g, 0.237 mmol, 43%) (hereinafter referred to as the compound of Example 1) as a colorless oil.

$^1$H-NMR (400 MHz, CDCl$_3$) δ: 1.02-1.10 (3H, m), 1.35-1.58 (2H, m), 1.78-1.88 (2H, m), 2.23-2.25 (3H, m), 2.56-2.67 (4H, m), 2.98-3.09 (2H, m), 3.13-3.23 (1H, m), 3.77 (3H, s), 4.00-4.10 (1H, m), 4.60-4.74 (2H, m), 5.18-5.25 (1H, m), 6.85-6.87 (1H, m), 6.92-6.94 (1H, m).

ESI-MS: m/z=295 (M+H)$^+$.

Example 2—Synthesis of 1-(4-(diethylamino)piperidin-1-yl)-3-hydroxy-3-(1-methyl-1H-imidazol-2-yl)propan-1-one

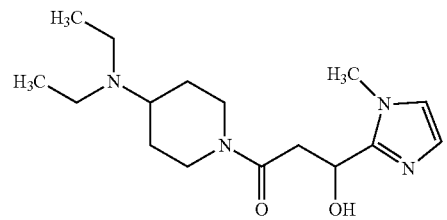 [SMILES: CCN(CC)C1CCN(C(=O)CC(O)c2nccn2C)CC1]

Sodium borohydride (0.0109 g, 0.287 mmol) was added to a solution of 1-(4-(diethylamino)piperidin-1-yl)-3-(1-methyl-1H-imidazol-2-yl)propan-1,3-dione (0.0800 g, 0.261 mmol) in methanol (1.3 mL) at room temperature and the reaction liquid was stirred at the same temperature for 3 hours. A saturated aqueous solution of sodium hydrogencarbonate was added to the reaction liquid and the reaction liquid was concentrated under reduced pressure. Distilled water was added to the residue and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(diethylamino)piperidin-1-yl)-3-hydroxy-3-(1-methyl-1H-imidazol-2-yl)propan-1-one (0.0561 g, 0.182 mmol, 70%) (hereinafter referred to as the compound of Example 2) as a colorless oil.

$^1$H-NMR (400 MHz, DMSO-d$_6$) δ: 0.94 (6H, t, J=6.8 Hz), 1.05-1.75 (5H, m), 2.42-3.10 (8H, m), 3.64 (3H, s), 3.93-4.02 (1H, m), 4.32-4.43 (1H, m), 5.00-5.08 (1H, m), 5.34-5.42 (1H, m), 6.69-6.71 (1H, m), 7.01-7.03 (1H, m).

ESI-MS: m/z=309 (M+H)$^+$.

Example 3—Synthesis of 3-hydroxy-3-(1-methyl-1H-imidazol-2-yl)-1-(4-(4-methylpiperazin-1-yl)piperidin-1-yl)propan-1-one

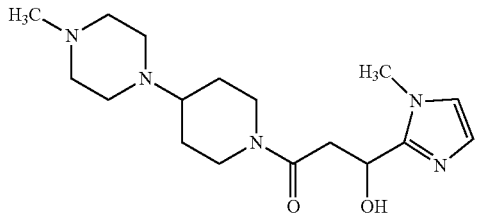 [SMILES: CN1CCN(C2CCN(C(=O)CC(O)c3nccn3C)CC2)CC1]

Sodium borohydride (0.0360 g, 0.957 mmol) was added to a solution of 1-(1-methyl-1H-imidazol-2-yl)-3-(4-(4-methylpiperazin-1-yl)piperidin-1-yl)propan-1,3-dione (0.290 g, 0.870 mmol) in methanol (4.4 mL) at room temperature and the reaction liquid was stirred at the same temperature for 3 hours. A saturated aqueous solution of sodium hydrogencarbonate was added to the reaction liquid and the reaction liquid was concentrated under reduced pressure. Distilled water was added to the residue and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 3-hydroxy-3-(1-methyl-1H-imidazol-2-yl)-1-(4-(4-methylpiperazin-1-yl)piperidin-1-yl)propan-1-one (0.140 g, 0.417 mmol, 48%) (hereinafter referred to as the compound of Example 3) as a colorless oil.

$^1$H-NMR (400 MHz, DMSO-d$_6$) δ: 1.45-1.66 (4H, m), 1.87-1.95 (2H, m), 2.26-2.30 (3H, s), 2.38-2.70 (8H, m), 2.98-3.23 (3H, m), 3.77 (3H, s), 4.00-4.10 (1H, m), 4.60-4.70 (2H, m), 5.17-5.25 (1H, m), 6.85-6.88 (1H, m), 6.92-6.95 (1H, m).
ESI-MS: m/z=336 (M+H)$^+$.

Example 4—Synthesis of 1-((R)-3-(3-(dimethylamino)piperidin-1-yl)-3-hydroxy-3-(1-methyl-1H-imidazol-2-yl)propan-1-one

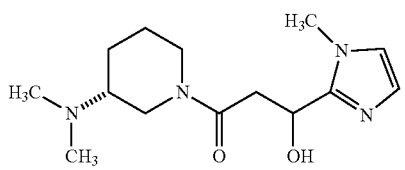 [SMILES: CN(C)[C@@H]1CCCN(C(=O)CC(O)c2nccn2C)C1]

Sodium borohydride (0.0210 g, 0.553 mmol) was added to a solution of (R)-1-(3-(dimethylamino)piperidin-1-yl)-3-(1-methyl-1H-imidazol-2-yl)propane-1,3-dione (0.140 g, 0.503 mmol) in ethanol (2.5 mL) at room temperature and the reaction liquid was stirred at the same temperature for 3 hours. A saturated aqueous solution of sodium hydrogencarbonate was added to the reaction liquid and the reaction liquid was concentrated under reduced pressure. Distilled water was added to the residue and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-((R)-3-(3-(dimethylamino)piperidin-1-yl)-3-hydroxy-3-(1-methyl-1H-imidazol-2-yl)propan-1-one (0.120 g, 0.428 mmol, 85%) (hereinafter referred to as the compound of Example 4) as a colorless oil.

$^1$H-NMR (400 MHz, DMSO-d$_6$) δ: 1.33-1.43 (1H, m), 1.57-1.90 (1H, m), 2.14-2.24 (6H, m), 2.45-2.54 (4H, m), 2.75-3.06 (3H, m), 3.63-4.40 (5H, m), 4.99-5.08 (1H, m), 5.32-5.42 (1H, m), 6.70-6.73 (1H, m), 7.01-7.03 (1H, m).
ESI-MS: m/z=281 (M+H)$^+$.

Example 5—Synthesis of 1-((R)-3-(dimethylamino)pyrrolidin-1-yl)-3-hydroxy-3-(1-methyl-1H-imidazol-2-yl)propan-1-one

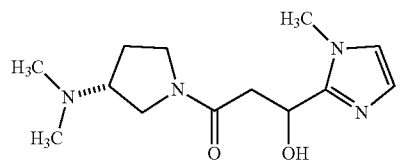 [SMILES: CN(C)[C@@H]1CCN(C(=O)CC(O)c2nccn2C)C1]

Sodium borohydride (0.0350 g, 0.916 mmol) was added to a solution of (R)-1-(3-(dimethylamino)pyrrolidin-1-yl)-3-(1-methyl-1H-imidazol-2-yl)propane-1,3-dione (0.220 g, 0.832 mmol) in ethanol (4.2 mL) at room temperature and the reaction liquid was stirred at the same temperature for 3 hours. A saturated aqueous solution of sodium hydrogencarbonate was added to the reaction liquid and the reaction liquid was concentrated under reduced pressure. Distilled water was added to the residue and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (silica gel, chloroform/methanol) to obtain 1-((R)-3-(dimethylamino)pyrrolidin-1-yl)-3-hydroxy-3-(1-methyl-1H-imidazol-2-yl)propan-1-one (0.209 g, 0.785 mmol, 94%) (hereinafter referred to as the compound of Example 5) as a colorless oil.

$^1$H-NMR (400 MHz, DMSO-d$_6$) δ: 1.50-1.78 (1H, m), 1.93-2.18 (7H, m), 2.60-2.95 (3H, m), 3.05-3.80 (7H, m), 4.98-5.07 (1H, m), 5.38-5.43 (1H, m), 6.71-6.73 (1H, m), 7.02-7.04 (1H, m).
ESI-MS: m/z=267 (M+H)$^+$.

Example 6—Synthesis of 1-(4-(dimethylamino)piperidin-1-yl)-3-hydroxy-3-(1-methyl-1H-imidazol-2-yl)propan-1-one

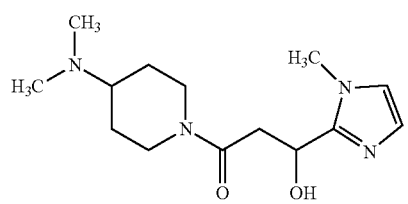 [SMILES: CN(C)C1CCN(C(=O)CC(O)c2nccn2C)CC1]

A solution of lithium diisopropylamide in tetrahydrofuran (2.0 M, 0.162 mL, 0.323 mmol) was added dropwise to a solution of 1-(4-(dimethylamino)piperidin-1-yl)ethanone (0.0500 g, 0.294 mmol) in tetrahydrofuran (0.8 mL) at −78° C. and the reaction liquid was stirred at the same temperature for 1 hour. A solution of 1-methyl-1H-imidazole-2- carbaldehyde (0.0390 g, 0.352 mmol) in tetrahydrofuran (0.4 mL) was added to the reaction liquid at the same temperature. The reaction liquid was stirred for 1 hour and then stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (silica gel, chloroform/methanol) to obtain 1-(4-(dimethylamino)piperidin-1-yl)-3-hydroxy-3-(1-methyl-1H-imidazol-2-yl)propan-1-one (0.0220 g, 0.0785 mmol, 27%) as a colorless oil.

$^1$H-NMR (400 MHz, CDCl$_3$) δ: 1.32-1.53 (2H, m), 1.82-1.92 (2H, m), 2.27-2.41 (7H, m), 2.60-2.72 (1H, m), 2.98-3.23 (3H, m), 3.77 (3H, s), 3.99-4.08 (1H, m), 4.58-4.82 (2H, m), 5.18-5.26 (1H, m), 6.86 (1H, s), 6.93 (1H, s).

ESI-MS: m/z=281 (M+H)$^+$.

Example 7—Synthesis of 1-(4-(dimethylamino)piperidin-1-yl)-3-hydroxy-3-(1-methyl-1H-imidazol-2-yl)propan-1-one hydrochloride

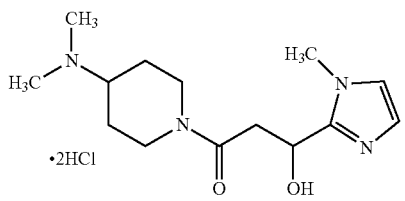 [SMILES: CN(C)C1CCN(C(=O)CC(O)c2nccn2C)CC1]

Hydrochloric acid (1.0 N, 0.086 mL, 0.086 mmol) was added to a solution of 1-(4-(dimethylamino)piperidin-1-yl)-3-hydroxy-3-(1-methyl-1H-imidazol-2-yl)propan-1-one (0.0220 g, 0.0785 mmol) in water (0.156 mL) at 0° C. and the reaction liquid was stirred at room temperature for 15 hours. The reaction liquid was concentrated under reduced pressure and dried at room temperature to obtain 1-(4-(dimethylamino)piperidin-1-yl)-3-hydroxy-3-(1-methyl-1H-imidazol-2-yl)propan-1-one hydrochloride (0.0220 g, 0.0623 mmol, 79%) (hereinafter referred to as the compound of Example 7) as a white solid.

$^1$H-NMR (400 MHz, D$_2$O) δ: 1.40-1.70 (2H, m), 1.98-2.10 (2H, m), 2.55-2.68 (1H, m), 2.72-2.77 (7H, m), 2.95-3.13 (3H, m), 3.36-3.45 (1H, m), 3.76 (3H, s), 3.97-4.06 (1H, m), 4.38-4.48 (1H, m), 6.40-6.47 (1H, m), 7.24-7.28 (2H, m).

ESI-MS: m/z=281 (M+H)$^+$.

Example 8—Synthesis of 1-(4-(dimethylamino)piperidin-1-yl)-3-(1-ethyl-1H-imidazol-2-yl)-3-hydroxypropan-1-one

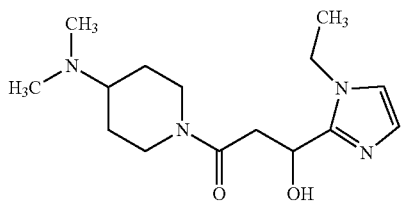 [SMILES: CCn1ccnc1C(O)CC(=O)N1CCC(N(C)C)CC1]

A solution of lithium diisopropylamide in tetrahydrofuran (2.0 M, 0.969 mL, 1.94 mmol) was added dropwise to a solution of 1-(4-(dimethylamino)piperidin-1-yl)ethanone (0.300 g, 1.76 mmol) in tetrahydrofuran (6.0 mL) at −78° C. and the reaction liquid was stirred at the same temperature for 1 hour. A solution of 1-ethyl-1H-imidazole-2-carbaldehyde (0.262 g, 2.12 mmol) in tetrahydrofuran (2.8 mL) was added to the reaction liquid. The reaction liquid was stirred for 1 hour and then stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)-3-(1-ethyl-1H-imidazol-2-yl)-3-hydroxypropan-1-one (0.221 g, 0.751 mmol, 43%) (hereinafter referred to as the compound of Example 8) as a colorless oil.

$^1$H-NMR (400 MHz, DMSO-d$_6$) δ: 1.04-1.21 (1H, m), 1.32 (4H, t, J=7.2 Hz), 1.62-1.80 (2H, m), 2.15 (6H, s), 2.24-2.35 (1H, m), 2.42-2.59 (1H, m), 2.76-2.88 (1H, m), 2.95-3.13 (2H, m), 3.90-4.08 (3H, m), 4.27-4.35 (1H, m), 5.00-5.10 (1H, m), 5.38-5.42 (1H, m), 6.74 (1H, s), 7.10 (1H, s).

ESI-MS: m/z=295 (M+H)$^+$.

Example 9—Synthesis of 1-(4-(dimethylamino)piperidin-1-yl)-3-hydroxy-3-(1-(2,2,2-trifluoroethyl)-1H-imidazol-2-yl)propan-1-one

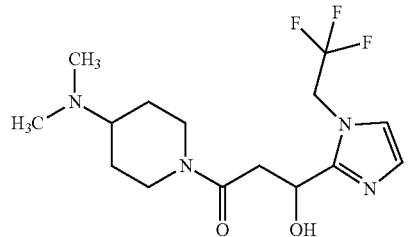 [SMILES: CN(C)C1CCN(C(=O)CC(O)c2nccn2CC(F)(F)F)CC1]

A solution of lithium diisopropylamide in tetrahydrofuran (2.0 M, 0.862 mL, 1.72 mmol) was added dropwise to a solution of 1-(4-(dimethylamino)piperidin-1-yl)ethanone (0.267 g, 1.57 mmol) in tetrahydrofuran (6.0 mL) at −78° C. and the reaction liquid was stirred at the same temperature for 1 hour. A solution of 1-(2,2,2-trifluoroethyl)-1H-imidazole-2-carbaldehyde (0.335 g, 1.88 mmol) in tetrahydrofuran (1.9 mL) was added to the reaction liquid at the same temperature and stirred for 1 hour and stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)-3-hydroxy-3-(1-(2,2,2-trifluoroethyl)-1H-imidazol-2-yl)propan-1-one (0.192 g, 0.551 mmol, 35%) (hereinafter referred to as the compound of Example 9) as a colorless oil.

$^1$H-NMR (400 MHz, DMSO-$d_6$) δ: 1.10-1.41 (2H, m), 1.64-1.80 (2H, m), 2.16 (6H, s), 2.25-2.37 (1H, m), 2.47-2.60 (1H, m), 2.80-3.12 (3H, m), 3.90-4.00 (1H, m), 4.29-4.39 (1H, m), 5.00-5.18 (3H, m), 5.60-5.68 (1H, m), 6.85 (1H, s), 7.17 (1H, s).

ESI-MS: m/z=349 (M+H)$^+$.

Example 10—Synthesis of 3-(1-(difluoromethyl)-1H-imidazol-2-yl)-1-(4-(dimethylamino)piperidin-1-yl)-3-hydroxypropan-1-one

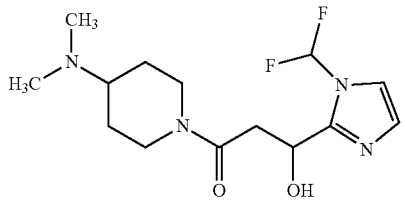 [SMILES: CN(C)C1CCN(C(=O)CC(O)c2nccn2C(F)F)CC1]

Sodium borohydride (0.0560 g, 1.48 mmol) was added to a solution of 1-(1-(difluoromethyl)-1H-imidazol-2-yl)-3-(4-(dimethylamino)piperidin-1-yl)propane-1,3-dione (0.310 g, 0.986 mmol) in methanol (10 mL) at room temperature and the reaction liquid was stirred at the same temperature for 3 hours. A saturated aqueous solution of sodium hydrogencarbonate was added to the reaction liquid and the reaction liquid was concentrated under reduced pressure. Distilled water was added to the residue and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 3-(1-(difluoromethyl)-1H-imidazol-2-yl)-1-(4-(dimethylamino)piperidin-1-yl)-3-hydroxypropan-1-one (0.202 g, 0.639 mmol, 65%) (hereinafter referred to as the compound of Example 10) as a yellow oil.

$^1$H-NMR (400 MHz, CDCl$_3$) δ: 1.08-1.40 (2H, m), 1.64-1.80 (2H, m), 2.17 (6H, s), 2.25-2.35 (1H, m), 2.49-2.62 (1H, m), 2.80-3.12 (3H, m), 3.88-3.97 (1H, m), 4.28-4.37 (1H, m), 5.18-5.26 (1H, m), 5.83 (1H, d, J=6.8 Hz), 6.95 (1H, s), 7.51 (1H, s), 7.93 (1H, t, J=60.0 Hz).

ESI-MS: m/z=317 (M+H)$^+$.

Example 11—Synthesis of (S)-1-(4-(dimethylamino)piperidin-1-yl)-3-hydroxy-3-(1-methyl-1H-imidazol-2-yl)propan-1-one

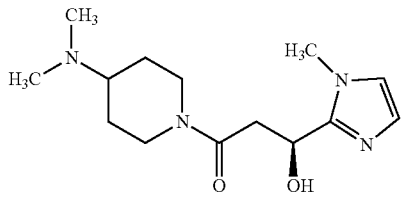 [SMILES: CN(C)C1CCN(C(=O)C[C@H](O)c2nccn2C)CC1]

Optical resolution of 1-(4-(dimethylamino)piperidin-1-yl)-3-hydroxy-3-(1-methyl-1H-imidazol-2-yl)propan-1-one (3.32 g) was performed by HPLC purification. The eluate was concentrated under reduced pressure. The residue was purified by flash column chromatography (NH silica gel, chloroform/methanol) to obtain (S)-1-(4-(dimethylamino)piperidin-1-yl)-3-hydroxy-3-(1-methyl-1H-imidazol-2-yl)propan-1-one (0.467 g, >99% ee) (hereinafter referred to as the compound of Example 11) as a white solid.

HPLC retention time: 8.4 min; apparatus: LC-10ADvp system manufactured by Shimadzu Corporation; column: CHIRALCEL OZ-H, 4.6×250 mm (manufactured by Daicel Corporation); Solvent: 0.01% ethylenediamine-containing methanol (v/v); flow rate: 0.5 mL/min; detection method: UV 220 nm; column temperature: 40° C.

$^1$H-NMR (400 MHz, CDCl$_3$) δ: 1.32-1.53 (2H, m), 1.82-1.92 (2H, m), 2.27-2.41 (7H, m), 2.60-2.72 (1H, m), 2.98-3.23 (3H, m), 3.77 (3H, s), 3.99-4.08 (1H, m), 4.58-4.82 (2H, m), 5.18-5.26 (1H, m), 6.86 (1H, s), 6.93 (1H, s).

ESI-MS: m/z=281 (M+H)$^+$.

Example 12—Synthesis of 3-(4-(dimethylamino)piperidin-1-yl)-1-(1-methyl-1H-imidazol-2-yl)-3-oxopropyl acetate

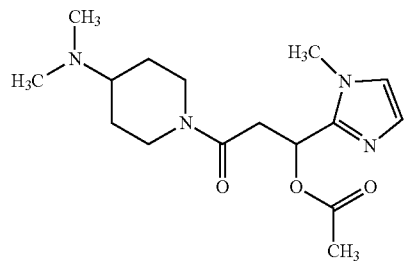 [SMILES: CC(=O)OC(CC(=O)N1CCC(N(C)C)CC1)c1nccn1C]

Pyridine (0.042 mL, 0.51 mmol) and acetic anhydride (0.042 mL, 0.51 mmol) were added to a solution of 1-(4-(dimethylamino)piperidin-1-yl)-3-hydroxy-3-(1-methyl-1H-imidazol-2-yl)propan-1-one (0.120 g, 0.428 mmol) in dichloromethane (2.1 mL) at 0° C. and the reaction liquid was stirred at room temperature for 2 hours. Further, acetic anhydride (0.020 mL, 0.24 mmol) was added at room temperature and the reaction liquid was stirred at the same temperature for 1 hour. A saturated aqueous solution of sodium hydrogencarbonate was added to the reaction liquid and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 3-(4-(dimethylamino)piperidin-1-yl)-1-(1-methyl-1H-imidazol-2-yl)-3-oxopropyl acetate (0.114 g, 0.353 mmol, 82%) (hereinafter referred to as the compound of Example 12) as a colorless oil.

$^1$H-NMR (400 MHz, CDCl$_3$) δ: 1.08-1.47 (2H, m), 1.68-1.92 (2H, m), 2.04 (3H, dd, J=2.4 Hz), 2.21-2.38 (7H, m), 2.47-2.60 (1H, m), 2.96-3.14 (2H, m), 3.35-3.43 (1H, m), 3.83 (3H, d, J=4.0 Hz), 3.89-4.00 (1H, m), 4.45-4.53 (1H, m), 6.21-6.29 (1H, m), 6.79 (1H, m), 6.98 (1H, m).

ESI-MS: m/z=323 (M+H)$^+$.

Example 13—Synthesis of 3-(4-(dimethylamino)piperidin-1-yl)-1-(1-methyl-1H-imidazol-2-yl)-3-oxopropylpentanoate

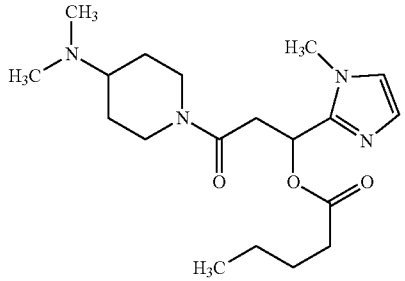 [SMILES: CCCCC(=O)OC(CC(=O)N1CCC(N(C)C)CC1)c1nccn1C]

Pyridine (0.069 mL, 0.86 mmol) and pentanoyl chloride (0.093 mL, 0.79 mmol) were added to a solution of 1-(4-(dimethylamino)piperidin-1-yl)-3-hydroxy-3-(1-methyl-1H-imidazol-2-yl)propan-1-one (0.200 g, 0.713 mmol) in dichloromethane (3.5 mL) at room temperature and the reaction liquid was stirred at the same temperature for 16 hours. A saturated aqueous solution of ammonium chloride was added to the reaction liquid and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 3-(4-(dimethylamino)piperidin-1-yl)-1-(1-methyl-1H-imidazol-2-yl)-3-oxopropylpentanoate (0.101 g, 0.277 mmol, 39%) (hereinafter referred to as the compound of Example 13) as a colorless oil.

$^1$H-NMR (400 MHz, DMSO-d$_6$) δ: 0.77-0.85 (3H, m), 0.98-1.33 (4H, m), 1.41-1.50 (2H, m), 1.60-1.79 (2H, m), 2.11-2.15 (6H, m), 2.20-2.33 (3H, m), 2.89-3.02 (2H, m), 3.22-3.34 (2H, m), 3.65 (3H, s), 3.84-3.92 (1H, m), 4.18-4.26 (1H, m), 6.10-6.15 (1H, m), 6.77-6.82 (1H, m), 7.05-7.10 (1H, m).

ESI-MS: m/z=365 (M+H)$^+$.

In the following Comparative Examples, 1-(4-(dimethylamino)piperidin-1-yl)-3-(1-methyl-1H-imidazol-2-yl)propan-1-one hydrochloride (the compound of Comparative Example 1); 1-(4-(dimethylamino)piperidin-1-yl)-3-(1-methyl-1H-imidazol-2-yl)propan-1-one sulfate monohydrate (the compound of Comparative Example 2); 1-(4-(dimethylamino)piperidin-1-yl)-3-(1-ethyl-1H-imidazol-2-yl)propan-1-one hydrochloride (the compound of Comparative Example 3); 1-(4-(dimethylamino)piperidin-1-yl)-3-(1-propyl-1H-imidazol-2-yl)propan-1-one hydrochloride (the compound of Comparative Example 4); 1-(4-(dimethylamino)piperidin-1-yl)-3-(1-butyl-1H-imidazol-2-yl)propan-1-one hydrochloride (the compound of Comparative Example 5); and 1-(4-(dimethylamino)piperidin-1-yl)-3-(1-isopropyl-1H-imidazol-2-yl)propan-1-one hydrochloride (the compound of Comparative Example 6) were selected from imidazole derivatives described in International Publication WO No. 2013/147160 as suitable comparative compounds.

The compounds of Comparative Examples 1 to 6 were prepared in the same manner as described in International Publication WO No. 2013/147160, as follows.

Reference Example 18—Synthesis of 1-propyl-1H-imidazole

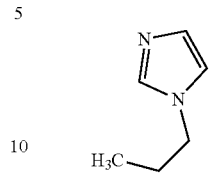

Sodium hydride (55%, 0.966 g, 22.1 mmol) was added to a solution of imidazole (1.37 g, 20.1 mmol) in tetrahydrofuran (50.0 mL) at room temperature. The reaction liquid was stirred at the same temperature for 1 hour, and then, 1-bromopropane (5.48 mL, 60.3 mmol) was added at room temperature. The reaction liquid was stirred at the same temperature for 16 hours. The reaction liquid was filtered through Celite and washed with tetrahydrofuran, and then the filtrate and the washing solution were concentrated under reduced pressure. The residue was purified by flash column chromatography (silica gel, chloroform/methanol) to obtain 1-propylimidazole (2.07 g, 18.8 mmol, 93%) as a colorless oil.

1H-NMR (400 MHz, CDCl$_3$) δ: 0.93 (3H, t, J=7.2 Hz), 1.81 (2H, td, J=7.2, 14.4 Hz), 3.90 (2H, t, J=7.2 Hz), 6.91 (1H, s), 7.06 (1H, s), 7.46 (1H, s).

Reference Example 19—Synthesis of 1-propyl-1H-imidazole-2-carbaldehyde

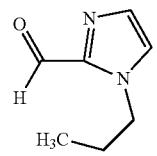

A solution of 1-propyl-1H-imidazole (1.67 g, 15.2 mmol) in tetrahydrofuran (30.4 mL) was cooled to −78° C. n-Butyllithium (1.62 M n-hexane solution, 10.3 mL, 16.7 mmol) was added to the reaction liquid at −78° C. The reaction liquid was stirred at the same temperature for 1 hour and then N,N-dimethylformamide (1.41 mL, 18.2 mmol) was added at −78° C. After the reaction liquid was stirred at the same temperature for 1 hour, the temperature of the reaction liquid was raised to room temperature. A saturated aqueous solution of ammonium chloride was added to the reaction liquid and then ethyl acetate was added. The organic layer was washed with a 10% aqueous solution of sodium chloride and then dried over anhydrous sodium sulfate and filtered. The filtrate was concentrated under reduced pressure. The residue was purified by flash column chromatography (silica gel, n-hexane/ethyl acetate) to obtain 1-propyl-1H-imidazole-2-carbaldehyde (0.492 g, 3.56 mmol, 24%) as a colorless oil.

$^1$H-NMR (400 MHz, CDCl$_3$) δ: 0.91-0.95 (3H, m), 1.79-1.84 (2H, m), 4.34-4.38 (2H, m), 7.15 (1H, s), 7.28 (1H, s), 9.82 (1H, s).

ESI-MS: m/z=139 (M+H)$^+$.

Reference Example 20—Synthesis of 1-butyl-1H-imidazole-2-carbaldehyde

A solution of 1-butyl-1H-imidazole (1.00 g, 8.05 mmol) in tetrahydrofuran (16.1 mL) was cooled to −78° C. n-Butyllithium (1.62 M n-hexane solution, 5.5 mL, 8.86 mmol) was added to the reaction liquid at −78° C. The reaction liquid was stirred at the same temperature for 1 hour and then N,N-dimethylformamide (0.75 mL, 9.66 mmol) was added at −78° C. After the reaction liquid was stirred at the same temperature for 1 hour, the temperature of the reaction liquid was raised to room temperature. A saturated aqueous solution of ammonium chloride was added to the reaction liquid and then ethyl acetate was added. The organic layer was washed with a 10% aqueous solution of sodium chloride and then dried over anhydrous sodium sulfate and filtered. The filtrate was concentrated under reduced pressure. The residue was purified by flash column chromatography (silica gel, n-hexane/ethyl acetate) to obtain 1-butyl-1H-imidazole-2-carbaldehyde (1.02 g, 6.70 mmol, 83%) as a colorless oil.

$^1$H-NMR (400 MHz, CDCl$_3$) δ: 0.95 (3H, t, J=7.2 Hz), 1.33 (2H, td, J=7.2, 14.8 Hz), 1.75-1.78 (2H, m), 4.34 (2H, t, J=7.2 Hz), 7.15 (1H, s), 7.28 (1H, s), 9.81 (1H, s).

ESI-MS: m/z=153 (M+H)$^+$.

Reference Example 21—Synthesis of 1-isopropyl-1H-imidazole-2-carbaldehyde

Potassium carbonate (0.863 g, 6.24 mmol) and 2-iodopropane (0.614 mL, 6.24 mmol) were added to a solution of 1H-imidazole-2-carbaldehyde (0.500 g, 5.20 mmol) in N,N-dimethylformamide (5.2 mL) at room temperature and the reaction liquid was stirred at 60° C. for 4 hours. The reaction liquid was cooled to room temperature and ethyl acetate and distilled water were added to the reaction liquid. The organic layer was washed with a 10% aqueous solution of sodium chloride and then dried over anhydrous sodium sulfate and filtered. The filtrate was concentrated under reduced pressure. The residue was purified by flash column chromatography (silica gel, n-hexane/ethyl acetate) to obtain 1-isopropyl-1H-imidazole-2-carbaldehyde (0.355 g, 2.57 mmol, 49%) as a colorless oil.

$^1$H-NMR (400 MHz, CDCl$_3$) δ: 1.48 (3H, d, J=6.4 Hz), 1.48 (3H, d, J=6.4 Hz), 5.48 (1H, quint, J=6.4 Hz), 7.30 (1H, s), 7.33 (1H, s), 9.83 (1H, s).

ESI-MS: m/z=139 (M+H)$^+$.

Reference Example 22—Synthesis of (E)-methyl 3-(1-methyl-1H-imidazol-2-yl)acrylate

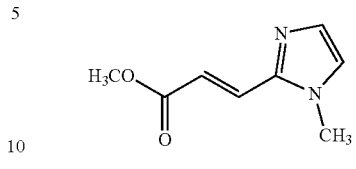

Methyl (triphenylphosphoranylidene)acetate (33.4 g, 99.9 mmol) was added to a solution of 1-methyl-1H-imidazole-2-carbaldehyde (10.0 g, 90.8 mmol) in dichloromethane (240 mL) at room temperature. The reaction liquid was stirred for 16 hours and then concentrated under reduced pressure. The residue was washed with a mixed solvent of hexane/dichloromethane=19/1 and the washing solution was concentrated. The residue was purified by a silica gel column chromatography (hexane/ethyl acetate) to obtain (E)-methyl 3-(1-methyl-1H-imidazol-2-yl)acrylate (11.9 g, 71.6 mmol, 79%) as a white solid.

$^1$H-NMR (400 MHz, CDCl$_3$) δ: 3.76 (3H, s), 3.81 (3H, s), 6.82 (1H, d, J=15.6 Hz), 6.98 (1H, brs), 7.16 (1H, brs), 7.53 (1H, d, J=15.6 Hz).

ESI-MS: m/z=167 (M+H)$^+$.

Reference Example 23—Synthesis of (E)-methyl 3-(1-ethyl-1H-imidazol-2-yl)acrylate

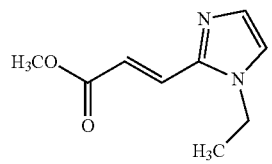

Methyl (triphenylphosphoranylidene)acetate (3.15 g, 9.42 mmol) was added to a solution of 1-ethyl-1H-imidazole-2-carbaldehyde (1.17 g, 9.42 mmol) in dichloromethane (28.3 mL) at room temperature. The reaction liquid was stirred for 16 hours and concentrated under reduced pressure. The residue was washed with a mixed solvent of hexane/dichloromethane=20/1 and the washing solution was concentrated. The residue was purified by flash column chromatography (silica gel, hexane/ethyl acetate) to obtain (E)-methyl 3-(1-ethyl-1H-imidazol-2-yl)acrylate (0.670 g, 3.72 mmol, 39%) as a white solid.

$^1$H-NMR (400 MHz, CDCl$_3$) δ: 1.45 (3H, t, J=7.6 Hz), 3.81 (3H, s), 4.10 (2H, dd, J=7.6, 14.8 Hz), 6.85 (1H, d, J=15.2 Hz), 7.03 (1H, brs), 7.17 (1H, brs), 7.52 (1H, d, J=15.2 Hz).

ESI-MS: m/z=181 (M+H)$^+$.

Reference Example 24—Synthesis of (E)-methyl 3-(1-propyl-1H-imidazol-2-yl)acrylate

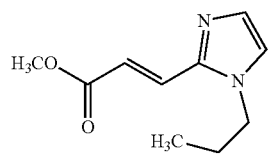

Methyl (triphenylphosphoranylidene)acetate (1.31 g, 3.92 mmol) was added to a solution of 1-propyl-1H-imidazole-2-carbaldehyde (0.492 g, 3.56 mmol) in dichloromethane (10.0 mL) at room temperature. The reaction liquid was stirred for 16 hours and then concentrated under reduced pressure. The residue was washed with a mixed solvent of hexane/dichloromethane=19/1 and the washing solution was concentrated. The residue was purified by flash column chromatography (silica gel, hexane/ethyl acetate) to obtain (E)-methyl 3-(1-propyl-1H-imidazole-2-yl)acrylate (0.520 g, 2.68 mmol, 75%) as a white solid.

$^1$H-NMR (400 MHz, CDCl$_3$) δ: 0.94 (3H, t, J=7.2 Hz), 1.75-1.85 (2H, m), 3.81 (3H, s), 4.00 (2H, t, J=7.2 Hz), 6.85 (1H, d, J=15.6 Hz), 7.00 (1H, brs), 7.16 (1H, brs), 7.50 (1H, d, J=15.6 Hz).

ESI-MS: m/z=195 (M+H)$^+$.

Reference Example 25—Synthesis of (E)-methyl 3-(1-butyl-1H-imidazol-2-yl)acrylate

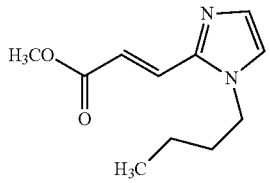

Methyl (triphenylphosphoranylidene)acetate (2.47 g, 7.37 mmol) was added to a solution of 1-butyl-1H-imidazole-2-carbaldehyde (1.02 g, 6.70 mmol) in dichloromethane (18.0 mL) at room temperature. The reaction liquid was stirred for 16 hours and then concentrated under reduced pressure. The residue was washed with a mixed solvent of hexane/dichloromethane=19/1 and the washing solution was concentrated. The residue was purified by flash column chromatography (silica gel, hexane/ethyl acetate) to obtain (E)-methyl 3-(1-butyl-1H-imidazol-2-yl)acrylate (1.23 g, 5.91 mmol, 88%) as a white solid.

$^1$H-NMR (400 MHz, CDCl$_3$) δ: 0.95 (3H, t, J=7.2 Hz), 1.28-1.40 (2H, m), 1.70-1.80 (2H, m), 3.81 (3H, s), 4.03 (2H, t, J=7.2 Hz), 6.84 (1H, d, J=15.2 Hz), 7.00 (1H, brs), 7.16 (1H, brs), 7.50 (1H, d, J=15.2 Hz).

ESI-MS: m/z=209 (M+H)$^+$.

Reference Example 26—Synthesis of (E)-methyl 3-(1-isopropyl-1H-imidazol-2-yl)acrylate

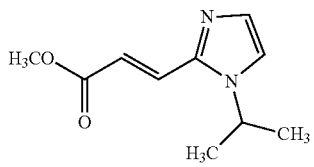

Methyl (triphenylphosphoranylidene)acetate (0.932 g, 2.79 mmol) was added to a solution of 1-isopropyl-1H-imidazole-2-carbaldehyde (0.350 mg, 2.53 mmol) in dichloromethane (7.59 mL) at room temperature. The reaction liquid was stirred for 16 hours and then concentrated under reduced pressure. The residue was washed with a mixed solvent of hexane/dichloromethane=20/1 and the washing solution was concentrated. The residue was purified by flash column chromatography (silica gel, hexane/ethyl acetate) to obtain (E)-methyl 3-(1-isopropyl-1H-imidazol-2-yl)acrylate (0.362 g, 1.86 mmol, 74%) as a white solid.

$^1$H-NMR (400 MHz, CDCl$_3$) δ: 1.50 (3H, d, J=6.4 Hz), 1.50 (3H, d, J=6.4 Hz), 3.81 (3H, s), 4.62 (1H, quint, J=6.4 Hz), 6.87 (1H, d, J=15.6 Hz), 7.10 (1H, brs), 7.18 (1H, brs), 7.56 (1H, d, J=15.6 Hz).

ESI-MS: m/z=195 (M+H)$^+$.

Reference Example 27—Synthesis of 1-(4-(dimethylamino)piperidin-1-yl)-3-(1-methyl-1H-imidazol-2-yl)propan-1-one

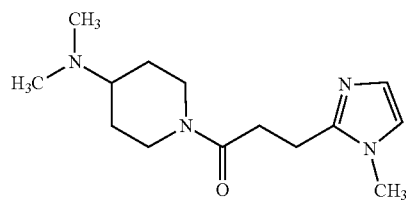 [SMILES: CN(C)C1CCN(C(=O)CCc2nccn2C)CC1]

Palladium-carbon (10% wet, 15 mg) was added to a solution of (E)-methyl 3-(1-methyl-1H-imidazol-2-yl)acrylate (0.180 g, 1.08 mmol) in ethanol (4.0 mL) at room temperature. The reaction liquid was stirred under a hydrogen atmosphere for 4 hours. The reaction liquid was filtered through Celite and the filtrate was concentrated under reduced pressure. Methanol (1.0 mL) was added to the resulting residue at room temperature to dissolve the residue and the reaction liquid was cooled to 0° C. An aqueous solution of sodium hydroxide (1.0 N, 1.19 mL, 1.19 mmol) was added to the reaction liquid at 0° C. The reaction liquid was stirred at room temperature for 2 hours and then concentrated under reduced pressure. Chloroform (10.0 mL) was added to the resulting residue at room temperature to dissolve the residue. Diisopropylethylamine (0.568 mL, 3.25 mmol), HBTU (0.616 g, 1.63 mmol) and 4-(dimethylamino)piperidine (0.125 g, 0.975 mmol) were added to the reaction liquid at room temperature and the reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)-3-(1-methyl-1H-imidazol-2-yl)propan-1-one (0.179 g, 0.68 mmol, 63%) as a colorless oil.

$^1$H-NMR (400 MHz, CDCl$_3$) δ: 1.29-1.43 (2H, m), 1.80-1.88 (2H, m), 2.27 (6H, s), 2.29-2.38 (1H, m), 2.54-2.63 (1H, m), 2.88-3.04 (5H, m), 3.62 (3H, s), 3.98-4.05 (1H, m), 4.57-4.65 (1H, m), 6.79 (1H, d, J=1.2 Hz), 6.91 (1H, d, J=1.2 Hz).

ESI-MS: m/z=265 (M+H)$^+$.

Reference Example 28—Synthesis of 1-(4-(dimethylamino)piperidin-1-yl)-3-(1-ethyl-1H-imidazol-2-yl)propan-1-one

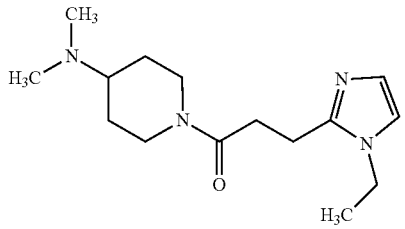 [SMILES: CCn1ccnc1CCC(=O)N1CCC(N(C)C)CC1]

Palladium-carbon (10% wet, 65 mg) was added to a solution of (E)-methyl 3-(1-ethyl-1H-imidazol-2-yl)acrylate (0.670 g, 3.71 mmol) in methanol (14.8 mL) at room temperature and the reaction liquid was stirred under a hydrogen atmosphere for 16 hours. The reaction liquid was filtered through Celite and the filtrate was concentrated under reduced pressure. Methanol (3.70 mL) was added to the resulting residue at room temperature to dissolve the residue and the reaction liquid was cooled to 0° C. An aqueous solution of sodium hydroxide (1.0 N, 4.07 mL, 4.07 mmol) was added to the reaction liquid at 0° C. and the reaction liquid was stirred at room temperature for 16 hours and then concentrated under reduced pressure. Chloroform (37.0 mL) was added to the resulting residue at room temperature to dissolve the residue. Diisopropylethylamine (1.94 mL, 11.1 mmol), HBTU (2.10 g, 5.54 mmol) and 4-(dimethylamino)piperidine (0.427 g, 3.33 mmol) were added to the reaction liquid at room temperature and the reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)-3-(1-ethyl-1H-imidazol-2-yl)propan-1-one (0.365 g, 1.31 mmol, 35%) as a colorless oil.

$^1$H-NMR (400 MHz, CDCl$_3$) δ: 1.32-1.40 (5H, m), 1.83-1.87 (2H, m), 2.27 (6H, s), 2.31-2.37 (1H, m), 2.56-2.63 (1H, m), 2.93-2.98 (5H, m), 3.93-4.04 (3H, m), 4.01-4.04 (1H, m), 6.84 (1H, d, J=1.6 Hz), 6.94 (1H, d, J=1.6 Hz).
ESI-MS: m/z=279 (M+H)$^+$.

Reference Example 29—Synthesis of 1-(4-(dimethylamino)piperidin-1-yl)-3-(1-propyl-1H-imidazol-2-yl)propan-1-one

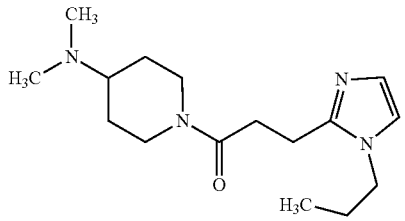 [SMILES: CCCn1ccnc1CCC(=O)N1CCC(N(C)C)CC1]

Palladium-carbon (10% wet, 19 mg) was added to a solution of (E)-methyl 3-(1-propyl-1H-imidazole-2-yl)acrylate (260 mg, 1.34 mmol) in methanol (5.0 mL) at room temperature and the reaction liquid was stirred under a hydrogen atmosphere for 4 hours. The reaction liquid was filtered through Celite and the filtrate was concentrated under reduced pressure. Methanol (1.50 mL) was added to the resulting residue at room temperature to dissolve the residue and the reaction liquid was cooled to 0° C. An aqueous solution of sodium hydroxide (1.0 N, 1.47 mL, 1.47 mmol) was added to the reaction liquid at 0° C. The reaction liquid was stirred at room temperature for 4 hours and then concentrated under reduced pressure. Chloroform (16.0 mL) was added to the resulting residue at room temperature to dissolve the residue. Diisopropylethylamine (0.863 mL, 4.94 mmol), HBTU (0.937 g, 2.47 mmol) and 4-(dimethylamino)piperidine (0.190 g, 1.48 mmol) were added to the reaction liquid at room temperature and the reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)-3-(1-propyl-1H-imidazol-2-yl)propan-1-one (110 mg, 0.376 mmol, 28%) as a colorless oil.

$^1$H-NMR (400 MHz, CDCl$_3$) δ: 0.93 (3H, t, J=7.2 Hz), 1.30-1.43 (2H, m), 1.71-1.88 (4H, m), 2.27 (6H, s), 2.28-2.39 (1H, m), 2.55-2.64 (1H, m), 2.90-3.05 (5H, m), 3.86 (2H, t, J=7.2 Hz), 4.00-4.09 (1H, m), 4.58-4.66 (1H, m), 6.82 (1H, d, J=1.6 Hz), 6.93 (1H, d, J=1.6 Hz).
ESI-MS: m/z=293 (M+H)$^+$.

Reference Example 30—Synthesis of 1-(4-(dimethylamino)piperidin-1-yl)-3-(1-butyl-1H-imidazol-2-yl)propane-1-one

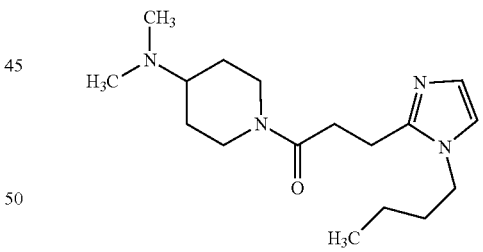

Palladium-carbon (10% wet, 19 mg) was added to a solution of (E)-methyl 3-(1-butyl-1H-imidazol-2-yl)acrylate (260 mg, 1.25 mmol) in ethanol (5.0 mL) at room temperature and the reaction liquid was stirred under a hydrogen atmosphere for 4 hours. The reaction liquid was filtered through Celite and the filtrate was concentrated under reduced pressure. Methanol (1.5 mL) was added to the resulting residue at room temperature to dissolve the residue and the reaction liquid was cooled to 0° C. An aqueous solution of sodium hydroxide (1.0 N, 1.47 mL, 1.47 mmol) was added to the reaction liquid at 0° C. The reaction liquid was stirred at room temperature for 4 hours and then concentrated under reduced pressure. Chloroform (15.0 mL) was added to the resulting residue at room temperature to dissolve the residue. Diisopropylethylamine (0.801 mL, 4.59 mmol), HBTU (0.870 g, 2.29 mmol) and 4-(dimethylamino)piperidine (0.176 g, 1.38 mmol) were added to the reaction liquid at room temperature and the reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)-3-(1-butyl-1H-imidazol-2-yl)propane-1-one (120 mg, 0.392 mmol, 31%) as a colorless oil.

$^1$H-NMR (400 MHz, CDCl$_3$) δ: 0.93 (3H, t, J=7.2 Hz), 1.29-1.43 (4H, m), 1.65-1.74 (2H, m), 1.78-1.88 (2H, m), 2.25-2.37 (7H, m), 2.54-2.64 (1H, m), 2.88-3.04 (5H, m), 3.88 (2H, t, J=7.2 Hz), 3.98-4.06 (1H, m), 4.56-4.66 (1H, m), 6.81 (1H, brs), 6.92 (1H, brs).

ESI-MS: m/z=307 (M+H)$^+$.

Reference Example 31—Synthesis of 1-(4-(dimethylamino)piperidin-1-yl)-3-(1-isopropyl-1H-imidazol-2-yl)propan-1-one

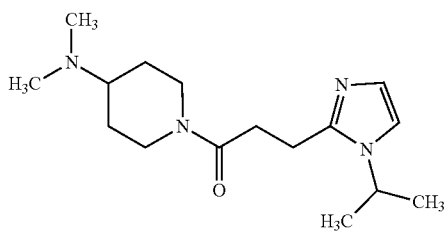 [SMILES: CC(C)n1ccnc1CCC(=O)N1CCC(N(C)C)CC1]

Palladium-carbon (10% wet, 36 mg) was added to a solution of (E)-methyl 3-(1-isopropyl-1H-imidazol-2-yl) acrylate (362 mg, 1.86 mmol) in methanol (7.46 mL) at room temperature and the resultant mixture was stirred under a hydrogen atmosphere for 16 hours. The reaction liquid was filtered through Celite and the filtrate was concentrated under reduced pressure. Methanol (1.86 mL) was added to the resulting residue at room temperature to dissolve the residue and the reaction liquid was cooled to 0° C. An aqueous solution of sodium hydroxide (1.0 N, 2.05 mL, 2.05 mmol) was added to the reaction liquid at 0° C. The reaction liquid was stirred at room temperature for 16 hours and then concentrated under reduced pressure. Chloroform (18.6 mL) was added to the resulting residue at room temperature to dissolve the residue. Diisopropylethylamine (0.976 mL, 5.59 mmol), HBTU (1.06 g, 2.80 mmol) and 4-(dimethylamino)piperidine (0.215 g, 1.68 mmol) were added to the reaction liquid at room temperature and the reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain 1-(4-(dimethylamino)piperidin-1-yl)-3-(1-isopropyl-1H-imidazol-2-yl)propan-1-one (335 mg, 1.15 mmol, 62%) as a colorless oil.

$^1$H-NMR (400 MHz, CDCl$_3$) δ: 1.32-1.42 (8H, m), 1.83-1.86 (2H, m), 2.27-2.34 (7H, m), 2.57-2.64 (1H, m), 2.96-3.02 (5H, m), 4.03-4.06 (1H, m), 4.42-4.49 (1H, m), 4.61-4.64 (1H, m), 6.91 (1H, brs), 6.95 (1H, brs).

ESI-MS: m/z=293 (M+H)$^+$.

Comparative Example 1—Synthesis of 1-(4-(dimethylamino)piperidin-1-yl)-3-(1-methyl-1H-imidazol-2-yl)propan-1-one hydrochloride

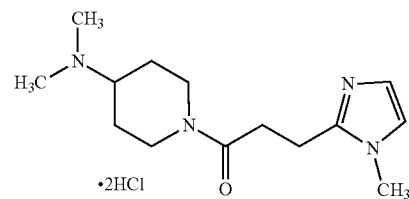 [SMILES: CN(C)C1CCN(C(=O)CCc2nccn2C)CC1]

A solution of hydrogen chloride in dioxane (4.0 M, 3.69 mL, 14.8 mmol) was added to a solution of 1-(4-(dimethylamino)piperidin-1-yl)-3-(1-methyl-1H-imidazol-2-yl)propan-1-one (1.50 g, 5.67 mmol) in diethyl ether (60.0 mL) at 0° C. The reaction liquid was stirred at the same temperature for 1 hour and stirred at room temperature for 30 minutes. The white solid precipitated was filtered and collected, washed with diethyl ether (100 mL) and dried at room temperature for 36 hours to obtain 1-(4-(dimethylamino) piperidin-1-yl)-3-(1-methyl-1H-imidazol-2-yl)propan-1-one hydrochloride (1.41 g, 4.18 mmol, 74%) (hereinafter referred to as the compound of Comparative Example 1) as a white solid.

$^1$H-NMR (400 MHz, D$_2$O) δ: 1.53-1.80 (2H, m), 2.12-2.23 (2H, m), 2.68-2.80 (1H, m), 2.88 (6H, s), 3.01-3.08 (2H, m), 3.15-3.26 (3H, m), 3.47-3.58 (1H, m), 3.84 (3H, s), 4.08-4.16 (1H, m), 4.50-4.59 (1H, m), 7.29-7.33 (2H, m).

ESI-MS; as 1-(4-(dimethylamino)piperidin-1-yl)-3-(1-methyl-1H-imidazol-2-yl)propan-1-one: m/z=265 (M+H)$^+$.

Comparative Example 2—Synthesis of 1-(4-(dimethylamino)piperidin-1-yl)-3-(1-methyl-1H-imidazol-2-yl)propan-1-one sulfate monohydrate

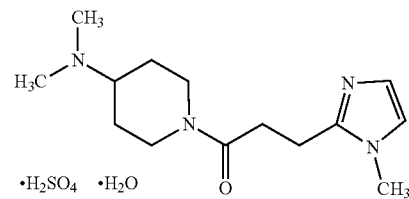 [SMILES: "·H2SO4" ; CN(C)C1CCN(C(=O)CCc2nccn2C)CC1 ; O]

Concentrated sulfuric acid (2.49 g, 25.4 mmol), water (1.83 g, 102 mmol) and a seed crystal (50 mg, 0.13 mmol) of 1-(4-(dimethylamino)piperidin-1-yl)-3-(1-methyl-1H-imidazol-2-yl)propan-1-one sulfate monohydrate were added to a solution of 1-(4-(dimethylamino)piperidin-1-yl)-3-(1-methyl-1H-imidazol-2-yl)propan-1-one (6.72 g, 25.4 mmol) in DMSO (100 mL) at 80° C. The reaction liquid was stirred at the same temperature for 2.5 hours, at 50° C. for 2.5 hours and at room temperature for 15 hours. The white solid precipitated was filtered and collected, washed sequentially with DMSO (20 mL) and methyl ethyl ketone (40 mL)

and dried at room temperature to obtain 1-(4-(dimethylamino)piperidin-1-yl)-3-(1-methyl-1H-imidazol-2-yl)propan-1-one sulfate monohydrate (8.42 g, 22.1 mmol, 87%) (hereinafter referred to as the compound of Comparative Example 2) as a white crystal.

$^1$H-NMR (400 MHz, DMSO-$d_6$) δ: 1.36 (1H, m), 1.58 (1H, m), 1.95 (2H, br), 2.44-2.57 (1H, m), 2.65 (6H, s), 2.74-2.88 (4H, m), 3.00 (1H, t, J=12.0 Hz), 3.22 (1H, m), 3.61 (3H, s), 4.02 (1H, d, J=14.0 Hz), 4.47 (1H, d, J=12.8 Hz), 6.87 (1H, d, J=1.2 Hz), 7.11 (1H, d, J=1.2 Hz).

ESI-MS; as 1-(4-(dimethylamino)piperidin-1-yl)-3-(1-methyl-1H-imidazol-2-yl)propan-1-one: m/z=265 (M+H)$^+$.

Comparative Example 3—Synthesis of 1-(4-(dimethylamino)piperidin-1-yl)-3-(1-ethyl-1H-imidazol-2-yl)propan-1-one hydrochloride

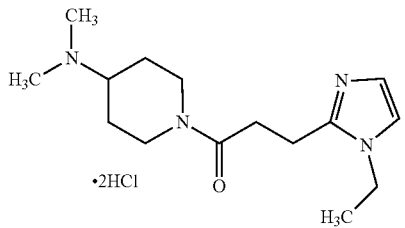 [SMILES: CCn1ccnc1CCC(=O)N1CCC(N(C)C)CC1]

A solution of hydrogen chloride in diethyl ether (2.0 N, 1.07 mL, 2.14 mmol) was added to a solution of 1-(4-(dimethylamino)piperidin-1-yl)-3-(1-ethyl-1H-imidazol-2-yl)propan-1-one (0.271 g, 0.973 mmol) in diethyl ether (19.5 mL) at 0° C. The reaction liquid was stirred at the same temperature for 1 hour and then stirred at room temperature for 30 minutes. The white solid precipitated was filtered and collected, washed with diethyl ether (58.5 mL) and dried at room temperature for 36 hours to obtain 1-(4-(dimethylamino)piperidin-1-yl)-3-(1-ethyl-1H-imidazol-2-yl)propan-1-one hydrochloride (0.283 g, 0.806 mmol, 83%) (hereinafter referred to as the compound of Comparative Example 3) as a white solid.

$^1$H-NMR (400 MHz, D$_2$O) δ: 1.32 (3H, t, J=7.2 Hz), 1.45 (1H, ddd, J=4.4, 12.4, 24.4), 1.58 (1H, ddd, J=4.4, 12.4, 24.4), 1.99-2.07 (2H, m), 2.56-2.63 (1H, m), 2.73 (6H, s), 2.90-2.93 (2H, m), 3.03-3.13 (3H, m), 3.35-3.41 (1H, m), 3.96-3.99 (1H, m), 4.06 (2H, d, J=7.2 Hz), 4.38-4.42 (1H, m), 7.18 (1H, d, J=2.4 Hz), 7.26 (1H, d, J=2.4 Hz).

ESI-MS: as 1-(4-(dimethylamino)piperidin-1-yl)-3-(1-ethyl-1H-imidazol-2-yl)propan-1-one: m/z=279 (M+H)$^+$.

Comparative Example 4—Synthesis of 1-(4-(dimethylamino)piperidin-1-yl)-3-(1-propyl-1H-imidazol-2-yl)propan-1-one hydrochloride

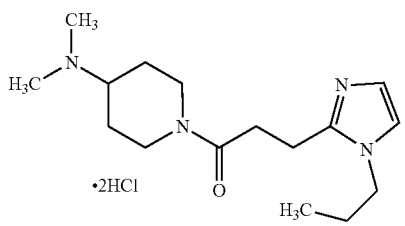 [SMILES: CCCn1ccnc1CCC(=O)N1CCC(N(C)C)CC1]

A solution of hydrogen chloride in dioxane (4.0 M, 0.245 mL, 0.978 mmol) was added to a solution of 1-(4-(dimethylamino)piperidin-1-yl)-3-(1-propyl-1H-imidazol-2-yl)propan-1-one (0.110 g, 0.376 mmol) in diethyl ether (4.00 mL) at 0° C. The reaction liquid was stirred at the same temperature for 1 hour and then stirred at room temperature for 30 minutes. The white solid precipitated was filtered and collected, washed with diethyl ether (7.00 mL) and dried at room temperature for 36 hours to obtain 1-(4-(dimethylamino)piperidin-1-yl)-3-(1-propyl-1H-imidazol-2-yl)propan-1-one hydrochloride (0.105 g, 0.287 mmol, 76%) (hereinafter referred to as the compound of Comparative Example 4) as a white solid.

$^1$H-NMR (400 MHz, D$_2$O) δ: 0.93 (3H, t, J=7.2 Hz), 1.50-1.80 (2H, m), 1.81-1.92 (2H, m), 2.10-2.23 (2H, m), 2.68-2.78 (1H, m), 2.86 (6H, s), 3.02-3.08 (2H, m), 3.15-3.28 (3H, m), 3.45-3.57 (1H, m), 4.08-4.16 (3H, m), 4.50-4.58 (1H, m), 7.32 (1H, brs), 7.38 (1H, brs).

ESI-MS; as 1-(4-(dimethylamino)piperidin-1-yl)-3-(1-propyl-1H-imidazol-2-yl)propan-1-one: m/z=293 (M+H)$^+$.

Comparative Example 5—Synthesis of 1-(4-(dimethylamino)piperidin-1-yl)-3-(1-butyl-1H-imidazol-2-yl)propan-1-one hydrochloride

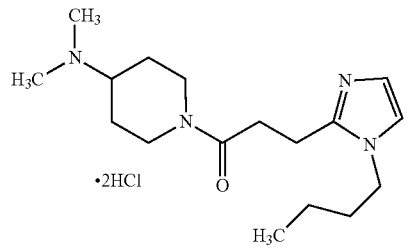 [SMILES: CCCCn1ccnc1CCC(=O)N1CCC(N(C)C)CC1]

A solution of hydrogen chloride in dioxane (4.0 M, 0.255 mL, 1.02 mmol) was added to a solution of 1-(4-(dimethylamino)piperidin-1-yl)-3-(1-butyl-1H-imidazol-2-yl)propan-1-one (0.120 g, 0.392 mmol) in diethyl ether (4.00 mL) at 0° C. The reaction liquid was stirred at the same temperature for 1 hour and then stirred at room temperature for 30 minutes. The white solid precipitated was filtered and collected, washed with diethyl ether (7.00 mL) and dried at room temperature for 36 hours to obtain 1-(4-(dimethylamino)piperidin-1-yl)-3-(1-butyl-1H-imidazol-2-yl)propan-1-one hydrochloride (0.136 g, 0.358 mmol, 91%) (hereinafter referred to as the compound of Comparative Example 5) as a white solid.

$^1$H-NMR (400 MHz, D$_2$O) δ: 0.93 (3H, t, J=6.8 Hz), 1.30-1.40 (2H, m), 1.52-1.86 (4H, m), 2.10-2.22 (2H, m), 2.68-2.78 (1H, m), 2.86 (6H, s), 3.02-3.08 (2H, m), 3.15-3.27 (3H, m), 3.47-3.57 (1H, m), 4.06-4.18 (3H, m), 4.49-4.57 (1H, m), 7.32 (1H, d, J=2.0 Hz), 7.38 (1H, d, J=2.0 Hz).

ESI-MS: as 1-(4-(dimethylamino)piperidin-1-yl)-3-(1-butyl-1H-imidazol-2-yl)propan-1-one: m/z=307 (M+H)$^+$.

Comparative Example 6—Synthesis of 1-(4-(dimethylamino)piperidin-1-yl)-3-(1-isopropyl-1H-imidazol-2-yl)propan-1-one hydrochloride

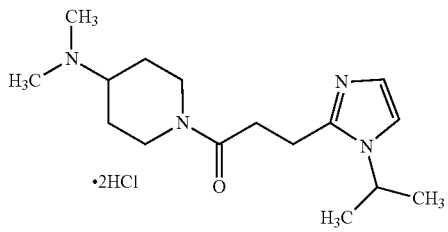 [SMILES: CC(C)n1ccnc1CCC(=O)N1CCC(N(C)C)CC1]

A solution of hydrogen chloride in diethyl ether (2.0 N, 1.06 mL, 2.13 mmol) was added to a solution of 1-(4-(dimethylamino)piperidin-1-yl)-3-(1-isopropyl-1H-imidazol-2-yl)propan-1-one (0.283 g, 0.967 mmol) in diethyl ether (19.3 mL) at 0° C. The reaction liquid was stirred at the same temperature for 1 hour and then stirred at room temperature for 30 minutes. The white solid precipitated was filtered and collected, washed with diethyl ether (58.5 mL) and dried at room temperature for 36 hours to obtain 1-(4-(dimethylamino)piperidin-1-yl)-3-(1-isopropyl-1H-imidazol-2-yl)propan-1-one hydrochloride (0.313 g, 0.806 mmol, 92%) (hereinafter referred to as the compound of Comparative Example 6) as a white solid.

$^1$H-NMR (400 MHz, D$_2$O) δ: 1.36-1.63 (8H, m), 2.00-2.08 (2H, m), 2.58-2.74 (1H, m), 2.74 (6H, s), 2.91-2.94 (2H, m), 3.04-3.16 (3H, m), 3.36-3.44 (1H, m), 3.97-4.01 (1H, m), 4.39-4.42 (1H, m), 4.57-4.65 (1H, m), 7.21 (1H, d, J=2.0 Hz), 7.37 (1H, d, J=2.0 Hz).

ESI-MS: as 1-(4-(dimethylamino)piperidin-1-yl)-3-(1-isopropyl-1H-imidazol-2-yl)propan-1-one: m/z=293 (M+H)$^+$.

Example 14—Effect on Neuropathic Pain in a Mouse Partial Sciatic Nerve Ligation Model Using a partial sciatic nerve ligation model (Seltzer model) in mice by which neuropathic pain can be evaluated, the analgesic action of a cyclic amine derivative (I) or a pharmacologically acceptable salt thereof was investigated. As the cyclic amine derivative (I) or a pharmacologically acceptable salt thereof, the compound of Example 1, 2, 3, 4, 5, 7, 8, 9, 10, 11, 12 or 13 was used for evaluation.

1. Experimental Method

The mouse partial sciatic nerve ligation model was prepared in accordance with the method of Seltzer et al. (Malmberg et al., Pain, vol. 76, p. 215-222, 1998).

Slc: ICR mice (5 weeks old, male; from Japan SLC, Inc.) or Crl: CD1 (ICR) mice (5 weeks old, male; from CHARLES RIVER LABORATORIES JAPAN, INC.) were anesthetized with sodium pentobarbital (70 mg/kg, intraperitoneal administration). The sciatic nerve at the femoral region of the right hind paw of each mouse was exposed and triply ligated tightly with silk suture of 8-0 (from NATSUME SEISAKUSHO CO., LTD.) under a stereomicroscope so that only half thickness of the nerve was trapped in the ligature. A group of mice thus treated was designated as a partial sciatic nerve ligation group. A group of mice whose sciatic nerve was just exposed and not ligated was designated as a sham surgery group.

Evaluation of neuropathic pain (hereinafter referred to as von Frey test) was performed as follows. Mice were conditioned for at least one hour in an acrylic cage for measurement (from NATSUME SEISAKUSHO CO. LTD. or SHINANO SEISAKUSHO) placed on a wire net. Thereafter, using a filament (from North Coast Medical or neuroscience) which exerted a pressure of 0.16 g, the mice were subjected to mechanical tactile stimulus by applying the filament to the plantar surface of the right hind paw 3 times, each for 3 seconds, with an interval of 3 seconds. The withdrawal response observed during each mechanical tactile stimulus was scored (0, no response; 1, showed slow and/or slight withdrawal response in response to the stimulation; 2, showed quick withdrawal response without flinching (shaking paws quickly and continuously) nor licking (licking paws) in response to the stimulation; 3, showed quick withdrawal response with flinching and/or licking), and the sum of the scores obtained in the triplicate trials (hereinafter referred to as the total score) were used as a pain index.

Seven days after the sciatic nerve ligation surgery, the compound of Example 1, 2, 3, 4, 5, 7, 8, 9, 10, 11, 12 or 13 (10 mg/kg for each of the compounds of Example 1, 2, 3, 4, 5, 8, 10 and 13, 0.01 to 1 mg/kg for the compound of Example 7, 0.01 to 10 mg/kg for the compound of Example 9; 0.001 to 0.1 mg/kg for the compound of Example 11; and 0.01 to 1 mg/kg for the compound of Example 12) or pregabalin as a positive control (10 mg/kg; Bosche Scientific) was dissolved in distilled water and orally administered to mice of the partial sciatic nerve ligation group. The groups of the mice in the partial sciatic nerve ligation mouse to which the compound of Example 1, 2, 3, 4, 5, 7, 8, 9, 10, 11, 12 or 13 was administered were designated as a "partial sciatic nerve ligation+the compound of Example 1" group; a "partial sciatic nerve ligation+the compound of Example 2" group; a "partial sciatic nerve ligation+the compound of Example 3" group; a "partial sciatic nerve ligation+the compound of Example 4" group; a "partial sciatic nerve ligation+the compound of Example 5" group; a "partial sciatic nerve ligation+the compound of Example 7" group; a "partial sciatic nerve ligation+the compound of Example 8" group; a "partial sciatic nerve ligation+the compound of Example 9" group; a "partial sciatic nerve ligation+the compound of Example 10" group; a "partial sciatic nerve ligation+the compound of Example 11" group; a "partial sciatic nerve ligation+the compound of Example 12" group; and a "partial sciatic nerve ligation+the compound of Example 13" group, respectively. The partial sciatic nerve ligation mouse group to which pregabalin was administered was designated as a "partial sciatic nerve ligation+pregabalin" group. A group wherein distilled water was orally administered to the mice of the partial sciatic nerve ligation group was designated as a "partial sciatic nerve ligation+ distilled water" group. A group wherein distilled water was orally administered to the mice of the sham surgery group was designated as a "sham surgery+distilled water" group.

The von Frey test was carried out before oral administration of a test compound (pre-value), one hour, two hours, and three hours after the oral administration of a test compound.

2. Results

The results are shown in FIGS. 1 to 12. In the figures, the vertical axis represents the total score (mean value±standard error; n=5 to 6 in FIGS. 1 to 12) in the von Frey test. The higher numerical value indicates stronger pain. The horizontal axis represents time (hr) after administration of a test compound. Efficacy was statistically evaluated by two-sample unpaired Welch's test or Shirley-Williams test using the "partial sciatic nerve ligation+distilled water" group ("partial sciatic nerve ligation+distilled water" in the figures) of every measurement time as a control. In the figures, mark "§ or #" indicates that the value is statistically significant compared to the "partial sciatic nerve ligation+distilled water" group (§: Welch's test ($p<0.05$); or #: Shirley-Williams test ($p<0.025$)).

According to the results of the von Frey test, oral administration of the compound of Example 1, 2, 3, 4, 5, 7, 8, 9, 10, 11, 12 or 13 ("partial sciatic nerve ligation+the compound of Example 1, 2, 3, 4, 5, 7, 8, 9, 10, 11, 12 or 13" showed a statistically significant analgesic action similarly to the positive control, pregabalin ("partial sciatic nerve ligation+pregabalin" in the figures).

From these results, it was clearly demonstrated that a cyclic amine derivative (I) or a pharmacologically acceptable salt thereof has a strong analgesic effect on neuropathic pain.

Comparative Example 7—Effect on Mouse Partial Sciatic Nerve Ligation Model

Using a mouse partial sciatic nerve ligation model (Seltzer model) by which neuropathic pain can be evaluated, analgesic action of Comparative Examples 1, 3, 4, 5 and 6 was investigated.

1. Experimental Method

The mouse partial sciatic nerve ligation model was prepared in accordance with the method of Seltzer et al. (Malmberg et al., Pain, vol. 76, p. 215-222, 1998).

Slc: ICR mice (5 weeks old, male; Japan SLC, Inc.) were anesthetized with sodium pentobarbital (70 mg/kg, intraperitoneal administration). The sciatic nerve at the femoral region of the right hind paw of each mouse was exposed and triply ligated tightly with silk suture of 8-0 (from NATSUME SEISAKUSHO CO., LTD.) under a stereomicroscope so that only half thickness of the nerve was trapped in the ligature. A group of mice thus treated was designated as a partial sciatic nerve ligation group. A group of mice whose sciatic nerve was just exposed and not ligated was designated as a sham surgery group.

Evaluation of neuropathic pain (hereinafter referred to as von Frey test) was performed as follows. Mice were conditioned for at least two hours in an acrylic cage for measurement (from NATSUME SEISAKUSHO CO. LTD. or SHINANO SEISAKUSHO) placed on a wire net. Thereafter, using a filament (from North Coast Medical), which exerts a pressure of 0.16 g, the mice were subjected to mechanical tactile stimulus by applying the filament to the plantar surface of the right hind paw 3 times, each for 3 seconds, with intervals of 3 seconds. The withdrawal response observed during each mechanical tactile stimulus was scored (0: no response; 1: slow and/or slight withdrawal response is shown in response to the stimulation; 2: quick withdrawal response is shown without flinching (shaking paws quickly and continuously) nor licking (licking paws) in response to the stimulation; 3: quick withdrawal response with flinching or licking is shown. The sum of the scores obtained in the three trials (hereinafter referred to as the total score) was used as a pain index.

Seven days after the sciatic nerve ligation surgery, the compound of Comparative Examples 1, 3, 4, 5 or 6 (0.01 to 1 mg/kg for the compound of Comparative Example 1 and 10 mg/kg for each of the compounds of Comparative Example 3 to 6) or pregabalin (10 mg/kg; Bosche Scientific) serving as a positive control was dissolved in distilled water and then orally administered to mice of the partial sciatic nerve ligation group. The partial sciatic nerve ligation mouse groups to which the compounds of Comparative Examples 1, 3, 4, 5 and 6 were separately administered, were designated as a "partial sciatic nerve ligation+the compound of Comparative Example 1" group; a "partial sciatic nerve ligation+the compound of Comparative Example 3" group; a "partial sciatic nerve ligation+the compound of Comparative Example 4" group; a "partial sciatic nerve ligation+the compound of Comparative Example 5" group; and a "partial sciatic nerve ligation+the compound of Comparative Example 6" group, respectively. The group to which pregabalin was administered, was designated as a "partial sciatic nerve ligation group+pregabalin" group. Furthermore, a partial sciatic nerve ligation mouse group to which distilled water was orally administered, was designated as a "partial sciatic nerve ligation group+distilled water" group. The sham surgery mouse group to which distilled water was orally administered, was designated as a "sham surgery+distilled water" group.

The von Frey test was carried out before oral administration of a test compound (pre value), one hour, two hours and three hours after the oral administration.

2. Results

Figure 14:
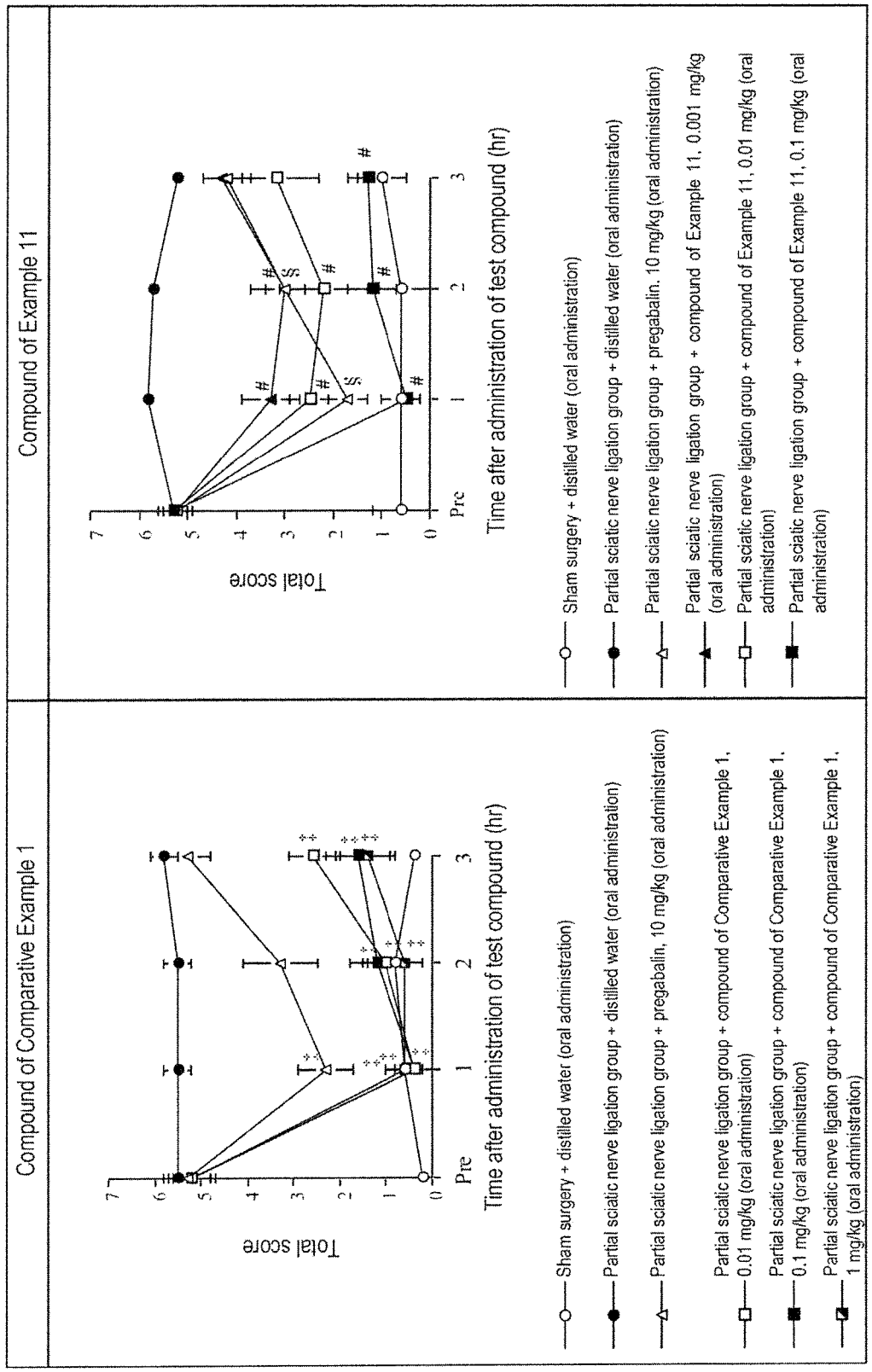
FIG. 14 is a graph showing the effect of the compound of Comparative Example 1 in a mouse partial sciatic nerve ligation model in comparison with the effect of the compound of Example 11 shown in FIG. 10 (oral administration).
Figure 15:
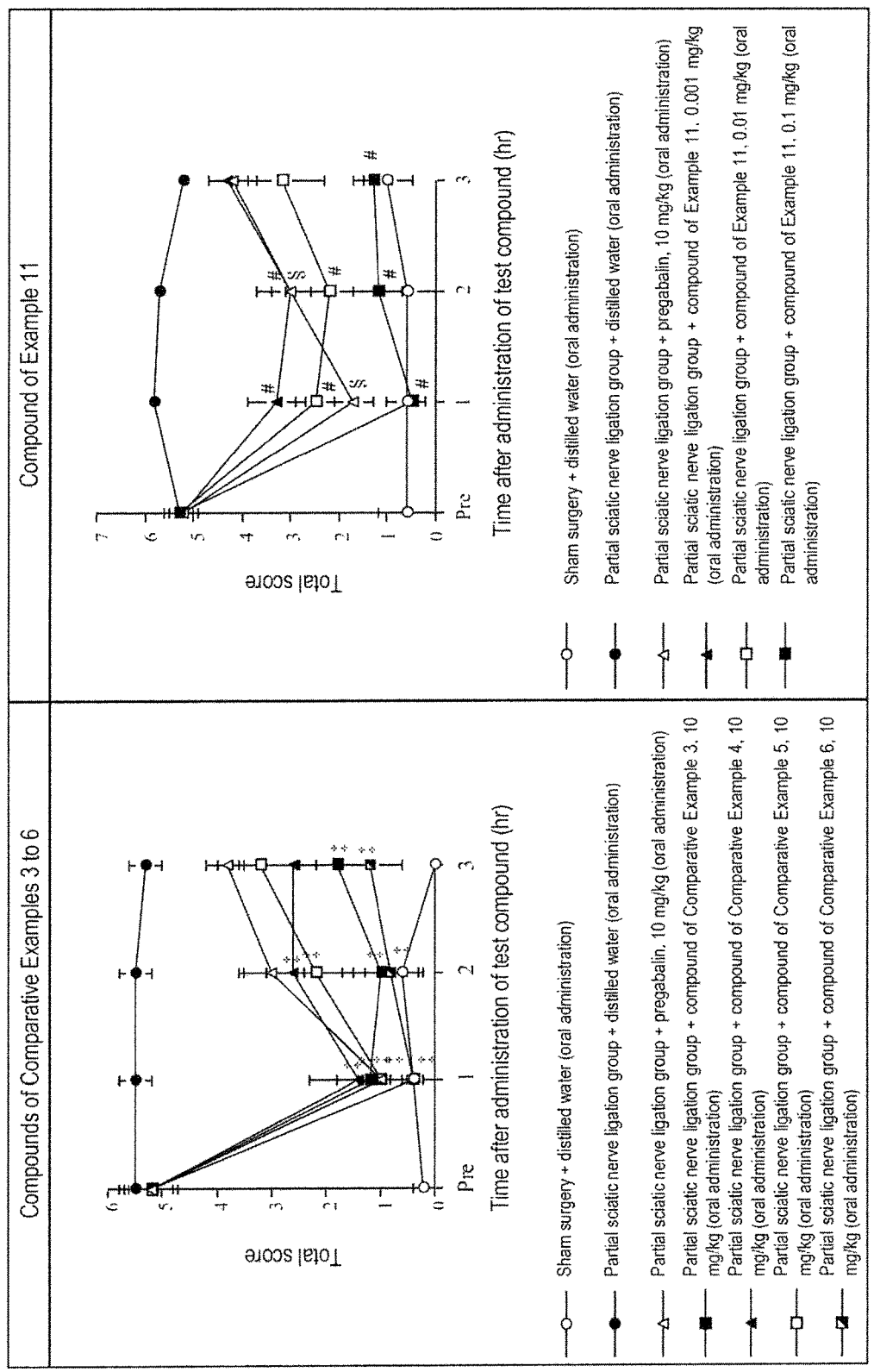
FIG. 15 is a graph showing the effects of the compounds of Comparative Examples 3 to 6 in a mouse partial sciatic nerve ligation model in comparison with the effect of the compound of Example 11 shown in FIG. 10 (oral administration).

The results of the compound of Comparative Example 1 are shown on the left side of FIG. 14; whereas the results of the compound of Comparative Example 3, 4, 5 or 6 are shown on the left side of FIG. 15. As a reference, the effects of the compound of Example 11 shown in FIG. 10 (Example 14) are shown on the right side of each of FIGS. 14 and 15.

In the figure on the left side of each of FIGS. 14 and 15, the vertical axis represents the total score (mean±standard error, n=4 to 5) in the von Frey test. The higher numerical value indicates stronger pain. The horizontal axis represents the passage of time (hr) after administration of a test compound. Efficacy of the compound of Comparative Example 1, 3, 4, 5 or 6 was statistically evaluated by a multi-sample unpaired t-test (corrected by Dunnett) using the "partial sciatic nerve ligation+distilled water" group ("partial sciatic nerve ligation+distilled water" in FIGS. 14 and 15) of every measurement time as a control. In the figure on the left side of each of FIGS. 14 and 15, mark "‡" indicates that the value is statistically significant compared to the "partial sciatic nerve ligation+distilled water" group (‡: $p<0.05$).

According to the results of the von Frey test, oral administration of the compound of Comparative Example 1, 3, 4, 5 or 6 ("partial sciatic nerve ligation+the compound of Comparative Example 1, 3, 4, 5 or 6" in FIGS. 14 and 15) showed a statistically significant analgesic action similarly to the positive control, pregabalin ("partial sciatic nerve ligation+pregabalin" in the figures).

However, the compound of Comparative Example 1 started showing a statistically significant analgesic action at a dose of 0.01 mg/kg. However, the strongest analgesic action was shown one hour after oral administration. The analgesic action tended to decrease 2 hours and 3 hours later. Similarly, the compound of Comparative Example 3, 4, 5 or 6 showed the strongest analgesic action one hour after the oral administration and the analgesic action tended to decrease 2 hours and 3 hours later. In contrast, the compound of Example 11 started showing a statistically significant analgesic action from a dose of as low as 0.001 mg/kg and the analgesic action lasted up to 2 hours after the oral administration. Furthermore, the analgesic action of the compound of Example 11 at a dose of 0.1 mg/kg lasted 3 hours after the oral administration. The persistence of analgesic action was confirmed with respect to the compound of Example 7 (shown in FIG. 6), the compound of Example 9 (shown in FIG. 8) and the compound of Example 12 (shown in FIG. 11). Accordingly, it was demonstrated that the cyclic amine derivative (I) or a pharmacologically acceptable salt thereof has more persistent analgesic action against neuropathic pain, compared to imidazole derivatives described in International Publication WO No. 2013/147160.

Example 15—Effect on Fibromyalgia Syndrome Model in Rats

Using a fibromyalgia syndrome model in rats by which fibromyalgia syndrome can be evaluated, the analgesic action of a cyclic amine derivative (I) or a pharmacologically acceptable salt thereof was investigated.

As the cyclic amine derivative (I) or a pharmacologically acceptable salt thereof, the compound of Example 11 was used for evaluation.

1. Experimental Method

To prepare a fibromyalgia syndrome model rat (Sluka et al., Journal of Pharmacology and Experimental Therapeutics, vol. 302, p. 1146-1150, 2002; Nagakura et al., Pain, vol. 146, p. 26-33, 2009; Sluka et al., Pain, vol. 146, p. 3-4, 2009), which is generally employed widely in basic research for fibromyalgia syndrome, acidic saline (100 μL) adjusted to pH 4.0 was intramuscularly injected to the gastrocnemius muscle of the right hind paw of Crl: CD(SD) rat (6 to 7 weeks old, male; from CHARLES RIVER LABORATORIES JAPAN, INC.) under continuous inhalation anesthesia with isoflurane, twice (once in each day of Day 1 and Day 6, wherein Day 1 was the date on which the acidic saline was initially administrated). The rats thus prepared were raised in a breeding room controlled at an indoor temperature of 21 to 25° C. and an indoor humidity of 40 to 70% under the conditions of voluntary intake of food and water. In the same manner, rats to which physiological saline in place of acidic saline was intramuscularly injected were raised. The rats thus raised and not afflicted with fibromyalgia syndrome ("physiological saline+distilled water" group in FIG. 13) were also used in the experiment.

Seven days after the initial administration of acidic saline, allodynia in each rat was measured. The rats which exhibited a 50% response threshold (mean value of the right hind paw and the left hind paw) of 2 g or more to 6 g or less were selected as fibromyalgia syndrome model rats with the onset of fibromyalgia syndrome and subjected to the following administration experiment. Note that, measurement of allodynia was performed by use of a von Frey filament (from North Coast Medical) in accordance with the method described in a known literature (Chaplan et al., Journal of Neuroscience Methods, vol. 53, p. 55-63, 1994).

The fibromyalgia syndrome model rats thus obtained are divided into groups such that the 50% response threshold (mean value of the right hind paw and the left hind paw) of the individual groups became equal, and a test compound was administered to the fibromyalgia syndrome model rats on Day 7 after the initial administration of acidic saline.

Figure 13:
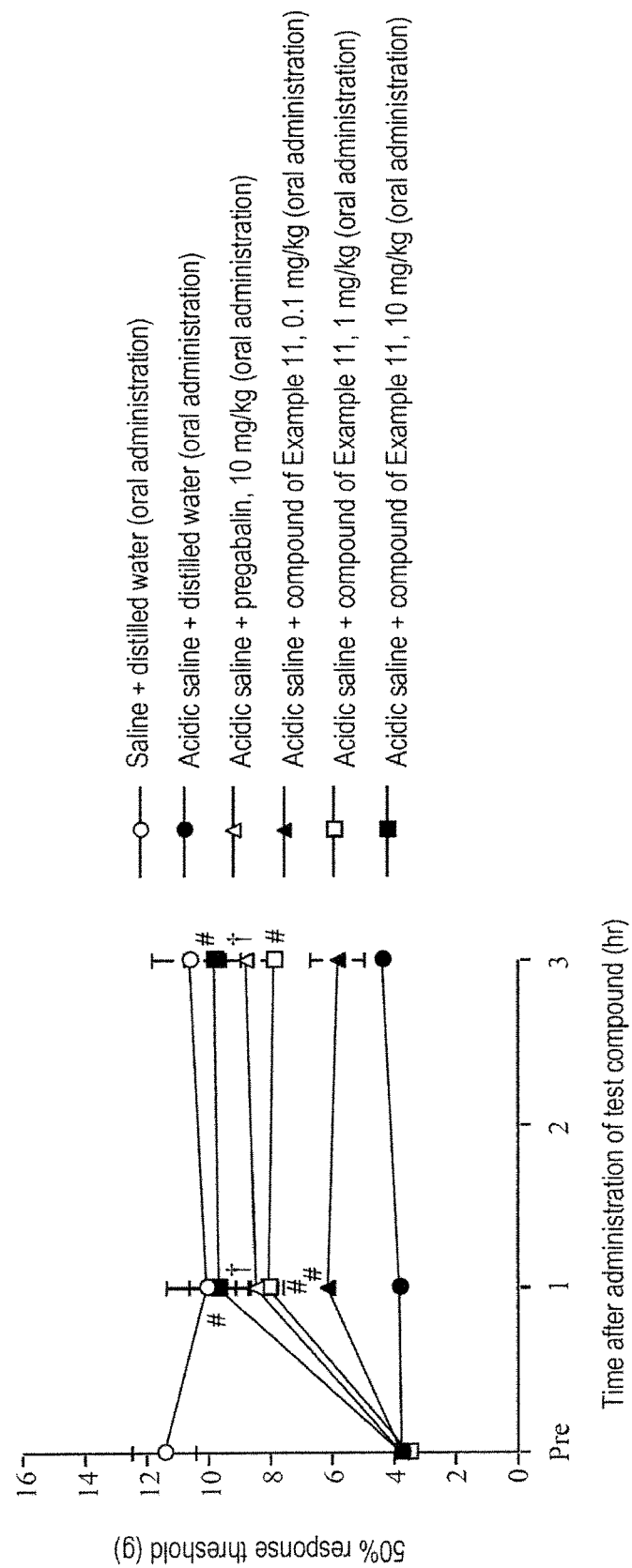
FIG. 13 is a graph showing the effect of the compound of Example 11 in a rat fibromyalgia model (oral administration).

The compound of Example 11 (0.1 to 10 mg/kg) was dissolved in distilled water and then orally administered to fibromyalgia syndrome model rats ("acidic saline+the compound of Example 11" in FIG. 13). Pregabalin serving as a positive control (10 mg/kg; from KEMPROTEC) was dissolved in distilled water and then orally administered ("acidic saline+pregabalin" in FIG. 13). As a control, distilled water was orally administered to fibromyalgia syndrome model rats ("acidic saline+distilled water" in FIG. 13). Furthermore, distilled water was orally administered to rats not afflicted with fibromyalgia syndrome ("physiological saline+distilled water" in FIG. 13). One hour and three hours after the oral administration, allodynia in individual rats was measured to evaluate an analgesic action. At this time, the 50% response threshold value in the measurement of allodynia before oral administration of the test compound on Day 7 after initial administration of acidic saline was defined as the pre-value.

2. Results

The results are shown in FIG. 13. In that figure, the vertical axis represents 50% response threshold (mean value of the right hind paw and the left hind paw) (g) (mean value±standard error, n=5 to 6). The higher numerical value indicates that allodynia is improved in the fibromyalgia syndrome model rats.

FIG. 13 shows the results of oral administration of the compound of Example 11. In the figure, the horizontal axis represents the time before oral administration of the compound of Example 11 (pre-value) and the time (hr) from the oral administration. In the figure, mark t or #, indicates that the value is statistically significant compared to the "acidic saline+distilled water" group ("acidic saline+distilled water" in the figure) of every measurement time as the results of the unpaired t test or Williams test (t: t-test ($p<0.05$) or #: Williams test ($p<0.025$)).

In the group to which the compound of Example 11 was orally administered ("acidic saline+the compound of Example 11" in FIG. 13), the allodynia observed in the fibromyalgia syndrome model rats was statistically significantly improved compared to the "acidic saline+distilled water" group, similarly to a positive control, i.e., the group to which pregabalin was orally administered ("acidic saline+pregabalin" in FIG. 13).

From these results, it was clearly demonstrated that a cyclic amine derivative (I) or a pharmacologically acceptable salt thereof is effective to fibromyalgia syndrome.

Comparative Example 8—Effect on Fibromyalgia Syndrome Model in Rats

Using a fibromyalgia syndrome model in rats by which fibromyalgia syndrome can be evaluated, the analgesic action of the compound of Comparative Example 1 was investigated.

1. Experimental Method

To prepare a fibromyalgia syndrome model rat (Sluka et al., Journal of Pharmacology and Experimental Therapeutics, vol. 302, p. 1146-50, 2002; Nagakura et al., Pain, vol. 146, p. 26-33, 2009; Sluka et al., Pain, vol. 146, p. 3-4, 2009), which is generally employed widely in basic research for fibromyalgia syndrome, acidic saline (100 μL) adjusted to pH 4.0 was intramuscularly injected to the gastrocnemius muscle of the right hind paw of Slc: (SD) rats (6 to 7 weeks old, male; from Japan SLC, Inc.) under continuous inhalation anesthesia with isoflurane, twice (once in each of Day 1 and Day 6, wherein Day 1 was the initial administration date of the acidic saline). The rats thus prepared were raised in a breeding room controlled at an indoor temperature of 21 to 25° C. and an indoor humidity of 40 to 70% under the conditions of voluntary intake of food and water. In the same manner, rats to which physiological saline was intramuscularly injected in place of acidic saline were raised. The rats thus raised and not afflicted with fibromyalgia syndrome ("physiological saline+distilled water" group in the figure on the left side of FIG. 16) were used in the experiment.

Seven days after the initial administration of acidic saline, allodynia in each rat was measured. The rats, which exhibited a 50% response threshold (mean value of the right hind paw and the left hind paw) of 6 g or less, were selected as fibromyalgia syndrome model rats with the onset of fibromyalgia syndrome and subjected to the following administration experiment. Measurement of allodynia was performed by use of a von Frey filament in accordance with the method described in a known literature (Chaplan et al., Journal of Neuroscience Methods, vol. 53, p. 55-63, 1994).

The fibromyalgia syndrome model rats thus obtained were divided into groups such that the 50% response threshold of the individual groups became equal, and the compound of Comparative Example 1 (0.1 to 1 mg/kg) or a positive control, pregabalin (10 mg/kg; from Bosche Scientific), which was dissolved in distilled water, was orally administered to the fibromyalgia syndrome model rats on Day 7 after the initial administration of acidic saline. Furthermore, distilled water was orally administered to control fibromyalgia syndrome model rats ("acidic saline+distilled water" group in FIG. 16, left). Distilled water was orally administered to rats not afflicted with fibromyalgia syndrome ("physiological saline+distilled water" group). One hour, two hours and three hours after the oral administration, allodynia was measured in individual rats to evaluate an analgesic action of the test compound. At this time, the 50% response threshold value in the measurement of allodynia before oral administration of the test compound on Day 7 after initial administration of acidic saline was defined as the pre-value.

2. Results

Figure 16:
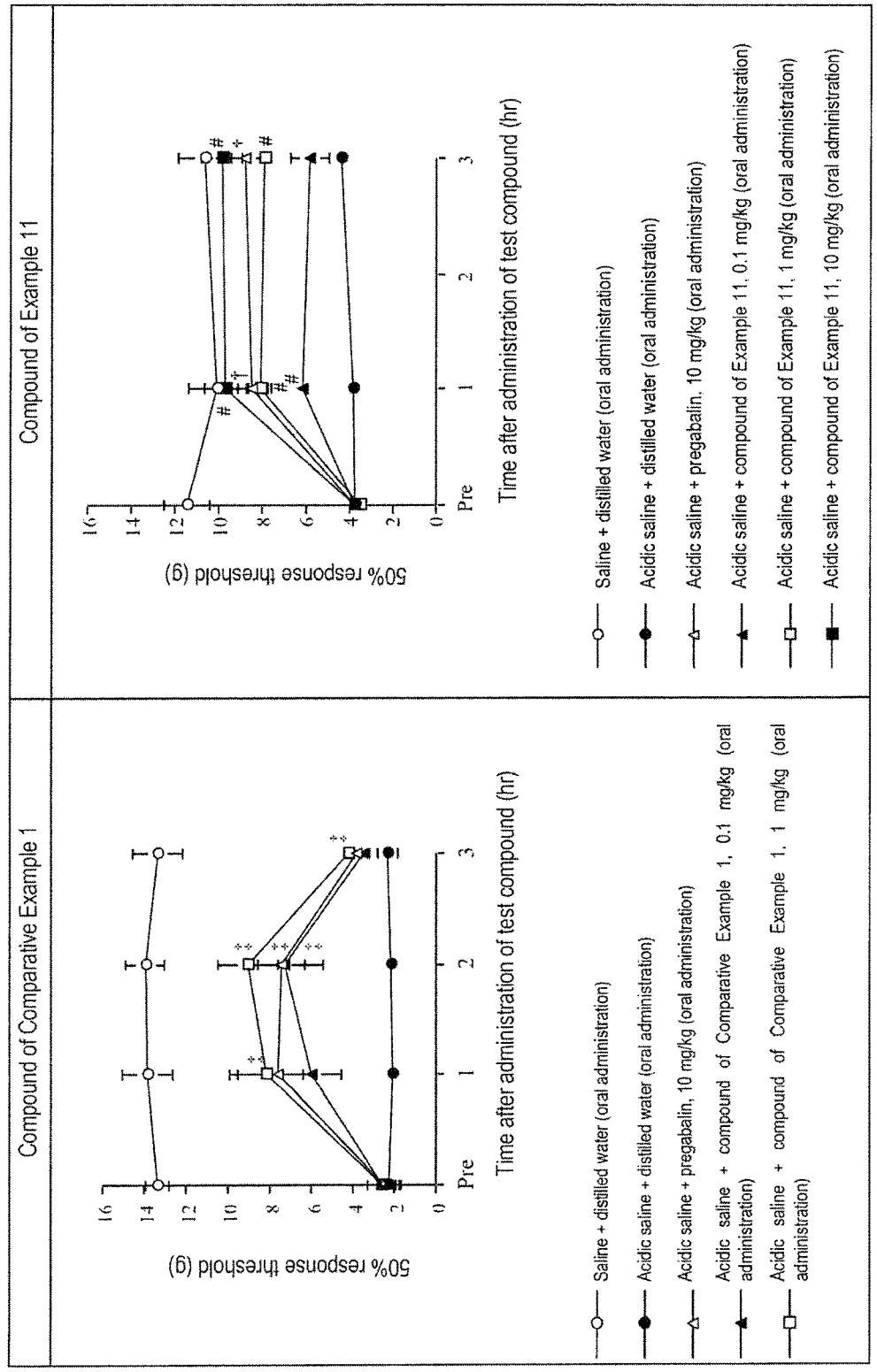
FIG. 16 is a graph showing the effect of the compound of Comparative Example 1 in a rat fibromyalgia models in comparison with the effect of the compound of Example 11 shown in FIG. 13 (oral administration).

The results of the compound of Comparative Example 1 are shown in FIG. 16, left. Also, the effect of the compound of Example 11 shown in FIG. 13 (Example 15) is shown in FIG. 16, right, for comparison.

In FIG. 16, left, the vertical axis represents 50% response threshold (g) (mean value±standard error, n=4 to 6). The higher numerical value indicates that allodynia is improved in the fibromyalgia syndrome model rats. The horizontal axis represents the value before the oral administration of test compounds (pre value) or the passage of time (hr) from the oral administration. In FIG. 16, left, mark "‡" indicates that the value is statistically significant (‡: $p<0.05$) as the result of a multi-group unpaired t-test (corrected by Dunnett) using the "acidic saline+distilled water" group ("acidic saline+distilled water" in FIG. 16, left) of every measuring time as a control.

In the group to which the compound of Comparative Example 1 was orally administered ("acidic saline+the compound of Comparative Example 1" in FIG. 16, left), the allodynia observed in the fibromyalgia syndrome model rats was statistically significantly improved compared to the "acidic saline+distilled water" group, similarly to a positive control, i.e., the group to which pregabalin was orally administered ("acidic saline+pregabalin" in FIG. 16, left).

Although the compound of Comparative Example 1 exerted a statistically significant analgesic action; the analgesic action tended to significantly decrease 3 hours after oral administration. In contrast, the compound of Example 11 exerted a statistically significant analgesic action and the analgesic action lasted up to 3 hours after the oral administration. Accordingly, it was demonstrated that the cyclic amine derivative (I) or a pharmacologically acceptable salt thereof exerts a long-lasting analgesic action against fibromyalgia syndrome, compared to an imidazole derivative described in International Publication WO No. 2013/147160.

Example 16—Stability Test in Liver Microsomes of Human, Monkey, Dog and Mouse

Using the stability test in liver microsomes, which is known as in-vitro evaluation test for checking stability of a compound against hepatic metabolism, stability of the cyclic amine derivative (I) or a pharmacologically acceptable salt thereof against hepatic metabolisms in human, monkey, dog and mouse was evaluated.

1. Experimental Method

Experiment was performed using the compound of Example 11, Comparative Example 1 or Comparative Example 6 as a test compound and human liver microsomes (from Xenotech), monkey liver microsomes (from Xenotech), dog liver microsomes (from Xenotech) or mouse liver microsomes (from Xenotech) as the liver microsomes.

The reagents to be used in the stability test in liver microsomes were prepared as follows. A D-glucose 6-phosphate disodium salt (hereinafter referred to as G6P) was dissolved with distilled water to prepare an aqueous solution of G6P (100 mmol/L). Glucose 6-phosphate dehydrogenase (1000 units) from Yeast (hereinafter referred to as G6PDH) was dissolved with distilled water (5 mL) to prepare an aqueous solution of G6PDH (200 units/mL). $MgCl_2$ was dissolved with distilled water to prepare an aqueous solution of $MgCl_2$ (100 mmol/L). To a 200 mmol/L aqueous solution of $K_2HPO_4$ (500 mL), a 200 mmol/L aqueous solution of $KH_2PO_4$ (about 130 mL) was added and the pH of the resulting solution was adjusted to be 7.4 to prepare a 200 mmol/L $KH_2PO_4/K_2HPO_4$ buffer, pH 7.4 (hereinafter referred to as 200 mmol/L PB). β-Nicotinamide-adenine dinucleotide phosphate, reduced form, tetrasodium salt (hereinafter referred to as NADPH) was dissolved with distilled water to prepare a 10 mmol/L aqueous solution of NADPH.

The stability test in liver microsomes was carried out in the following procedure. First, the reagents (except NADPH) listed in Table 2 were mixed to prepare a reaction mixture. The reaction mixture was dispensed to four wells (a well for a 0-minute reaction, a well for a 30-minute reaction, a well for a 20-minute reaction, a well for a 10-minute reaction) of a 96-well tube plate (BM apparatus; hereinafter referred to as the plate) in an amount of 135 µL per well. The whole plate was covered with a silicone cap and soaked in a water bath of 37° C. for 10 minutes to carry out pre-incubation.

After the pre-incubation, a 10 mmol/L aqueous solution of NADPH (15.0 µL) was added to the well for a 30-minute reaction. The plate was covered with a cap and soaked in a water bath of 37° C. and a reaction was initiated. Ten minutes after the initiation of the reaction, a 10 mmol/L aqueous solution of NADPH (15.0 µL) was added to the well for a 20-minute reaction. Twenty minutes after the initiation of the reaction, a 10 mmol/L aqueous solution of NADPH (15.0 µL) was added to the well for a 10-minute reaction. The plate was further soaked in a water bath of 37° C. to continue the reaction.

Thirty minutes after the initiation of the reaction, the plate was taken out from the water bath and acetonitrile (120 µL) was added to each of the wells. The plate was covered, vortexed by Direct Mixer for 10 seconds and thereafter cooled on ice for 10 minutes to terminate the reaction. After termination of the reaction, a 10 mmol/L aqueous solution of NADPH (15.0 µL) was added to the well for a 0-minute reaction.

TABLE 2

| Reagent (concentration) | Added volume (µL) | Final concentration |
|---|---|---|
| G6P (100 mmol/L) | 15.0 | 10 mmol/L |
| G6PDH (200 units/mL) | 0.75 | 1 units/mL |
| MgCl$_2$ (100 mmol/L) | 12.0 | 8 mmol/L |
| Liver microsomes of human, monkey, dog or mouse (20 mg/mL) | 3.75 | 0.5 mg/mL |
| PB (200 mmol/L) | 75.0 | 100 mmol/L |
| Test compound (0.1 mmol/L) | 3.0 | 2 µmol/L |
| Distilled water | 25.5 | — |
| NADPH (10 mmol/L) | 15.0 | 1 mmol/L |
| Total volume | 150.0 | — |

With respect to the compound of Example 11, the reaction mixtures in individual wells were centrifuged at 4° C. and 2500 rpm for 10 minutes and the supernatants were subjected to LC/MS/MS analysis. The LC/MS/MS analysis conditions are as follows.

Conditions for Human and Mouse Liver Microsomes Analysis

| | |
|---|---|
| [HPLC system] | LC-20A/30A (Shimadzu Corporation) |
| [Column] | Ascentis Express F5, 2.7 µm |
| | 5 cm × 2.1 mm (SUPELCO) |
| [Mobile phase] | Solution A: 0.1 vol % formic acid in water |
| | Solution B: 0.1 vol % formic acid in acetonitrile |
| [Flow rate] | 0.7 mL/min |
| [Gradient program] | Solution B: 70 → 30 vol % |

Conditions for Monkey and Dog Liver Microsomes Analysis

| | |
|---|---|
| [HPLC system] | Agiletnt 1200 (Agiletnt) |
| [Column] | CHIRALCEL OZ-3R, 3 µm |
| | 4.6 mm × 150 mm ID (DAICEL Corporation) |
| [Mobile phase] | Methanol:2-propanol:ethylenediamine = 500:500:0.1 |
| [Flow rate] | 0.5 mL/min |

With respect to the compound of Comparative Example 1, the reaction mixtures in individual wells were centrifuged at 4° C. and 2500 rpm for 10 minutes and the supernatants were subjected to LC/MS analysis. The LC/MS analysis conditions are as follows.

Conditions for Human Liver Microsomes

| | |
|---|---|
| [HPLC system] | Waters HPLC (Waters) |
| [Column] | BEH C18, 1.7 µm |
| | 2.1 mm ID × 50 mm (Waters) |
| [Mobile phase] | Solution A: 10 mM ammonium bicarbonate water (pH 10) |
| | Solution B: acetonitrile |
| [Flow rate] | 0.3 mL/min |
| [Gradient program] | Solution B: 1 → 50 vol % |

Conditions for Monkey and Dog Liver Microsomes

| | |
|---|---|
| [HPLC system] | Waters HPLC (Waters) |
| [Column] | PC HILIC, 3 µm |
| | 2.0 mm ID × 50 mm (Shiseido Co., Ltd.) |
| [Mobile phase] | Solution A: 0.1 vol % formic acid in water |
| | Solution B: acetonitrile |
| [Flow rate] | 0.55 mL/min |
| [Gradient program] | Solution B: 5 → 60 vol % |

Conditions for Mouse Liver Microsomes

| | |
|---|---|
| [HPLC system] | Waters HPLC (Waters) |
| [Column] | XBridge C18, 2.5 µm |
| | 2.1 mm ID × 50 mm (Waters) |
| [Mobile phase] | Solution A: 10 mM ammonium bicarbonate (pH 10) |
| | Solution B: acetonitrile |
| [Flow rate] | 0.3 mL/min |
| [Gradient program] | Solution B: 1 → 20 vol % |

With respect to the compound of Comparative Example 6, the reaction mixtures in individual wells were centrifuged at 4° C. and 2500 rpm for 10 minutes and the supernatants were subjected to LC/MS/MS analysis. The LC/MS/MS analysis conditions are as follows.

Conditions for Human Liver Microsomes

| | |
|---|---|
| [HPLC system] | Agiletnt 1200 (Agiletnt) |
| [Column] | Unison UK-Silica |
| | 50 mm × 3 mm (Unison) |
| [Mobile phase] | Solution A: 0.05 mM ammonium acetate (pH 4) |
| | Solution B: acetonitrile |
| [Flow rate] | 0.5 mL/min |
| [Gradient program] | Solution B: 50 vol % |

Conditions for Monkey and Dog Liver Microsomes

| | |
|---|---|
| [HPLC system] | Agiletnt 1200 (Agiletnt) |
| [Column] | CAPCELL PAK C18 MGIII, 5 µm |
| | 2.0 mm ID × 50 mm (Shiseido Co., Ltd.) |
| [Mobile phase] | Solution A: 10 mM ammonium formate (pH 3) |
| | Solution B: acetonitrile |
| [Flow rate] | 0.4 mL/min |
| [Gradient program] | Solution B: 1 → 90 vol % |

With respect to the chromatogram of each well obtained by LC/MS analysis or LC/MS/MS analysis, the test compound residual ratio (%) at each reaction time t (min) was calculated based on the peak area at the reaction time of 0 minute as 100%. The test compound residual ratio was plotted on a single logarithmic graph relative to the reaction time and fitted to the following Expression (1) in accordance with the least squares method to computationally obtain the elimination rate constant k (min$^{-1}$). The obtained value k was divided by the microsomal protein concentration (value)

based on the following Expression (2) to computationally obtain hepatic intrinsic clearance, $CL_{int}$ (mL/min/mg).

$$\text{Test compound residual ratio} = A \times \exp(-kt) \quad (1)$$

$$CL_{int} = k/\text{microsomal protein concentration} \quad (2)$$

2. Results

The hepatic intrinsic clearance values obtained from the stability tests in liver microsomes are shown in Table 3. Note that, a larger hepatic intrinsic clearance value indicates that the metabolism of the test compound in the liver microsomes is fast. Abbreviation, "N.E." in the table indicates that a test was not carried out.

TABLE 3

| Test compound | Hepatic intrinsic clearance (mL/min/mg) | | | |
|---|---|---|---|---|
| | Human | Monkey | Dog | Mouse |
| Compound of Example 11 | 0.000 | 0.000 | 0.000 | 0.003 |
| Compound of Comparative Example 1 | 0.001 | 0.002 | 0.000 | 0.004 |
| Compound of Comparative Example 6 | 0.000 | 0.006 | 0.006 | N.E. |

As shown in Table 3, the hepatic intrinsic clearance values of the test compound of Example 11 in the stability test in liver microsomes were commonly low in all animal species tested in this Example, compared to the value of the test compound of Comparative Example 1 or Comparative Example 6. Accordingly, it was demonstrated that the compound of Example 11 is rarely metabolized in the livers of human, monkey, dog and mouse, in other words, is stably present in vivo.

From the results, it was demonstrated that the cyclic amine derivative (I) or a pharmacologically acceptable salt thereof is more stably present in vivo than imidazole derivatives described in International Publication WO No. 2013/147160.

Example 17—Pharmacokinetics (PK) Test

As a test compound, the compound of Example 11 or Comparative Example 2 was intravenously or orally administered to monkeys and the plasma concentration after the administration was investigated.

1. Experimental Method

Cynomolgus monkeys (4 to 6 years old, male) were raised under the conditions of voluntary intake of solid food (Oriental Yeast Co., Ltd) and tap water and fasted from the evening of the day before initiation of administration and subjected to an experiment. Note that blood was sampled at 4 hours after administration (on and after 16:00), and thereafter feeding was restarted.

The compound of Example 11 or Comparative Example 2 was single administered intravenously (1 mg/kg) or orally (1 mg/kg) to cynomolgus monkeys. Dosing solution for intravenous administration of the compound of Example 11 or Comparative Example 2 was prepared by dissolving the compound in physiological saline specified by the Japanese Pharmacopoeia to obtain a concentration of 10 mg/mL. Dosing solution for oral administration of the compound of Example 11 or Comparative Example 2 was prepared by dissolving the compound in the injection water specified by the Japanese pharmacopoeia to obtain a concentration of 1 mg/mL. Dosing solution for intravenous administration was injected through the saphenous vein by use of a syringe needle (attached to a syringe barrel). The oral administration into the stomach was compulsively carried out by inserting a catheter into the nasal cavity.

When the dosing solution for administration of the compound of Example 11 or Comparative Example 2 was intravenously administrated, blood was collected from the forearm cephalic vein under no anesthesia at each of the time points (9 points in total): e.g., before intravenous administration, 5, 15, 30 minutes and 1, 2, 4, 8, 24 hours after the administration.

When the dosing solution for oral administration of the compound of Example 11 was orally administrated, blood was collected from the forearm cephalic vein under no anesthesia at each of the time points (9 points in total): e.g., before oral administration, 15, 30, 45 minutes and 1, 2, 4, 8, 24 hours after the administration. When the dosing solution for oral administration of the compound of Comparative Example 2 was orally administrated, blood was sampled from the forearm cephalic vein under no anesthesia at each of the time points (9 points in total): e.g., before oral administration, 30 minutes and 1, 2, 3, 4, 6, 8, 24 hours after the administration.

The blood sampled was centrifuged at 4° C. and 1800×g for 15 minutes to obtain the plasma. The plasma thus obtained was stored at about −80° C. until use in preparation of analysis samples. The plasma obtained from a cynomolgus monkey to which a test compound was administered, is referred to as a plasma sample; whereas the plasma obtained from a cynomolgus monkey to which a test compound was not administered, is referred to as the blank plasma.

To the plasma sample (50 μL) obtained from a cynomolgus monkey to which the compound of Example 11 was administered or the plasma sample (50 μL) appropriately diluted with the blank plasma, an internal standard solution and 200 μL of methanol were added. The resulting solution was vortexed and cooled at 4° C. for 10 minutes. A sample for a calibration curve was prepared by adding a standard solution for a calibration curve to the blank plasma and subjecting the resulting mixture to the same treatment. After cooling, each of the samples was spun at 4° C. and 2000 rpm for 10 minutes by a centrifuge (Hitachi Koki Co., Ltd.). The resulting supernatant was used as a sample for LC/MS/MS analysis. The LC/MS/MS analysis conditions were the same as those employed for the stability test in liver microsomes of monkey and dog (Conditions for monkey and dog liver microsomes) of the compound of Example 11, described in Example 16.

To the plasma sample (50 μL) obtained from a cynomolgus monkey to which the compound of Comparative Example 2 was administered or a plasma sample (50 μL) appropriately diluted with the blank plasma, an internal standard solution and 150 μL of methanol were added. The resulting solution was vortexed and cooled at 4° C. for 10 minutes. A sample for a calibration curve was prepared by adding a standard solution for a calibration curve to the blank plasma and subjecting the resulting mixture to the same treatment. After cooling, each of the samples was spun at 4° C. and 2000 rpm for 10 minutes by a centrifuge (Hitachi Koki Co., Ltd.). The resulting supernatant was diluted 10 fold with 70 vol % acetonitrile containing 0.1 vol % formic acid and subjected as a sample for LC/MS/MS analysis. The LC/MS/MS analysis conditions were as follows:

| | |
|---|---|
| [HPLC system] | Agiletnt 1200 (Agiletnt) |
| [Column] | Ascentis Express F5, 2.7 µm |
| | 5 cm × 2.1 mm (SUPELCO) |
| [Mobile phase] | Solution A: 0.1 vol % formic acid in water |
| | Solution B: 0.1 vol % forminc acid in acetonitrile |
| [Flow rate] | 0.7 mL/min |
| [Gradient program] | Solution B: 70 → 30 vol %. |

Based on the results of the LC/MS/MS analysis, a calibration curve was prepared by using Analysis 1.6.2 (Applied Biosystems) and the concentrations of test compounds in the analysis samples were calculated. The test-compound concentrations in the plasma at each sampling time point in the case of intravenous administration or oral administration were calculated and PK analysis was carried out for individual monkeys. PK parameters were calculated by using WinNonlin (Pharsight), in accordance with an analysis independent of a model (intravenous administration: Bolus IV Administration, oral administration: Extravascular Administration; Weight=1/y in both administrations). Furthermore, bioavailability (BA) was calculated based on the following Expression (3) by dividing $AUC_{0-\infty iv}$ (time 0 to $\infty$) at the time of the intravenous administration and $AUC_{0-\infty po}$ (time 0 to $\infty$) at the time of the oral administration by respective dose values to obtained as normalized values.

$$\text{Bioavailability } (BA) = (AUC_{0-\infty, po}/\text{dose})/(AUC_{0-\infty, iv}/\text{dose}) \quad (3)$$

2. Results

Figure 17:
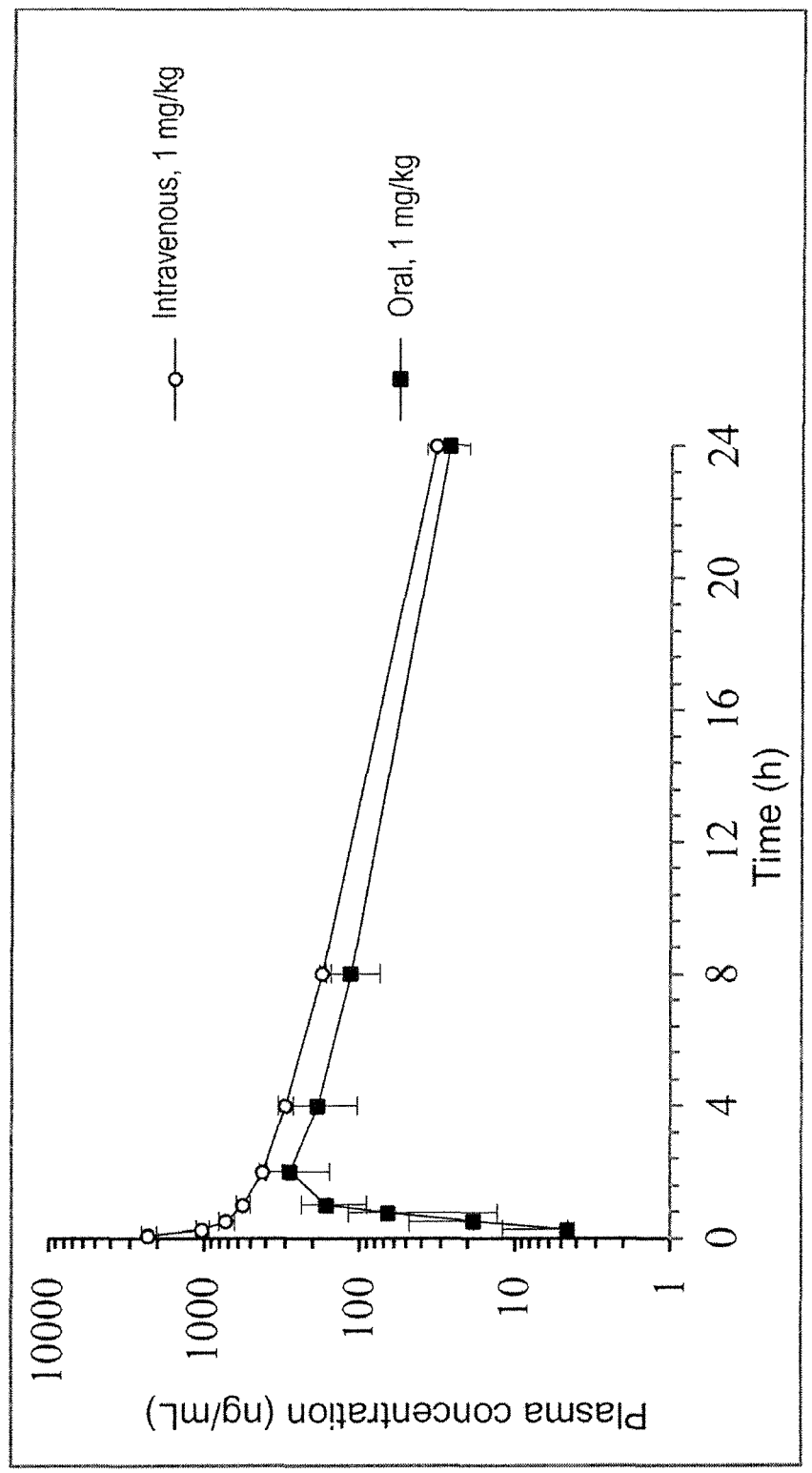
FIG. 17 is a graph showing the plasma concentration-time curves of the compound of Example 11 in cynomolgus monkeys (intravenous administration and oral administration).
Figure 18:
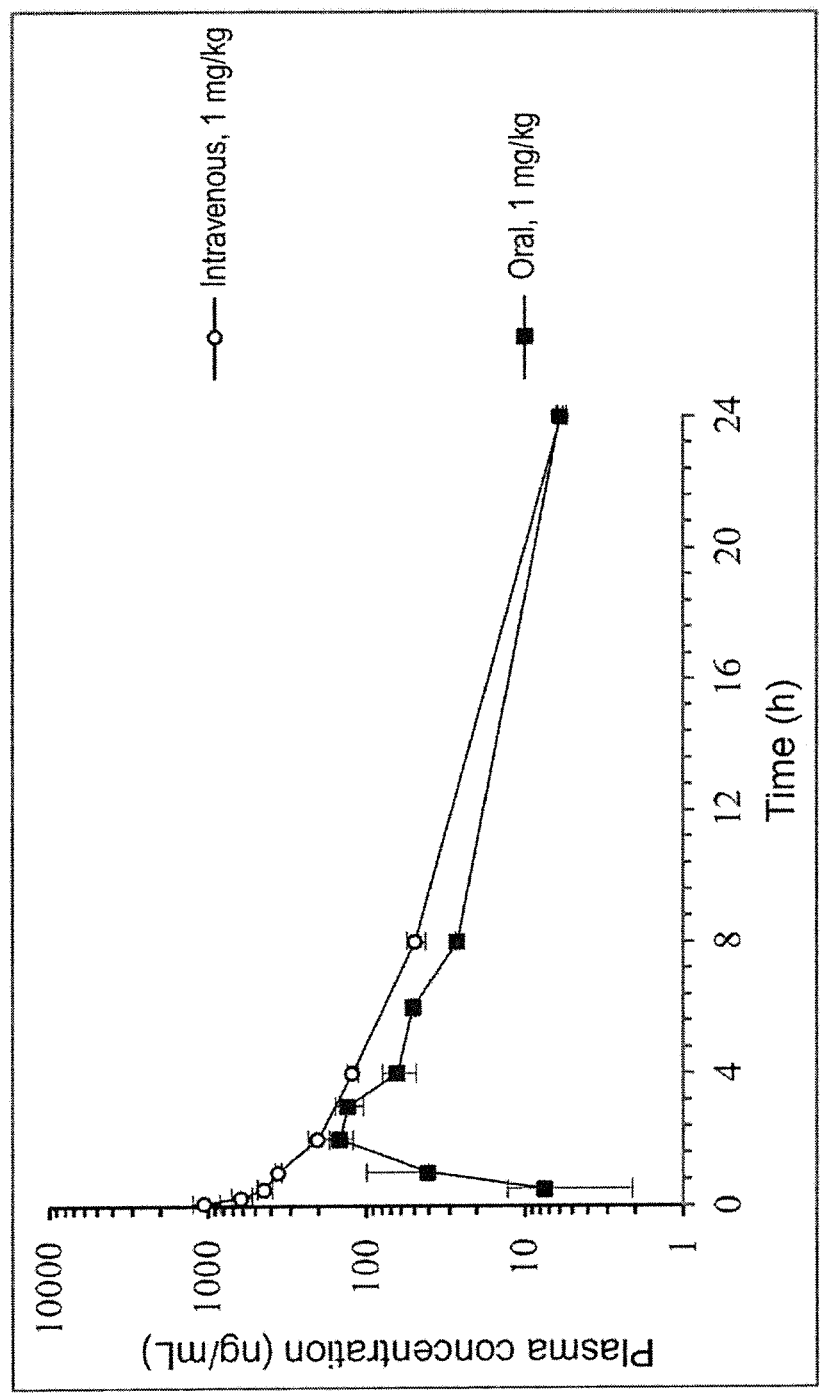
FIG. 18 is a graph showing the plasma concentration-time curves of the compound of Comparative Example 2 in cynomolgus monkeys (intravenous administration and oral administration).

The plasma concentration-time curves of the compound of Example 11 are shown in FIG. 17 and the plasma concentration-time curves of the compound of Comparative Example 2 are shown in FIG. 18. Each plot and bar represents the mean plasma concentration±standard deviation at each time point. The PK parameters are shown in Table 4. $C_{max}$ (ng/mL) represents a maximum plasma concentration in the case of oral administration; $AUC_{0-\infty, po}$ (ng·h/mL) represents the area under the curve of plasma concentration in the case of oral administration; $t_{1/2}$ (h) represents the elimination half-life in the plasma in the case of oral administration; $CL_{tot}$ (mL/h/kg) represents total body clearance in the case of intravenous administration; and BA (%) represents bioavailability.

TABLE 4

| PK parameters | Test compound | Compound of Example 11 | Compound of Comparative Example 2 |
|---|---|---|---|
| $C_{max}$ (ng/mL) | Oral administration | 279 | 146 |
| $AUC_{0-\infty, po}$ (ng h/mL) | | 2731 | 849 |
| $t_{1/2}$ (h) | | 7.55 | 6.56 |
| $CL_{tot}$ (mL/h/kg) | Intravenous administration | 195 | 501 |
| BA (%) | | 52.6 | 42.6 |

As is shown in FIGS. 17 and 18, the mean plasma concentration of the compound of Example 11 after administration to cynomolgus monkeys was higher than the mean plasma concentration of the compound of Comparative Example 2 after administration to cynomolgus monkeys at all time points.

As is shown in Table 4, the maximum plasma concentration ($C_{max}$) of the compound of Example 11 in the case of oral administration was 279 ng/mL; whereas the $C_{max}$ of the compound of Comparative Example 2 was 146 ng/mL. The elimination half-life ($t_{1/2}$) of the compound of Example 11 in the plasma in the case of the oral administration was 7.55 h; whereas the $t_{1/2}$ of the compound of Comparative Example 2 was 6.56 h. The total body clearance ($CL_{tot}$) of the compound of Example 11 representing the elimination rate of the compound was 195 mL/h/kg; whereas the $CL_{tot}$ of the compound of Comparative Example 2 was 501 mL/h/kg. The bioavailability (BA) of the compound of Example 11 representing the percentage of oral absorption of the compound was 52.6%; whereas the BA of the compound of Comparative Example 2 was 42.6%.

From the results, it was demonstrated that the cyclic amine derivative (I) or a pharmacologically acceptable salt thereof has higher oral absorbability and can provide a higher plasma concentration compared to an imidazole derivative described in International Publication WO No. 2013/147160.

Example 18—Evaluation of the Inducibility of Cytoplasmic Vacuolation Using Aortic Smooth Muscle Cells Using aortic smooth muscle cells as an in vitro evaluation system for the inductibility of cytoplasmic vacuolation by a compound, the inducibility of cytoplasmic vacuolation by the cyclic amine derivative (I) or a pharmacologically acceptable salt thereof was evaluated.

1. Experimental Method

As a test compound, the compound of Example 3, 9, 11, 12 or compounds of Comparative Examples 2 to 6 were used. Canine aortic smooth muscle cells (Canine Aortic Smooth Muscle Cells, supply source: Toyobo Co., Ltd.) or human aortic smooth muscle cells of (T/G HA-VSMG, supply source: ATCC) were treated with a test compound (1.0 or 1.2 mmol/L in concentration) for 24 hours or 2 weeks. The cells were stained with HE, immunohistochemically for LAMP-2 or toluidine blue, and thereafter the presence or absence of cytoplasmic vacuolation was determined by using an optical microscope.

2. Results

The evaluation results of the inducibility of cytoplasmic vacuolation are shown in Tables 5 and 6. Table 5 shows the evaluation results using canine aortic smooth muscle cells (test compound concentration: 1.0 mmol/L, treatment time with the test compound: 24 hours); whereas Table 6 shows the evaluation results using human aortic smooth muscle cells (test compound concentration: 1.0 or 1.2 mmol/L, treatment time with the test compound: 24 hours or 2 weeks). The term "present" in the tables means that cytoplasmic vacuolation was observed; whereas the term "absent" means that cytoplasmic vacuolation was not observed.

TABLE 5

| Canine aortic smooth muscle cells | |
|---|---|
| Test compound Concentration: 1.0 mmol/L Treatment time: 24 hours | Inducibility of cytoplasmic vacuolation |
| Compound of Example 11 | Absent |
| Compound of Comparative Example 2 | Present |
| Compound of Comparative Example 3 | Present |

TABLE 5-continued

Canine aortic smooth muscle cells

Test compound
Concentration: 1.0 mmol/L         Inducibility of
Treatment time: 24 hours          cytoplasmic vacuolation

| Test compound | Inducibility of cytoplasmic vacuolation |
|---|---|
| Compound of Comparative Example 4 | Present |
| Compound of Comparative Example 5 | Present |
| Compound of Comparative Example 6 | Present |

As is shown in Table 5, the inducibility of cytoplasmic vacuolation in canine aortic smooth muscle cells by the compound of Example 11 was evaluated as "absent," meaning that cytoplasmic vacuolation was not observed. In contrast, we found that all compounds of Comparative Examples have the inducibility of cytoplasmic vacuolation in canine aortic smooth muscle cells.

TABLE 6

Human aortic smooth muscle cells

| Test compound | | Inducibility of cytoplasmic vacuolation |
|---|---|---|
| Compound of Example 3 | Concentration: 1.2 mmol/L Treatment time: 24 hours | Absent |
| Compound of Example 9 | Concentration: 1.2 mmol/L Treatment time: 24 hours | Absent |
| Compound of Example 11 | Concentration: 1.0 mmol/L Treatment time: 24 hours | Absent |
| Compound of Example 11 | Concentration: 1.0 mmol/L Treatment time: 2 weeks | Absent |
| Compound of Example 12 | Concentration: 1.0 mmol/L Treatment time: 24 hours | Absent |
| Compound of Comparative Example 2 | Concentration: 1.0 mmol/L Treatment time: 24 hours | Present |

As is shown in Table 6, the inducibility of cytoplasmic vacuolation in human aortic smooth muscle cells by the compound of Example 3, 9, 11 or 12 was evaluated as "absent," meaning that cytoplasmic vacuolation was not observed. In addition, cytoplasmic vacuolation was not observed by the compound of Example 11 even if the treatment time was extended up to two weeks. In contrast, we found that the compound of Comparative Example 2 has the inducibility of cytoplasmic vacuolation in human aortic smooth muscle cells.

From the results, it was demonstrated that the inducibility of cytoplasmic vacuolation by the cyclic amine derivative (I) or a pharmacologically acceptable salt thereof was not observed. However, imidazole derivatives described in International Publication WO No. 2013/147160 have the inducibility of cytoplasmic vacuolation.

Example 19—Evaluation of Safety in Rat

The safety of the cyclic amine derivative (I) or a pharmacologically acceptable salt thereof was evaluated by subjecting rats to a two-week oral administration test.

1. Experimental Method

As a test compound, the compound of Example 11 or Comparative Example 2 was used. The compound of Example 11 or Comparative Example 2 was administered orally to Crl: CD (SD) rats (7 weeks old, female and male; from Charles River Laboratories, Inc.), for 2 weeks. Clinical observation, body weight measurement, food intake measurement, ophthalmologic examination (the compound of Example 11, alone), hematological examination, blood chemistry examination, urinalysis, bone marrow examination, pathological anatomical examination, organ weight measurement, histopathological examination and immunotoxicity test were carried out. In addition, toxicokinetics (TK) measurement was carried out on Day 1 and Day 14 after administration. It was confirmed that each test compound was exposed. The administration dose of a test compound was specified as 0, 250, 500, 1000 mg/kg/day and administration volume was specified as 10 mL/kg. As an administration solvent, phosphate-buffered saline was used for the compound of Example 11 and distilled water was used for the compound of Comparative Example 2.

2. Results

In rats to which the compound of Comparative Example 2 was orally administered in a dose of 250 mg/kg/day for 2 weeks, abnormality was not observed in either one of examination items. However, when the compound of Comparative Example 2 was administered in a dose of 500 mg/kg/day or more, vacuolation was observed in e.g., the media of blood vessels of submandibular gland. From this, the no observed adverse effect level of the compound of Comparative Example 2 was estimated as 250 mg/kg/day. In contrast, in rats to which the compound of Example 11 was administrated in a dose of up to 1000 mg/kg/day, abnormality was not observed in either one of examination items. From this, the no observed adverse effect level of the compound of Example 11 was estimated as 1000 mg/kg/day or more.

From the results, we demonstrated that the no observed adverse effect level of the cyclic amine derivative (I) or a pharmacologically acceptable salt thereof is high compared to that of an imidazole derivative described in International Publication WO No. 2013/147160.

The medicinal properties (drug efficacy, pharmacokinetics and safety) of the cyclic amine derivative (I) or a pharmacologically acceptable salt thereof, which were obtained from the results of the above Examples are shown in Table 7 in comparison with those of an imidazole derivative described in International Publication WO No. 2013/147160. The general formulas of the cyclic amine derivative (I) or a pharmacologically acceptable salt thereof and an imidazole derivative described in International Publication WO No. 2013/147160 are shown in Table 8.

TABLE 7

| | | Object of comparison | |
|---|---|---|---|
| Items of comparison | | Cyclic amine derivative (I) or a Pharmacologically acceptable salt thereof | Imidazole derivative described in International Publication WO No. 2013/147160 (Patent Literature 4) |
| Efficacy | Dose | Further low | Low |
| | Persistency | Long | Short |
| Pharmacokinetics | Metabolic stability | Further high | High |
| | Oral absorbability | High | Low |
| | Plasma concentration | High | Low |
| Safety | Non-toxic level | High | Low |
| | Inducibility of cytoplasmic vacuolation | Absent | Present |

TABLE 8

| Object of comparison | General formula |
|---|---|
| Cyclic amine derivative (I) or a pharmacologically acceptable salt thereof | (structure shown) |
| Imidazole derivative described in International Publication WO No. 2013/147160 (Patent Literature 4) | (structure shown) |

[wherein $R^1$ represents an alkyl group having 1 to 6 carbon atoms optionally substituted with a halogen atom or an alkyloxy group having 1 to 4 carbon atoms, $R^2$ represents a hydrogen atom or a halogen atom; and X represents a single bond or a double bond.]

As is shown in Table 7, we demonstrated that the cyclic amine derivative (I) or a pharmacologically acceptable salt thereof has more excellent properties as a medicine than an imidazole derivative described in International Publication WO No. 2013/147160 with respect to all comparative items (efficacy, pharmacokinetics and safety).

The Imidazole derivative described in International Publication WO No. 2013/147160 is represented by the general formula described in the lower stage of Table 8. International Publication WO No. 2013/147160 (paragraph [0209]) discloses that if the chemical structure represented by the general formula described in the lower stage of Table 8 is converted into another (chemical) structure, i.e., "if the dimethyl amino group, X or the imidazolyl group is replaced with another group or structure, analgesic action significantly decreased." In contrast, our cyclic amine derivative (I) or a pharmacologically acceptable salt thereof corresponds to the compound represented by a chemical structure obtained by replacing chemical structure X shown in the general formula in the lower stage of Table 8 with another chemical structure. Nevertheless, our cyclic amine derivative (I) or a pharmacologically acceptable salt thereof has not only excellent analgesic action but also persistence of the efficacy thereof, unlike the imidazole derivative described in International Publication WO No. 2013/147160, and further has high safety and excellent pharmacokinetics (e.g., metabolic stability, oral absorbability and plasma concentration). Accordingly, we found that the cyclic amine derivative (I) or a pharmacologically acceptable salt thereof is a compound having excellent properties as a medicine.

INDUSTRIAL APPLICABILITY

The cyclic amine derivative or a pharmacologically acceptable salt thereof can be used as medicines for pain symptoms since it can exhibit an analgesic action against pain, in particular, neuropathic pain or fibromyalgia syndrome.

The cyclic amine derivative or a pharmacologically acceptable salt thereof has high safety, excellent pharmacokinetics such as metabolic stability, oral absorbability and plasma concentration, and persistence of drug efficacy and, thus, is useful as a therapeutic agent for pain, particularly neuropathic pain or fibromyalgia syndrome.

The invention claimed is:

1. A cyclic amine represented by general formula (I) or a pharmacologically acceptable salt thereof:

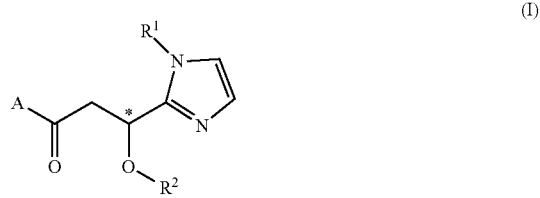

(I)

wherein carbon marked with * is asymmetric carbon; and
A represents a group represented by general formulae (IIa), (IIb) or (IIc):

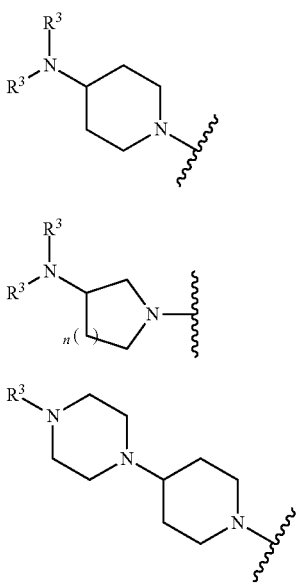

wherein R¹ represents a methyl group or an ethyl group optionally substituted with a halogen atom, R² represents a hydrogen atom or an alkylcarbonyl group having 2 to 5 carbon atoms, each R³ independently represents a methyl group or an ethyl group, and n represents 1 or 2.

2. The cyclic amine or the pharmacologically acceptable salt thereof according to claim 1, wherein A is a group represented by general formula (IIa).

3. The cyclic amine or the pharmacologically acceptable salt thereof according to claim 1, wherein A is a group represented by general formulae (IIb) or (IIc).

4. The cyclic amine or the pharmacologically acceptable salt thereof according to claim 1, wherein A is a group represented by general formula (IIa) and the stereochemical configuration of the asymmetric carbon marked with * is S.

5. The cyclic amine or the pharmacologically acceptable salt thereof according to claim 1, wherein R¹ represents a methyl group or an ethyl group optionally substituted with a fluorine atom.

6. The cyclic amine or the pharmacologically acceptable salt thereof according to claim 1, wherein R¹ is a methyl group, an ethyl group, a difluoromethyl group or a 2,2,2-trifluoroethyl group.

7. A medicine comprising the cyclic amine or the pharmacologically acceptable salt thereof according to claim 1 as an active ingredient.

8. An analgesic agent comprising the cyclic amine or the pharmacologically acceptable salt thereof according to claim 1 as an active ingredient.

9. A method of treating pain comprising administering a therapeutically effective amount of the cyclic amine represented by general formula (I) or the pharmacologically acceptable salt thereof according to claim 1 to a patient in need thereof.

10. A method of treating neuropathic pain comprising administering a therapeutically effective amount of the cyclic amine represented by general formula (I) or the pharmacologically acceptable salt thereof according to claim 1 to a patient in need thereof.

11. A method of treating fibromyalgia syndrome comprising administering a therapeutically effective amount of the cyclic amine represented by general formula (I) or the pharmacologically acceptable salt thereof according to claim 1 to a patient in need thereof.

* * * * *